United States Patent
Bonfiglio et al.

(10) Patent No.: US 12,331,074 B2
(45) Date of Patent: Jun. 17, 2025

(54) SITE-SPECIFIC SERINE ADP-RIBOSYLATED PROTEINS AND PEPTIDES AND METHOD FOR PRODUCING THE SAME

(71) Applicant: Max-Planck-Gesellschaft zur Förderung der Wissenschaften e.V., Munich (DE)

(72) Inventors: Juan José Bonfiglio, Munich (DE); Ivan Matic, Cologne (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 1069 days.

(21) Appl. No.: 17/276,772

(22) PCT Filed: Sep. 17, 2019

(86) PCT No.: PCT/EP2019/074885
§ 371 (c)(1),
(2) Date: Mar. 16, 2021

(87) PCT Pub. No.: WO2020/058277
PCT Pub. Date: Mar. 26, 2020

(65) Prior Publication Data
US 2021/0261603 A1   Aug. 26, 2021

(30) Foreign Application Priority Data
Sep. 19, 2018   (EP) .................................. 18195384

(51) Int. Cl.
| C07K 1/107 | (2006.01) |
| C07K 1/12 | (2006.01) |
| C07K 1/18 | (2006.01) |
| C07K 1/22 | (2006.01) |
| C07K 1/34 | (2006.01) |
| C07K 1/36 | (2006.01) |
| C12P 21/00 | (2006.01) |

(52) U.S. Cl.
CPC .............. *C07K 1/1077* (2013.01); *C07K 1/12* (2013.01); *C12P 21/005* (2013.01); *C07K 1/18* (2013.01); *C07K 1/22* (2013.01); *C07K 1/34* (2013.01); *C07K 1/36* (2013.01)

(58) Field of Classification Search
CPC ... C07K 1/12; C07K 1/18; C07K 1/22; C07K 1/34; C07K 1/36; C12P 21/005; C12Y 204/0203
See application file for complete search history.

(56) References Cited

U.S. PATENT DOCUMENTS

2021/0363176 A1* 11/2021 Bonfiglio ....... C12Y 302/01143

FOREIGN PATENT DOCUMENTS

WO   2014/192923 A1   12/2014

OTHER PUBLICATIONS

Rodriguez-Collazo et al. Robust methods for purification of histones from cultured mammalian cells with the preservation of their native modifications Nucleic Acid Research (2009), 37(11): 1-15) (Year: 2009).*
Cohen et al. Discovery of a protein phosphatase activity encoded in the genome of bacteriophage lambda. Biochem J (1989),260: 931-934. (Year: 1989).*
Kistemaker et al. Synthesis and Macrodomain Binding of Mono-ADP-Ribosylated Peptides. Angew. Chem Int. Ed. (2016), 55: 10634-10638. (Year: 2016).*
Patent Cooperation Treaty, International Search Report and Written Opinion issued in PCT/EP2019/074885, Dec. 12, 2019, pp. 1-18.
Larsen et al., "Systems-wide Analysis of Serine ADP-Ribosylation Reveals Widespread Occurrence and Site-Specific Overlap with Phosphorylation", Cell Reports, Aug. 28, 2018, pp. 2493-2505, vol. 24(9).
Leidecker et al., "Serine is a new target residue for endogenous ADP-ribosylation on histones", Nature Chemical Biology, Oct. 10, 2016, pp. 998-1000, vol. 12(12).
Bonfiglio et al., "Serine ADP-Ribosylation Depends on HPF1", Molecular Cell, Mar. 2, 2017, pp. 932-940, vol. 65(5).
Palazzo et al., "Serine is the major residue for ADP-ribosylation upon DNA damage", eLIFE, Feb. 26, 2018, pp. 1-12, vol. 7(26).
Dai et al., "Identification and Functional Characterizations of N-Terminal [alpha]-N-Methylation and Phosphorylation of Serine 461 in Human Poly(ADP-ribose) Polymerase 3", Journal Proteome Research, Jun. 5, 2015, pp. 2575-2582, vol. 14(6).
European Patent Office, Extended European Search Report issued in EP Patent Application No. 18195384.5, Jun. 6, 2019, pp. 1-11.

* cited by examiner

*Primary Examiner* — Iqbal H Chowdhury
(74) *Attorney, Agent, or Firm* — Pillsbury Winthrop Shaw Pittman LLP

(57) ABSTRACT

The present invention relates to a method for producing a site-specifically serine ADP-ribosylated protein or peptide being, comprising: (a) subjecting a protein or peptide comprising or consisting of an amino acid sequence comprising two or more serines, wherein at least one serine is phosphorylated and at least one serine is non-phosphorylated, to a serine ADP-ribosylation reaction. The present invention also relates to a site-specifically serine ADP-ribosylated protein or peptide produced by the method of the invention.

16 Claims, 8 Drawing Sheets
Specification includes a Sequence Listing.

A

B

Figure 1:
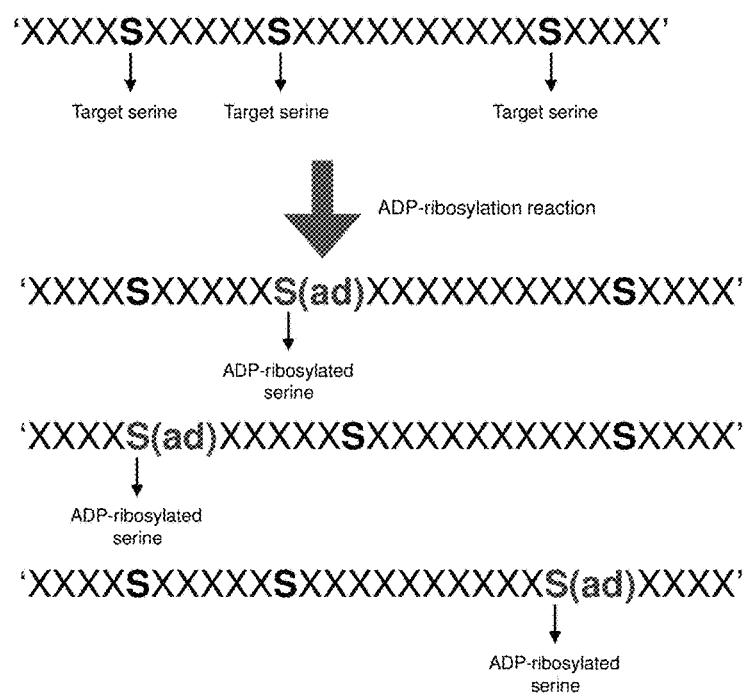
Figure 1:

Figure 1 – continued
C
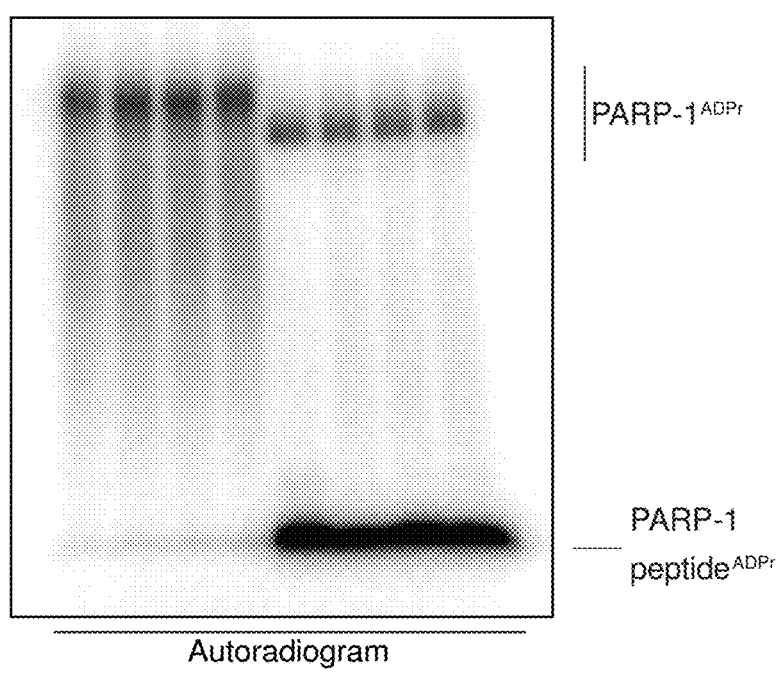
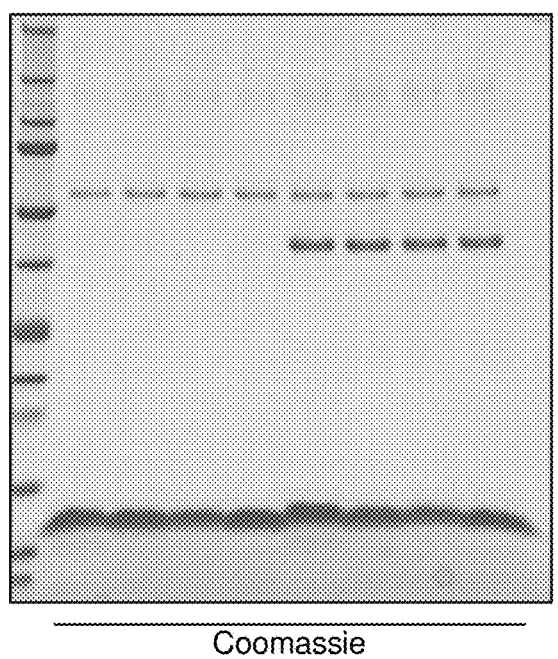

Figure 1 - continued
D
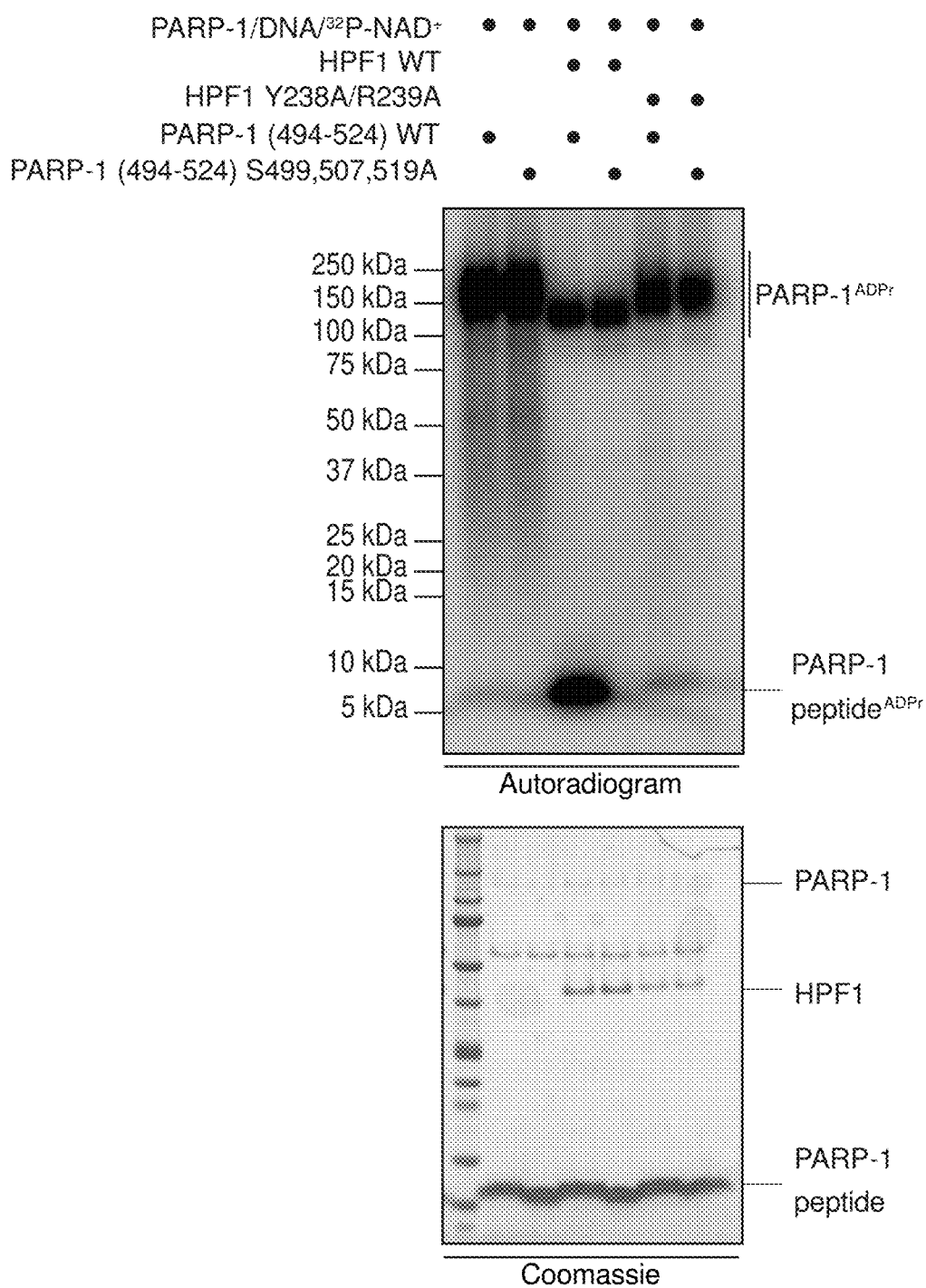

Figure 1 - continued
E
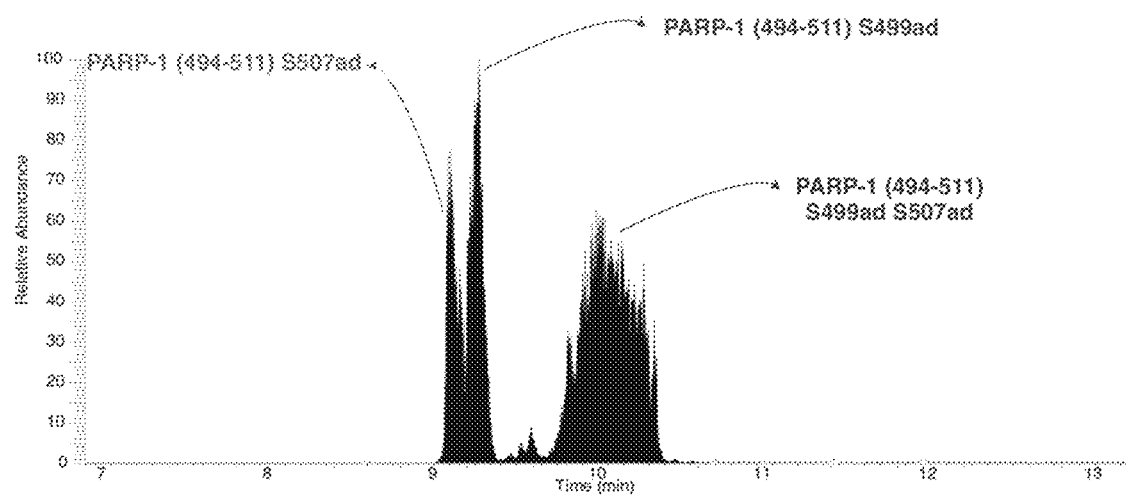

A

B

Figure 3:
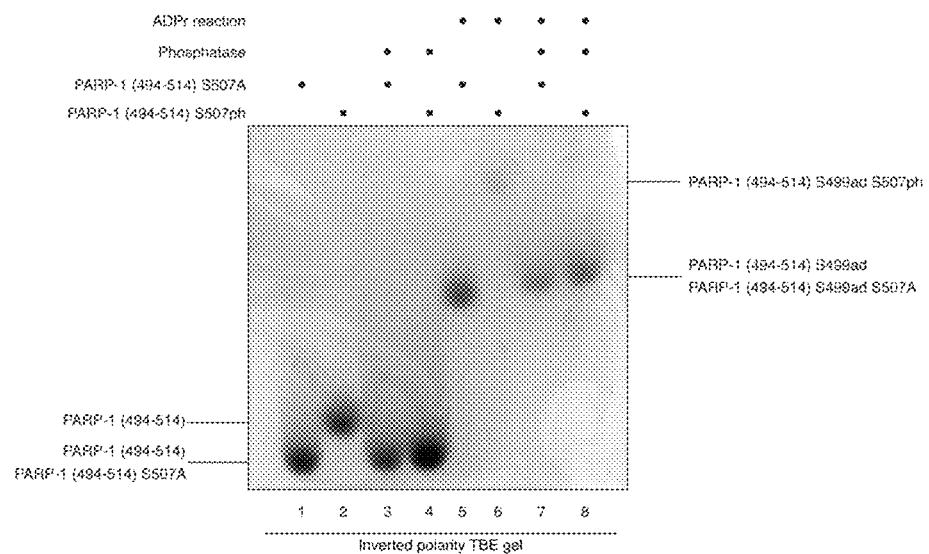
Figure 3:
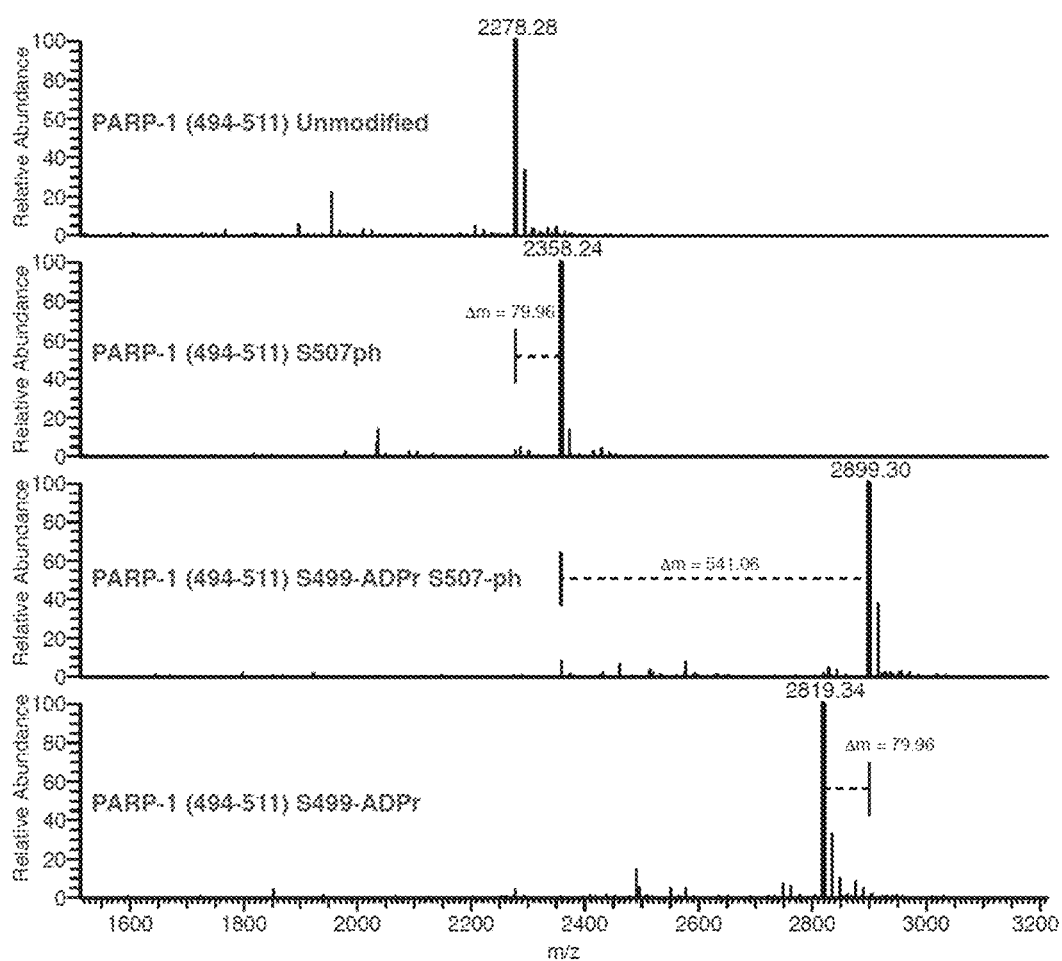

Figure 3 - continued
C
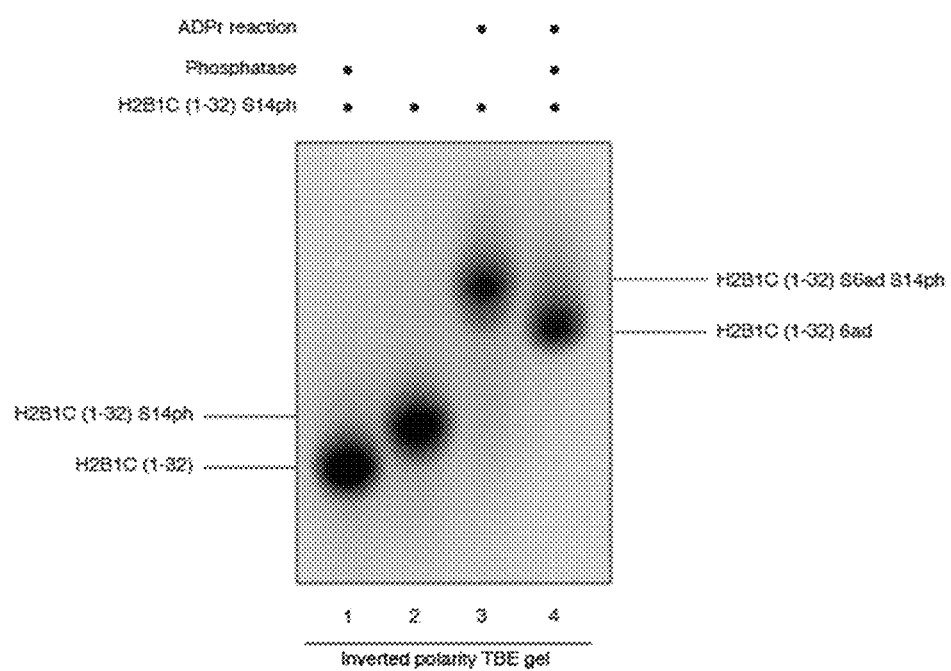

A

B

SEQUENCE LISTING

<160> NUMBER OF SEQ ID NOS: 311

<210> SEQ ID NO 1
<211> LENGTH: 1014
<212> TYPE: PRT
<213> ORGANISM: Homo sapiens

<400> SEQUENCE: 1

```
Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Val Thr Gly
                85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
    290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
        355                 360                 365
```

-continued

```
Pro Pro Pro Ser Thr Ala Ser Ala Pro Ala Ala Val Asn Ser Ser Ala
    370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
                420                 425                 430

Lys Lys Glu Val Glu Lys Met Asn Lys Lys Met Glu Glu Val Lys Glu
                435                 440                 445

Ala Asn Ile Arg Val Val Ser Glu Asp Phe Leu Gln Asp Val Ser Ala
    450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Ala Pro Arg
                485                 490                 495

Gly Lys Ser Gly Ala Ala Leu Ser Lys Lys Ser Lys Gly Gln Val Lys
                500                 505                 510

Glu Glu Gly Ile Asn Lys Ser Glu Lys Arg Met Lys Leu Thr Leu Lys
                515                 520                 525

Gly Gly Ala Ala Val Asp Pro Asp Ser Gly Leu Glu His Ser Ala His
                530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
                580                 585                 590

Gly Thr Val Ile Gly Ser Asn Lys Leu Glu Gln Met Pro Ser Lys Glu
                595                 600                 605

Asp Ala Ile Glu His Phe Met Lys Leu Tyr Glu Lys Thr Gly Asn
    610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
                660                 665                 670

Ile Lys Met Ile Phe Asp Val Glu Ser Met Lys Lys Ala Met Val Glu
                675                 680                 685

Tyr Glu Ile Asp Leu Gln Lys Met Pro Leu Gly Lys Leu Ser Lys Arg
                690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
                740                 745                 750

Asn Asn Ala Asp Ser Val Gln Ala Lys Val Glu Met Leu Asp Asn Leu
                755                 760                 765

Leu Asp Ile Glu Val Ala Tyr Ser Leu Leu Arg Gly Gly Ser Asp Asp
                770                 775                 780

Ser Ser Lys Asp Pro Ile Asp Val Asn Tyr Glu Lys Leu Lys Thr Asp
```

```
                785                 790                 795                 800
        Ile Lys Val Val Asp Arg Asp Ser Glu Glu Ala Glu Ile Ile Arg Lys
                        805                 810                 815

Tyr Val Lys Asn Thr His Ala Thr Thr His Asn Ala Tyr Asp Leu Glu
                        820                 825                 830

Val Ile Asp Ile Phe Lys Ile Glu Arg Glu Gly Glu Cys Gln Arg Tyr
                        835                 840                 845

Lys Pro Phe Lys Gln Leu His Asn Arg Arg Leu Leu Trp His Gly Ser
                        850                 855                 860

Arg Thr Thr Asn Phe Ala Gly Ile Leu Ser Gln Gly Leu Arg Ile Ala
        865                 870                 875                 880

Pro Pro Glu Ala Pro Val Thr Gly Tyr Met Phe Gly Lys Gly Ile Tyr
                        885                 890                 895

Phe Ala Asp Met Val Ser Lys Ser Ala Asn Tyr Cys His Thr Ser Gln
                        900                 905                 910

Gly Asp Pro Ile Gly Leu Ile Leu Leu Gly Glu Val Ala Leu Gly Asn
                        915                 920                 925

Met Tyr Glu Leu Lys His Ala Ser His Ile Ser Lys Leu Pro Lys Gly
                930                 935                 940

Lys His Ser Val Lys Gly Leu Gly Lys Thr Thr Pro Asp Pro Ser Ala
        945                 950                 955                 960

Asn Ile Ser Leu Asp Gly Val Asp Val Pro Leu Gly Thr Gly Ile Ser
                        965                 970                 975

Ser Gly Val Asn Asp Thr Ser Leu Leu Tyr Asn Glu Tyr Ile Val Tyr
                        980                 985                 990

Asp Ile Ala Gln Val Asn Leu Lys  Tyr Leu Leu Lys Leu Lys Phe Asn
                        995                 1000                1005

Phe Lys  Thr Ser Leu Trp
            1010

<210> SEQ ID NO 2
<211> LENGTH: 1014
<212> TYPE: PRT
<213> ORGANISM: Artificial Sequence
<220> FEATURE:
<223> OTHER INFORMATION: Poly (ADP-ribose) polymerase 1 E988Q

<400> SEQUENCE: 2

Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
                20                  25                  30

Leu Arg Met Ala Ile Met Val Gln Ser Pro Met Phe Asp Gly Lys Val
            35                  40                  45

Pro His Trp Tyr His Phe Ser Cys Phe Trp Lys Val Gly His Ser Ile
        50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95

Lys Gly Gln Asp Gly Ile Gly Ser Lys Ala Glu Lys Thr Leu Gly Asp
                100                 105                 110

Phe Ala Ala Glu Tyr Ala Lys Ser Asn Arg Ser Thr Cys Lys Gly Cys
            115                 120                 125

Met Glu Lys Ile Glu Lys Gly Gln Val Arg Leu Ser Lys Lys Met Val
```

-continued

```
             130                 135                 140
Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
            195                 200                 205

Lys Gly Asp Glu Val Asp Gly Val Asp Glu Val Ala Lys Lys Lys Ser
        210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
        290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
        355                 360                 365

Pro Pro Pro Ser Thr Ala Ser Ala Pro Ala Ala Val Asn Ser Ser Ala
    370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Lys Met Glu Glu Val Lys Glu
        435                 440                 445

Ala Asn Ile Arg Val Val Ser Glu Asp Phe Leu Gln Asp Val Ser Ala
    450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
        515                 520                 525

Gly Gly Ala Ala Val Asp Pro Asp Ser Gly Leu Glu His Ser Ala His
    530                 535                 540

Val Leu Glu Lys Gly Gly Lys Val Phe Ser Ala Thr Leu Gly Leu Val
545                 550                 555                 560
```

-continued

```
Asp Ile Val Lys Gly Thr Asn Ser Tyr Tyr Lys Leu Gln Leu Leu Glu
            565                 570                 575

Asp Asp Lys Glu Asn Arg Tyr Trp Ile Phe Arg Ser Trp Gly Arg Val
                580                 585                 590

Gly Thr Val Ile Gly Ser Asn Lys Leu Glu Gln Met Pro Ser Lys Glu
            595                 600                 605

Asp Ala Ile Glu His Phe Met Lys Leu Tyr Glu Glu Lys Thr Gly Asn
            610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
            675                 680                 685

Tyr Glu Ile Asp Leu Gln Lys Met Pro Leu Gly Lys Leu Ser Lys Arg
            690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
            755                 760                 765

Leu Asp Ile Glu Val Ala Tyr Ser Leu Arg Gly Gly Ser Asp Asp
            770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Asn Ala Tyr Asp Leu Glu
            820                 825                 830

Val Ile Asp Ile Phe Lys Ile Glu Arg Glu Gly Glu Cys Gln Arg Tyr
            835                 840                 845

Lys Pro Phe Lys Gln Leu His Asn Arg Arg Leu Leu Trp His Gly Ser
850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
                885                 890                 895

Phe Ala Asp Met Val Ser Lys Ser Ala Asn Tyr Cys His Thr Ser Gln
            900                 905                 910

Gly Asp Pro Ile Gly Leu Ile Leu Leu Gly Glu Val Ala Leu Gly Asn
            915                 920                 925

Met Tyr Glu Leu Lys His Ala Ser His Ile Ser Lys Leu Pro Lys Gly
            930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975
```

Ser Gly Val Asn Asp Thr Ser Leu Leu Tyr Asn Gln Tyr Ile Val Tyr
            980                 985                 990

Asp Ile Ala Gln Val Asn Leu Lys Tyr Leu Leu Lys Leu Lys Phe Asn
        995                 1000                1005

Phe Lys Thr Ser Leu Trp
    1010

<210> SEQ ID NO 3
<211> LENGTH: 1013
<212> TYPE: PRT
<213> ORGANISM: Mus musculus

<400> SEQUENCE: 3

Met Ala Glu Ala Ser Glu Arg Leu Tyr Arg Val Gln Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly Gln Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Ala Gly
                85                  90                  95

Lys Gly Gln Asp Gly Ser Gly Gly Lys Ala Glu Lys Thr Leu Gly Asp
            100                 105                 110

Phe Ala Ala Glu Tyr Ala Lys Ser Asn Arg Ser Met Cys Lys Gly Cys
        115                 120                 125

Leu Glu Lys Ile Glu Lys Gly Gln Met Arg Leu Ser Lys Met Val
    130                 135                 140

Asp Pro Glu Lys Pro Gln Leu Gly Met Ile Asp Arg Trp Tyr His Pro
145                 150                 155                 160

Thr Cys Phe Val Lys Lys Arg Asp Glu Leu Gly Phe Arg Pro Glu Tyr
                165                 170                 175

Ser Ala Ser Gln Leu Lys Gly Phe Ser Leu Leu Ser Ala Glu Asp Lys
            180                 185                 190

Glu Ala Leu Lys Lys Gln Leu Pro Ala Ile Lys Asn Glu Gly Lys Arg
        195                 200                 205

Lys Gly Asp Glu Val Asp Gly Thr Asp Glu Val Ala Lys Lys Lys Ser
    210                 215                 220

Arg Lys Glu Thr Asp Lys Tyr Ser Lys Leu Glu Lys Ala Leu Lys Ala
225                 230                 235                 240

Gln Asn Glu Leu Ile Trp Asn Ile Lys Asp Glu Leu Lys Lys Ala Cys
                245                 250                 255

Ser Thr Asn Asp Leu Lys Glu Leu Leu Ile Phe Asn Gln Gln Gln Val
            260                 265                 270

Pro Ser Gly Glu Ser Ala Ile Leu Asp Arg Val Ala Asp Gly Met Ala
        275                 280                 285

Phe Gly Ala Leu Leu Pro Cys Lys Glu Cys Ser Gly Gln Leu Val Phe
    290                 295                 300

Lys Ser Asp Ala Tyr Tyr Cys Thr Gly Asp Val Thr Ala Trp Thr Lys
305                 310                 315                 320

Cys Met Val Lys Thr Gln Asn Pro Ser Arg Lys Glu Trp Val Thr Pro
                325                 330                 335

-continued

```
Lys Glu Phe Arg Glu Ile Ser Tyr Leu Lys Lys Leu Lys Val Lys Lys
                340                 345                 350

Gln Asp Arg Ile Phe Pro Pro Glu Ser Ser Ala Pro Ile Thr Val His
            355                 360                 365

Trp Pro Leu Ser Val Thr Ser Ala Pro Thr Ala Val Asn Ser Ser Ala
370                 375                 380

Pro Ala Asp Lys Pro Leu Ser Asn Met Lys Ile Leu Thr Leu Gly Lys
385                 390                 395                 400

Leu Ser Gln Asn Lys Asp Glu Ala Lys Ala Val Ile Glu Lys Leu Gly
                405                 410                 415

Gly Lys Leu Thr Gly Ser Ala Asn Lys Ala Ser Leu Cys Ile Ser Ile
            420                 425                 430

Lys Lys Glu Val Glu Lys Met Asn Lys Lys Met Glu Glu Val Lys Glu
            435                 440                 445

Ala Asn Ile Arg Val Val Ser Glu Asp Phe Leu Gln Asp Val Ser Ala
        450                 455                 460

Ser Thr Lys Ser Leu Gln Asp Leu Leu Ser Ala His Ser Leu Ser Pro
465                 470                 475                 480

Trp Gly Ala Glu Val Lys Ala Glu Pro Gly Glu Val Val Ala Pro Arg
                485                 490                 495

Gly Lys Ser Ala Ala Pro Ser Lys Lys Ser Lys Gly Cys Phe Lys Glu
            500                 505                 510

Glu Gly Val Asn Lys Ser Glu Lys Arg Met Lys Leu Thr Leu Lys Gly
            515                 520                 525

Gly Ala Val Asp Pro Asp Ser Gly Leu Glu His Ser Ala His Val
            530                 535                 540

Leu Glu Lys Gly Gly Lys Val Phe Ser Ala Thr Leu Gly Leu Val Asp
545                 550                 555                 560

Ile Val Lys Gly Thr Asn Ser Tyr Tyr Lys Leu Gln Leu Leu Glu Asp
                565                 570                 575

Asp Lys Glu Ser Arg Tyr Trp Ile Phe Arg Ser Trp Gly Arg Leu Gly
            580                 585                 590

Thr Val Ile Gly Ser Asn Lys Leu Glu Gln Met Pro Ser Lys Glu Glu
            595                 600                 605

Ala Val Glu Gln Phe Met Lys Leu Tyr Glu Glu Lys Thr Gly Asn Ala
        610                 615                 620

Trp His Ser Lys Asn Phe Thr Lys Tyr Pro Lys Lys Phe Tyr Pro Leu
625                 630                 635                 640

Glu Ile Asp Tyr Gly Gln Asp Glu Glu Ala Val Lys Lys Leu Thr Val
                645                 650                 655

Lys Pro Gly Thr Lys Ser Lys Leu Pro Lys Pro Val Gln Glu Leu Val
            660                 665                 670

Gly Met Ile Phe Asp Val Asp Ser Met Lys Lys Ala Leu Val Glu Tyr
            675                 680                 685

Glu Ile Asp Leu Gln Lys Met Pro Leu Gly Lys Leu Ser Arg Arg Gln
        690                 695                 700

Ile Gln Ala Ala Tyr Ser Ile Leu Ser Glu Val Gln Gln Pro Val Ser
705                 710                 715                 720

Gln Gly Ser Ser Glu Ser Gln Ile Leu Asp Leu Ser Asn Arg Phe Tyr
                725                 730                 735

Thr Leu Ile Pro His Asp Phe Gly Met Lys Lys Pro Pro Leu Leu Asn
            740                 745                 750
```

-continued

Asn Ala Asp Ser Val Gln Ala Lys Val Glu Met Leu Asp Asn Leu Leu
            755                 760                 765

Asp Ile Glu Val Ala Tyr Ser Leu Leu Arg Gly Gly Ser Asp Asp Ser
    770                 775                 780

Ser Lys Asp Pro Ile Asp Val Asn Tyr Glu Lys Leu Lys Thr Asp Ile
785                 790                 795                 800

Lys Val Val Asp Arg Asp Ser Glu Glu Ala Glu Val Ile Arg Lys Tyr
                805                 810                 815

Val Lys Asn Thr His Ala Thr Thr His Asn Ala Tyr Asp Leu Glu Val
            820                 825                 830

Ile Asp Ile Phe Lys Ile Glu Arg Glu Gly Glu Ser Gln Arg Tyr Lys
        835                 840                 845

Pro Phe Arg Gln Leu His Asn Arg Arg Leu Leu Trp His Gly Ser Arg
    850                 855                 860

Thr Thr Asn Phe Ala Gly Ile Leu Ser Gln Gly Leu Arg Ile Ala Pro
865                 870                 875                 880

Pro Glu Ala Pro Val Thr Gly Tyr Met Phe Gly Lys Gly Ile Tyr Phe
                885                 890                 895

Ala Asp Met Val Ser Lys Ser Ala Asn Tyr Cys His Thr Ser Gln Gly
            900                 905                 910

Asp Pro Ile Gly Leu Ile Met Leu Gly Glu Val Ala Leu Gly Asn Met
        915                 920                 925

Tyr Glu Leu Lys His Ala Ser His Ile Ser Lys Leu Pro Lys Gly Lys
    930                 935                 940

His Ser Val Lys Gly Leu Gly Lys Thr Thr Pro Asp Pro Ser Ala Ser
945                 950                 955                 960

Ile Thr Leu Glu Gly Val Glu Val Pro Leu Gly Thr Gly Ile Pro Ser
                965                 970                 975

Gly Val Asn Asp Thr Ala Leu Leu Tyr Asn Glu Tyr Ile Val Tyr Asp
            980                 985                 990

Ile Ala Gln Val Asn Leu Lys Tyr  Leu Leu Lys Leu Lys  Phe Asn Phe
        995                 1000                1005

Lys Thr  Ser Leu Trp
    1010

<210> SEQ ID NO 4
<211> LENGTH: 492
<212> TYPE: PRT
<213> ORGANISM: Mus musculus

<400> SEQUENCE: 4

Met Lys Leu Thr Leu Lys Gly Gly Ala Ala Val Asp Pro Asp Ser Gly
1               5                   10                  15

Leu Glu His Ser Ala His Val Leu Glu Lys Gly Gly Lys Val Phe Ser
            20                  25                  30

Ala Thr Leu Gly Leu Val Asp Ile Val Lys Gly Thr Asn Ser Tyr Tyr
        35                  40                  45

Lys Leu Gln Leu Leu Glu Asp Asp Lys Glu Ser Arg Tyr Trp Ile Phe
    50                  55                  60

Arg Ser Trp Gly Arg Leu Gly Thr Val Ile Gly Ser Asn Lys Leu Glu
65                  70                  75                  80

Gln Met Pro Ser Lys Glu Glu Ala Val Glu Gln Phe Met Lys Leu Tyr
                85                  90                  95

Glu Glu Lys Thr Gly Asn Ala Trp His Ser Lys Asn Phe Thr Lys Tyr
            100                 105                 110

```
Pro Lys Lys Phe Tyr Pro Leu Glu Ile Asp Tyr Gly Gln Asp Glu Glu
        115                 120                 125

Ala Val Lys Lys Leu Thr Val Lys Pro Gly Thr Lys Ser Lys Leu Pro
130                 135                 140

Lys Pro Val Gln Glu Leu Val Gly Met Ile Phe Asp Val Asp Ser Met
145                 150                 155                 160

Lys Lys Ala Leu Val Glu Tyr Glu Ile Asp Leu Gln Lys Met Pro Leu
                165                 170                 175

Gly Lys Leu Ser Arg Arg Gln Ile Gln Ala Ala Tyr Ser Ile Leu Ser
            180                 185                 190

Glu Val Gln Gln Pro Val Ser Gln Gly Ser Glu Ser Gln Ile Leu
        195                 200                 205

Asp Leu Ser Asn Arg Phe Tyr Thr Leu Ile Pro His Asp Phe Gly Met
    210                 215                 220

Lys Lys Pro Pro Leu Leu Asn Asn Ala Asp Ser Val Gln Ala Lys Val
225                 230                 235                 240

Glu Met Leu Asp Asn Leu Leu Asp Ile Glu Val Ala Tyr Ser Leu Leu
                245                 250                 255

Arg Gly Gly Ser Asp Asp Ser Ser Lys Asp Pro Ile Asp Val Asn Tyr
            260                 265                 270

Glu Lys Leu Lys Thr Asp Ile Lys Val Val Asp Arg Asp Ser Glu Glu
        275                 280                 285

Ala Glu Val Ile Arg Lys Tyr Val Lys Asn Thr His Ala Thr Thr His
    290                 295                 300

Asn Ala Tyr Asp Leu Glu Val Ile Asp Ile Phe Lys Ile Glu Arg Glu
305                 310                 315                 320

Gly Glu Ser Gln Arg Tyr Lys Pro Phe Arg Gln Leu His Asn Arg Arg
                325                 330                 335

Leu Leu Trp His Gly Ser Arg Thr Thr Asn Phe Ala Gly Ile Leu Ser
            340                 345                 350

Gln Gly Leu Arg Ile Ala Pro Pro Glu Ala Pro Val Thr Gly Tyr Met
        355                 360                 365

Phe Gly Lys Gly Ile Tyr Phe Ala Asp Met Val Ser Lys Ser Ala Asn
    370                 375                 380

Tyr Cys His Thr Ser Gln Gly Asp Pro Ile Gly Leu Ile Met Leu Gly
385                 390                 395                 400

Glu Val Ala Leu Gly Asn Met Tyr Glu Leu Lys His Ala Ser His Ile
                405                 410                 415

Ser Lys Leu Pro Lys Gly Lys His Ser Val Lys Gly Leu Gly Lys Thr
            420                 425                 430

Thr Pro Asp Pro Ser Ala Ser Ile Thr Leu Glu Gly Val Glu Val Pro
        435                 440                 445

Leu Gly Thr Gly Ile Pro Ser Gly Val Asn Asp Thr Ala Leu Leu Tyr
    450                 455                 460

Asn Glu Tyr Ile Val Tyr Asp Ile Ala Gln Val Asn Leu Lys Tyr Leu
465                 470                 475                 480

Leu Lys Leu Lys Phe Asn Phe Lys Thr Ser Leu Trp
                485                 490

<210> SEQ ID NO 5
<211> LENGTH: 1014
<212> TYPE: PRT
<213> ORGANISM: Rattus norvegicus
```

```
<400> SEQUENCE: 5

Met Ala Glu Ala Thr Glu Arg Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg Gln Pro Asp Thr Glu Val Asp Gly Phe Ser Glu Leu Arg Trp Asp
65                  70                  75                  80

Asp Gln Gln Lys Val Lys Lys Thr Ala Glu Ala Gly Val Ala Gly
                85                  90                  95

Lys Gly Gln His Gly Gly Gly Lys Ala Glu Lys Thr Leu Gly Asp
                100                 105                 110

Phe Ala Ala Glu Tyr Ala Lys Ser Asn Arg Ser Thr Cys Lys Gly Cys
            115                 120                 125

Met Glu Lys Ile Glu Lys Gly Gln Met Arg Leu Ser Lys Lys Met Leu
    130                 135                 140

Asp Pro Glu Lys Pro Gln Leu Gly Met Ile Asp Arg Trp Tyr His Pro
145                 150                 155                 160

Thr Cys Phe Val Lys Asn Arg Asp Glu Leu Gly Phe Arg Pro Glu Tyr
                165                 170                 175

Ser Ala Ser Gln Leu Lys Gly Phe Ser Leu Leu Ser Ala Glu Asp Lys
            180                 185                 190

Glu Ala Leu Lys Lys Gln Leu Pro Ala Val Lys Ser Glu Gly Lys Arg
        195                 200                 205

Lys Cys Asp Glu Val Asp Gly Ile Asp Glu Val Ala Lys Lys Lys Ser
    210                 215                 220

Lys Lys Gly Lys Asp Lys Glu Ser Ser Lys Leu Glu Lys Ala Leu Lys
225                 230                 235                 240

Ala Gln Asn Glu Leu Val Trp Asn Ile Lys Asp Glu Leu Lys Lys Ala
                245                 250                 255

Cys Ser Thr Asn Asp Leu Lys Glu Leu Leu Ile Phe Asn Gln Gln Gln
            260                 265                 270

Val Pro Ser Gly Glu Ser Ala Ile Leu Asp Arg Val Ala Asp Gly Met
        275                 280                 285

Ala Phe Gly Ala Leu Leu Pro Cys Lys Glu Cys Ser Gly Gln Leu Val
    290                 295                 300

Phe Lys Ser Asp Ala Tyr Tyr Cys Thr Gly Asp Val Thr Ala Trp Thr
305                 310                 315                 320

Lys Cys Met Val Lys Thr Gln Asn Pro Ser Arg Lys Glu Trp Val Thr
                325                 330                 335

Pro Lys Glu Phe Arg Glu Ile Ser Tyr Leu Lys Lys Leu Lys Ile Lys
            340                 345                 350

Lys Gln Asp Arg Leu Phe Pro Pro Glu Ser Ser Ala Pro Ala Pro Pro
        355                 360                 365

Ala Pro Pro Val Ser Ile Thr Ser Ala Pro Thr Ala Val Asn Ser Ser
    370                 375                 380

Ala Pro Ala Asp Lys Pro Leu Ser Asn Met Lys Ile Leu Thr Leu Gly
385                 390                 395                 400

Lys Leu Ser Gln Asn Lys Asp Glu Ala Lys Ala Met Ile Glu Lys Leu
                405                 410                 415
```

```
Gly Gly Lys Leu Thr Gly Ser Ala Asn Lys Ala Ser Leu Cys Ile Ser
            420                 425                 430
Thr Lys Lys Glu Val Glu Lys Met Ser Lys Lys Met Glu Glu Val Lys
                435                 440                 445
Ala Ala Asn Val Arg Val Val Cys Glu Asp Phe Leu Gln Asp Val Ser
450                 455                 460
Ala Ser Ala Lys Ser Leu Gln Glu Leu Leu Ser Ala His Ser Leu Ser
465                 470                 475                 480
Ser Trp Gly Ala Glu Val Lys Val Glu Pro Gly Glu Val Val Val Pro
                    485                 490                 495
Lys Gly Lys Ser Ala Ala Pro Ser Lys Lys Ser Lys Gly Ala Val Lys
                500                 505                 510
Glu Glu Gly Val Asn Lys Ser Glu Lys Arg Met Lys Leu Thr Leu Lys
            515                 520                 525
Gly Gly Ala Ala Val Asp Pro Asp Ser Gly Leu Glu His Ser Ala His
        530                 535                 540
Val Leu Glu Lys Gly Gly Lys Val Phe Ser Ala Thr Leu Gly Leu Val
545                 550                 555                 560
Asp Ile Val Lys Gly Thr Asn Ser Tyr Tyr Lys Leu Gln Leu Leu Glu
                    565                 570                 575
Ser Asp Lys Glu Ser Arg Tyr Trp Ile Phe Arg Ser Trp Gly Arg Val
                580                 585                 590
Gly Thr Val Ile Gly Ser Asn Lys Leu Glu Gln Met Pro Ser Lys Glu
            595                 600                 605
Asp Ala Val Glu His Phe Met Lys Leu Tyr Glu Glu Lys Thr Gly Asn
        610                 615                 620
Ala Trp His Ser Lys Asn Phe Thr Lys Tyr Pro Lys Lys Phe Tyr Pro
625                 630                 635                 640
Leu Glu Ile Asp Tyr Gly Gln Asp Glu Glu Ala Val Lys Lys Leu Ala
                    645                 650                 655
Val Lys Pro Gly Thr Lys Ser Lys Leu Pro Lys Pro Val Gln Glu Leu
                660                 665                 670
Val Gly Met Ile Phe Asp Val Glu Ser Met Lys Lys Ala Leu Val Glu
            675                 680                 685
Tyr Glu Ile Asp Leu Gln Lys Met Pro Leu Gly Lys Leu Ser Arg Arg
        690                 695                 700
Gln Ile Gln Ala Ala Tyr Ser Ile Leu Ser Glu Val Gln Gln Ala Val
705                 710                 715                 720
Ser Gln Gly Ser Ser Glu Ser Gln Ile Leu Asp Leu Ser Asn Arg Phe
                    725                 730                 735
Tyr Thr Leu Ile Pro His Asp Phe Gly Met Lys Lys Pro Pro Leu Leu
                740                 745                 750
Asn Asn Thr Asp Ser Val Gln Ala Lys Val Glu Met Leu Asp Asn Leu
            755                 760                 765
Leu Asp Ile Glu Val Ala Tyr Ser Leu Leu Arg Gly Gly Ser Asp Asp
        770                 775                 780
Ser Ser Lys Asp Pro Ile Asp Val Asn Tyr Glu Lys Leu Lys Thr Asp
785                 790                 795                 800
Ile Lys Val Val Asp Arg Asp Ser Glu Glu Ala Glu Val Ile Arg Lys
                    805                 810                 815
Tyr Val Lys Asn Thr His Ala Thr Thr His Asn Ala Tyr Asp Leu Glu
                820                 825                 830
```

-continued

```
Val Ile Asp Ile Phe Lys Ile Glu Arg Glu Gly Glu Ser Gln Arg Tyr
            835                 840                 845

Lys Pro Phe Arg Gln Leu His Asn Arg Leu Leu Trp His Gly Ser
850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
                    885                 890                 895

Phe Ala Asp Met Val Ser Lys Ser Ala Asn Tyr Cys His Thr Ser Gln
                900                 905                 910

Gly Asp Pro Ile Gly Leu Ile Leu Leu Gly Glu Val Ala Leu Gly Asn
            915                 920                 925

Met Tyr Glu Leu Lys His Ala Ser His Ile Ser Lys Leu Pro Lys Gly
        930                 935                 940

Lys His Ser Val Lys Gly Leu Gly Lys Thr Ala Pro Asp Pro Ser Ala
945                 950                 955                 960

Ser Ile Thr Leu Asp Gly Val Glu Val Pro Leu Gly Thr Gly Ile Pro
                965                 970                 975

Ser Gly Val Asn Asp Thr Cys Leu Leu Tyr Asn Glu Tyr Ile Val Tyr
                980                 985                 990

Asp Ile Ala Gln Val Asn Leu Lys Tyr Leu Leu Lys Leu Lys Phe Asn
            995                 1000                1005

Phe Lys Thr Ser Leu Trp
    1010
```

<210> SEQ ID NO 6
<211> LENGTH: 583
<212> TYPE: PRT
<213> ORGANISM: Homo sapiens

<400> SEQUENCE: 6

```
Met Ala Ala Arg Arg Arg Arg Ser Thr Gly Gly Gly Arg Ala Arg Ala
1               5                   10                  15

Leu Asn Glu Ser Lys Arg Val Asn Asn Gly Asn Thr Ala Pro Glu Asp
            20                  25                  30

Ser Ser Pro Ala Lys Lys Thr Arg Arg Cys Gln Arg Gln Glu Ser Lys
        35                  40                  45

Lys Met Pro Val Ala Gly Gly Lys Ala Asn Lys Asp Arg Thr Glu Asp
    50                  55                  60

Lys Gln Asp Gly Met Pro Gly Arg Ser Trp Ala Ser Lys Arg Val Ser
65                  70                  75                  80

Glu Ser Val Lys Ala Leu Leu Leu Lys Gly Lys Ala Pro Val Asp Pro
                85                  90                  95

Glu Cys Thr Ala Lys Val Gly Lys Ala His Val Tyr Cys Glu Gly Asn
            100                 105                 110

Asp Val Tyr Asp Val Met Leu Asn Gln Thr Asn Leu Gln Phe Asn Asn
        115                 120                 125

Asn Lys Tyr Tyr Leu Ile Gln Leu Leu Glu Asp Asp Ala Gln Arg Asn
    130                 135                 140

Phe Ser Val Trp Met Arg Trp Gly Arg Val Gly Lys Met Gly Gln His
145                 150                 155                 160

Ser Leu Val Ala Cys Ser Gly Asn Leu Asn Lys Ala Lys Glu Ile Phe
                165                 170                 175

Gln Lys Lys Phe Leu Asp Lys Thr Lys Asn Asn Trp Glu Asp Arg Glu
            180                 185                 190
```

Lys Phe Glu Lys Val Pro Gly Lys Tyr Asp Met Leu Gln Met Asp Tyr
            195                 200                 205

Ala Thr Asn Thr Gln Asp Glu Glu Thr Lys Lys Glu Glu Ser Leu
    210                 215                 220

Lys Ser Pro Leu Lys Pro Glu Ser Gln Leu Asp Leu Arg Val Gln Glu
225                 230                 235                 240

Leu Ile Lys Leu Ile Cys Asn Val Gln Ala Met Glu Glu Met Met Met
                245                 250                 255

Glu Met Lys Tyr Asn Thr Lys Lys Ala Pro Leu Gly Lys Leu Thr Val
                260                 265                 270

Ala Gln Ile Lys Ala Gly Tyr Gln Ser Leu Lys Lys Ile Glu Asp Cys
            275                 280                 285

Ile Arg Ala Gly Gln His Gly Arg Ala Leu Met Glu Ala Cys Asn Glu
            290                 295                 300

Phe Tyr Thr Arg Ile Pro His Asp Phe Gly Leu Arg Thr Pro Pro Leu
305                 310                 315                 320

Ile Arg Thr Gln Lys Glu Leu Ser Glu Lys Ile Gln Leu Leu Glu Ala
                325                 330                 335

Leu Gly Asp Ile Glu Ile Ala Ile Lys Leu Val Lys Thr Glu Leu Gln
                340                 345                 350

Ser Pro Glu His Pro Leu Asp Gln His Tyr Arg Asn Leu His Cys Ala
            355                 360                 365

Leu Arg Pro Leu Asp His Glu Ser Tyr Glu Phe Lys Val Ile Ser Gln
    370                 375                 380

Tyr Leu Gln Ser Thr His Ala Pro Thr His Ser Asp Tyr Thr Met Thr
385                 390                 395                 400

Leu Leu Asp Leu Phe Glu Val Glu Lys Asp Gly Glu Lys Glu Ala Phe
                405                 410                 415

Arg Glu Asp Leu His Asn Arg Met Leu Leu Trp His Gly Ser Arg Met
                420                 425                 430

Ser Asn Trp Val Gly Ile Leu Ser His Gly Leu Arg Ile Ala Pro Pro
            435                 440                 445

Glu Ala Pro Ile Thr Gly Tyr Met Phe Gly Lys Gly Ile Tyr Phe Ala
    450                 455                 460

Asp Met Ser Ser Lys Ser Ala Asn Tyr Cys Phe Ala Ser Arg Leu Lys
465                 470                 475                 480

Asn Thr Gly Leu Leu Leu Leu Ser Glu Val Ala Leu Gly Gln Cys Asn
                485                 490                 495

Glu Leu Leu Glu Ala Asn Pro Lys Ala Glu Gly Leu Leu Gln Gly Lys
                500                 505                 510

His Ser Thr Lys Gly Leu Gly Lys Met Ala Pro Ser Ser Ala His Phe
            515                 520                 525

Val Thr Leu Asn Gly Ser Thr Val Pro Leu Gly Pro Ala Ser Asp Thr
    530                 535                 540

Gly Ile Leu Asn Pro Asp Gly Tyr Thr Leu Asn Tyr Asn Glu Tyr Ile
545                 550                 555                 560

Val Tyr Asn Pro Asn Gln Val Arg Met Arg Tyr Leu Leu Lys Val Gln
                565                 570                 575

Phe Asn Phe Leu Gln Leu Trp
            580

<210> SEQ ID NO 7
<211> LENGTH: 570

```
<212> TYPE: PRT
<213> ORGANISM: Homo sapiens

<400> SEQUENCE: 7

Met Ala Ala Arg Arg Arg Ser Thr Gly Gly Arg Ala Arg Ala
1               5                   10                  15

Leu Asn Glu Ser Lys Arg Val Asn Asn Gly Asn Thr Ala Pro Glu Asp
                20                  25                  30

Ser Ser Pro Ala Lys Lys Thr Arg Arg Cys Gln Arg Gln Glu Ser Lys
        35                  40                  45

Lys Met Pro Val Ala Gly Gly Lys Ala Asn Lys Asp Arg Thr Glu Asp
    50                  55                  60

Lys Gln Asp Glu Ser Val Lys Ala Leu Leu Leu Lys Gly Lys Ala Pro
65                  70                  75                  80

Val Asp Pro Glu Cys Thr Ala Lys Val Gly Lys Ala His Val Tyr Cys
                85                  90                  95

Glu Gly Asn Asp Val Tyr Asp Val Met Leu Asn Gln Thr Asn Leu Gln
                100                 105                 110

Phe Asn Asn Lys Tyr Tyr Leu Ile Gln Leu Leu Glu Asp Asp Ala
            115                 120                 125

Gln Arg Asn Phe Ser Val Trp Met Arg Trp Gly Arg Val Gly Lys Met
    130                 135                 140

Gly Gln His Ser Leu Val Ala Cys Ser Gly Asn Leu Asn Lys Ala Lys
145                 150                 155                 160

Glu Ile Phe Gln Lys Lys Phe Leu Asp Lys Thr Lys Asn Asn Trp Glu
                165                 170                 175

Asp Arg Glu Lys Phe Glu Lys Val Pro Gly Lys Tyr Asp Met Leu Gln
            180                 185                 190

Met Asp Tyr Ala Thr Asn Thr Gln Asp Glu Glu Thr Lys Lys Glu
    195                 200                 205

Glu Ser Leu Lys Ser Pro Leu Lys Pro Glu Ser Gln Leu Asp Leu Arg
    210                 215                 220

Val Gln Glu Leu Ile Lys Leu Ile Cys Asn Val Gln Ala Met Glu Glu
225                 230                 235                 240

Met Met Met Glu Met Lys Tyr Asn Thr Lys Lys Ala Pro Leu Gly Lys
                245                 250                 255

Leu Thr Val Ala Gln Ile Lys Ala Gly Tyr Gln Ser Leu Lys Lys Ile
                260                 265                 270

Glu Asp Cys Ile Arg Ala Gly Gln His Gly Arg Ala Leu Met Glu Ala
            275                 280                 285

Cys Asn Glu Phe Tyr Thr Arg Ile Pro His Asp Phe Gly Leu Arg Thr
    290                 295                 300

Pro Pro Leu Ile Arg Thr Gln Lys Glu Leu Ser Glu Lys Ile Gln Leu
305                 310                 315                 320

Leu Glu Ala Leu Gly Asp Ile Glu Ile Ala Ile Lys Leu Val Lys Thr
                325                 330                 335

Glu Leu Gln Ser Pro Glu His Pro Leu Asp Gln His Tyr Arg Asn Leu
            340                 345                 350

His Cys Ala Leu Arg Pro Leu Asp His Glu Ser Tyr Glu Phe Lys Val
    355                 360                 365

Ile Ser Gln Tyr Leu Gln Ser Thr His Ala Pro Thr His Ser Asp Tyr
    370                 375                 380

Thr Met Thr Leu Leu Asp Leu Phe Glu Val Glu Lys Asp Gly Glu Lys
385                 390                 395                 400
```

```
Glu Ala Phe Arg Glu Asp Leu His Asn Arg Met Leu Leu Trp His Gly
                405                 410                 415

Ser Arg Met Ser Asn Trp Val Gly Ile Leu Ser His Gly Leu Arg Ile
            420                 425                 430

Ala Pro Pro Glu Ala Pro Ile Thr Gly Tyr Met Phe Gly Lys Gly Ile
        435                 440                 445

Tyr Phe Ala Asp Met Ser Ser Lys Ser Ala Asn Tyr Cys Phe Ala Ser
    450                 455                 460

Arg Leu Lys Asn Thr Gly Leu Leu Leu Ser Glu Val Ala Leu Gly
465                 470                 475                 480

Gln Cys Asn Glu Leu Leu Glu Ala Asn Pro Lys Ala Glu Gly Leu Leu
                485                 490                 495

Gln Gly Lys His Ser Thr Lys Gly Leu Gly Lys Met Ala Pro Ser Ser
            500                 505                 510

Ala His Phe Val Thr Leu Asn Gly Ser Thr Val Pro Leu Gly Pro Ala
        515                 520                 525

Ser Asp Thr Gly Ile Leu Asn Pro Asp Gly Tyr Thr Leu Asn Tyr Asn
    530                 535                 540

Glu Tyr Ile Val Tyr Asn Pro Asn Gln Val Arg Met Arg Tyr Leu Leu
545                 550                 555                 560

Lys Val Gln Phe Asn Phe Leu Gln Leu Trp
                565                 570

<210> SEQ ID NO 8
<211> LENGTH: 559
<212> TYPE: PRT
<213> ORGANISM: Mus musculus

<400> SEQUENCE: 8

Met Ala Pro Arg Arg Gln Arg Ser Gly Ser Gly Arg Arg Val Leu Asn
1               5                   10                  15

Glu Ala Lys Lys Val Asp Asn Gly Asn Lys Ala Thr Glu Asp Asp Ser
            20                  25                  30

Pro Pro Gly Lys Lys Met Arg Thr Cys Gln Arg Lys Gly Pro Met Ala
        35                  40                  45

Gly Gly Lys Asp Ala Asp Arg Thr Lys Asp Asn Arg Asp Ser Val Lys
    50                  55                  60

Thr Leu Leu Leu Lys Gly Lys Ala Pro Val Asp Pro Glu Cys Ala Ala
65                  70                  75                  80

Lys Leu Gly Lys Ala His Val Tyr Cys Glu Gly Asp Asp Val Tyr Asp
                85                  90                  95

Val Met Leu Asn Gln Thr Asn Leu Gln Phe Asn Asn Asn Lys Tyr Tyr
            100                 105                 110

Leu Ile Gln Leu Leu Glu Asp Ala Gln Arg Asn Phe Ser Val Trp
        115                 120                 125

Met Arg Trp Gly Arg Val Gly Lys Thr Gly Gln His Ser Leu Val Thr
    130                 135                 140

Cys Ser Gly Asp Leu Asn Lys Ala Lys Glu Ile Phe Gln Lys Phe
145                 150                 155                 160

Leu Asp Lys Thr Lys Asn Asn Trp Glu Asp Arg Glu Asn Phe Glu Lys
                165                 170                 175

Val Pro Gly Lys Tyr Asp Met Leu Gln Met Asp Tyr Ala Ala Ser Thr
            180                 185                 190

Gln Asp Glu Ser Lys Thr Lys Glu Glu Glu Thr Leu Lys Pro Glu Ser
```

```
                195                 200                 205
Gln Leu Asp Leu Arg Val Gln Glu Leu Lys Leu Ile Cys Asn Val
210                 215                 220

Gln Thr Met Glu Glu Met Met Ile Glu Met Lys Tyr Asp Thr Lys Arg
225                 230                 235                 240

Ala Pro Leu Gly Lys Leu Thr Val Ala Gln Ile Lys Ala Gly Tyr Gln
                245                 250                 255

Ser Leu Lys Lys Ile Glu Asp Cys Ile Arg Ala Gly Gln His Gly Arg
            260                 265                 270

Ala Leu Val Glu Ala Cys Asn Glu Phe Tyr Thr Arg Ile Pro His Asp
        275                 280                 285

Phe Gly Leu Ser Ile Pro Pro Val Ile Arg Thr Glu Lys Glu Leu Ser
290                 295                 300

Asp Lys Val Lys Leu Leu Glu Ala Leu Gly Asp Ile Glu Ile Ala Leu
305                 310                 315                 320

Lys Leu Val Lys Ser Glu Arg Gln Gly Leu Glu His Pro Leu Asp Gln
                325                 330                 335

His Tyr Arg Asn Leu His Cys Ala Leu Arg Pro Leu Asp His Glu Ser
            340                 345                 350

Asn Glu Phe Lys Val Ile Ser Gln Tyr Leu Gln Ser Thr His Ala Pro
        355                 360                 365

Thr His Lys Asp Tyr Thr Met Thr Leu Leu Asp Val Phe Glu Val Glu
370                 375                 380

Lys Glu Gly Glu Lys Glu Ala Phe Arg Glu Asp Leu Pro Asn Arg Met
385                 390                 395                 400

Leu Leu Trp His Gly Ser Arg Leu Ser Asn Trp Val Gly Ile Leu Ser
                405                 410                 415

His Gly Leu Arg Val Ala Pro Pro Glu Ala Pro Ile Thr Gly Tyr Met
            420                 425                 430

Phe Gly Lys Gly Ile Tyr Phe Ala Asp Met Ser Ser Lys Ser Ala Asn
        435                 440                 445

Tyr Cys Phe Ala Ser Arg Leu Lys Asn Thr Gly Leu Leu Leu Leu Ser
450                 455                 460

Glu Val Ala Leu Gly Gln Cys Asn Glu Leu Leu Glu Ala Asn Pro Lys
465                 470                 475                 480

Ala Gln Gly Leu Leu Arg Gly Lys His Ser Thr Lys Gly Met Gly Lys
                485                 490                 495

Met Ala Pro Ser Pro Ala His Phe Ile Thr Leu Asn Gly Ser Thr Val
            500                 505                 510

Pro Leu Gly Pro Ala Ser Asp Thr Gly Ile Leu Asn Pro Glu Gly Tyr
        515                 520                 525

Thr Leu Asn Tyr Asn Glu Phe Ile Val Tyr Ser Pro Asn Gln Val Arg
530                 535                 540

Met Arg Tyr Leu Leu Lys Ile Gln Phe Asn Phe Leu Gln Leu Trp
545                 550                 555

<210> SEQ ID NO 9
<211> LENGTH: 346
<212> TYPE: PRT
<213> ORGANISM: Homo sapiens

<400> SEQUENCE: 9

Met Val Gly Gly Gly Lys Arg Arg Pro Gly Gly Glu Gly Pro Gln
1               5                   10                  15
```

-continued

```
Cys Glu Lys Thr Thr Asp Val Lys Ser Lys Phe Cys Glu Ala Asp
            20                  25                  30

Val Ser Ser Asp Leu Arg Lys Glu Val Glu Asn His Tyr Lys Leu Ser
        35                  40                  45

Leu Pro Glu Asp Phe Tyr His Phe Trp Lys Phe Cys Glu Glu Leu Asp
 50                      55                  60

Pro Glu Lys Pro Ser Asp Ser Leu Ser Ala Ser Leu Gly Leu Gln Leu
 65                  70                  75                  80

Val Gly Pro Tyr Asp Ile Leu Ala Gly Lys His Lys Thr Lys Lys
                85                  90                  95

Ser Thr Gly Leu Asn Phe Asn Leu His Trp Arg Phe Tyr Tyr Asp Pro
            100                 105                 110

Pro Glu Phe Gln Thr Ile Ile Ile Gly Asp Asn Lys Thr Gln Tyr His
            115                 120                 125

Met Gly Tyr Phe Arg Asp Ser Pro Asp Glu Phe Pro Val Tyr Val Gly
        130                 135                 140

Ile Asn Glu Ala Lys Lys Asn Cys Ile Ile Val Pro Asn Gly Asp Asn
145                 150                 155                 160

Val Phe Ala Ala Val Lys Leu Phe Leu Thr Lys Lys Leu Arg Glu Ile
                165                 170                 175

Thr Asp Lys Lys Lys Ile Asn Leu Leu Lys Asn Ile Asp Glu Lys Leu
            180                 185                 190

Thr Glu Ala Ala Arg Glu Leu Gly Tyr Ser Leu Glu Gln Arg Thr Val
        195                 200                 205

Lys Met Lys Gln Arg Asp Lys Lys Val Val Thr Lys Thr Phe His Gly
210                 215                 220

Ala Gly Leu Val Val Pro Val Asp Lys Asn Asp Val Gly Tyr Arg Glu
225                 230                 235                 240

Leu Pro Glu Thr Asp Ala Asp Leu Lys Arg Ile Cys Lys Thr Ile Val
                245                 250                 255

Glu Ala Ala Ser Asp Glu Glu Arg Leu Lys Ala Phe Ala Pro Ile Gln
            260                 265                 270

Glu Met Met Thr Phe Val Gln Phe Ala Asn Asp Glu Cys Asp Tyr Gly
        275                 280                 285

Met Gly Leu Glu Leu Gly Met Asp Leu Phe Cys Tyr Gly Ser His Tyr
290                 295                 300

Phe His Lys Val Ala Gly Gln Leu Leu Pro Leu Ala Tyr Asn Leu Leu
305                 310                 315                 320

Lys Arg Asn Leu Phe Ala Glu Ile Ile Glu Glu His Leu Ala Asn Arg
                325                 330                 335

Ser Gln Glu Asn Ile Asp Gln Leu Ala Ala
            340                 345

<210> SEQ ID NO 10
<211> LENGTH: 346
<212> TYPE: PRT
<213> ORGANISM: Mus musculus

<400> SEQUENCE: 10

Met Val Gly Gly Gly Lys Arg Thr Ala Gly Ala Gly Pro Gln
1               5                   10                  15

Cys Glu Lys Thr Val Glu Val Lys Lys Ser Lys Phe Ser Glu Ala Asp
            20                  25                  30

Val Ser Ser Asp Leu Arg Lys Glu Val Glu Asn Leu Tyr Lys Leu Ser
        35                  40                  45
```

```
Leu Pro Glu Asp Phe Tyr His Phe Trp Lys Phe Cys Glu Glu Leu Asp
         50                  55                  60

Pro Glu Lys Pro Ala Asp Ala Leu Ala Thr Ser Leu Gly Leu Arg Leu
 65                  70                  75                  80

Val Gly Pro Tyr Asp Ile Leu Ala Gly Lys His Lys Met Lys Lys Lys
                 85                  90                  95

Pro Thr Gly Leu Asn Cys Asn Leu His Trp Arg Phe Tyr Tyr Asp Pro
                100                 105                 110

Pro Glu Phe Gln Thr Ile Ile Ile Gly Asp Asn Lys Thr Gln Tyr His
            115                 120                 125

Met Gly Tyr Phe Arg Asp Ser Pro Asp Glu Leu Pro Val Tyr Val Gly
        130                 135                 140

Thr Asn Glu Ala Lys Lys Asn Cys Ile Ile Gln Asn Gly Asp Asn
145                 150                 155                 160

Val Phe Ala Ala Ile Lys Leu Phe Leu Met Lys Lys Leu Lys Glu Val
                165                 170                 175

Thr Asp Arg Lys Lys Ile Ser Ile Leu Lys Asn Ile Asp Glu Lys Leu
            180                 185                 190

Thr Glu Ala Ala Arg Lys Leu Gly Tyr Ser Leu Glu Gln Arg Thr Val
        195                 200                 205

Lys Met Arg Gln Arg Asp Lys Lys Val Val Thr Lys Thr Phe His Gly
210                 215                 220

Ala Gly Leu Val Val Pro Val Asp Lys Asn Asp Val Gly Tyr Arg Glu
225                 230                 235                 240

Leu Pro Glu Thr Asp Ala Asp Leu Lys Arg Ile Cys Lys Ala Val Val
                245                 250                 255

Asp Ala Ala Ser Asp Glu Glu Arg Leu Lys Ala Phe Ala Pro Ile Gln
                260                 265                 270

Glu Met Met Thr Phe Val Gln Phe Ala Asn Asp Glu Cys Asp Tyr Gly
            275                 280                 285

Met Gly Leu Glu Leu Gly Met Asp Leu Phe Cys Tyr Gly Ser His Tyr
        290                 295                 300

Phe His Lys Val Ala Gly Gln Leu Leu Pro Leu Ala Tyr Asn Leu Leu
305                 310                 315                 320

Lys Arg Asp Leu Phe Ala Lys Ile Ile Glu Asp His Leu Ala Ser Arg
                325                 330                 335

Ser Glu Glu Asn Ile Asp Gln Leu Ala Gly
                340                 345

<210> SEQ ID NO 11
<211> LENGTH: 976
<212> TYPE: PRT
<213> ORGANISM: Homo sapiens

<400> SEQUENCE: 11

Met Asn Ala Gly Pro Gly Cys Glu Pro Cys Thr Lys Arg Pro Arg Trp
 1                   5                  10                  15

Gly Ala Ala Thr Thr Ser Pro Ala Ala Ser Asp Ala Arg Ser Phe Pro
                 20                  25                  30

Ser Arg Gln Arg Arg Val Leu Asp Pro Lys Asp Ala His Val Gln Phe
             35                  40                  45

Arg Val Pro Pro Ser Ser Pro Ala Cys Val Pro Gly Arg Ala Gly Gln
 50                  55                  60

His Arg Gly Ser Ala Thr Ser Leu Val Phe Lys Gln Lys Thr Ile Thr
```

```
                    65                  70                  75                  80
Ser Trp Met Asp Thr Lys Gly Ile Lys Thr Ala Glu Ser Glu Ser Leu
                            85                  90                  95

Asp Ser Lys Glu Asn Asn Thr Arg Ile Glu Ser Met Met Ser Ser
                100                 105                 110

Val Gln Lys Asp Asn Phe Tyr Gln His Asn Val Glu Lys Leu Glu Asn
            115                 120                 125

Val Ser Gln Leu Ser Leu Asp Lys Ser Pro Thr Glu Lys Ser Thr Gln
130                 135                 140

Tyr Leu Asn Gln His Gln Thr Ala Ala Met Cys Lys Trp Gln Asn Glu
145                 150                 155                 160

Gly Lys His Thr Glu Gln Leu Leu Glu Ser Glu Pro Gln Thr Val Thr
                165                 170                 175

Leu Val Pro Glu Gln Phe Ser Asn Ala Asn Ile Asp Arg Ser Pro Gln
                180                 185                 190

Asn Asp Asp His Ser Asp Thr Asp Ser Glu Glu Asn Arg Asp Asn Gln
            195                 200                 205

Gln Phe Leu Thr Thr Val Lys Leu Ala Asn Ala Lys Gln Thr Thr Glu
210                 215                 220

Asp Glu Gln Ala Arg Glu Ala Lys Ser His Gln Lys Cys Ser Lys Ser
225                 230                 235                 240

Cys Asp Pro Gly Glu Asp Cys Ala Ser Cys Gln Gln Asp Glu Ile Asp
                245                 250                 255

Val Val Pro Glu Ser Pro Leu Ser Asp Val Gly Ser Glu Asp Val Gly
                260                 265                 270

Thr Gly Pro Lys Asn Asp Asn Lys Leu Thr Arg Gln Glu Ser Cys Leu
            275                 280                 285

Gly Asn Ser Pro Pro Phe Glu Lys Glu Ser Glu Pro Glu Ser Pro Met
            290                 295                 300

Asp Val Asp Asn Ser Lys Asn Ser Cys Gln Asp Ser Glu Ala Asp Glu
305                 310                 315                 320

Glu Thr Ser Pro Gly Phe Asp Glu Gln Glu Asp Gly Ser Ser Ser Gln
                325                 330                 335

Thr Ala Asn Lys Pro Ser Arg Phe Gln Ala Arg Asp Ala Asp Ile Glu
            340                 345                 350

Phe Arg Lys Arg Tyr Ser Thr Lys Gly Gly Glu Val Arg Leu His Phe
            355                 360                 365

Gln Phe Glu Gly Gly Glu Ser Arg Thr Gly Met Asn Asp Leu Asn Ala
            370                 375                 380

Lys Leu Pro Gly Asn Ile Ser Ser Leu Asn Val Glu Cys Arg Asn Ser
385                 390                 395                 400

Lys Gln His Gly Lys Lys Asp Ser Lys Ile Thr Asp His Phe Met Arg
                405                 410                 415

Leu Pro Lys Ala Glu Asp Arg Arg Lys Glu Gln Trp Glu Thr Lys His
                420                 425                 430

Gln Arg Thr Glu Arg Lys Ile Pro Lys Tyr Val Pro Pro His Leu Ser
            435                 440                 445

Pro Asp Lys Lys Trp Leu Gly Thr Pro Ile Glu Met Arg Arg Met
450                 455                 460

Pro Arg Cys Gly Ile Arg Leu Pro Leu Leu Arg Pro Ser Ala Asn His
465                 470                 475                 480

Thr Val Thr Ile Arg Val Asp Leu Leu Arg Ala Gly Glu Val Pro Lys
                485                 490                 495
```

```
Pro Phe Pro Thr His Tyr Lys Asp Leu Trp Asp Asn Lys His Val Lys
            500                 505                 510

Met Pro Cys Ser Glu Gln Asn Leu Tyr Pro Val Glu Asp Glu Asn Gly
            515                 520                 525

Glu Arg Thr Ala Gly Ser Arg Trp Glu Leu Ile Gln Thr Ala Leu Leu
        530                 535                 540

Asn Lys Phe Thr Arg Pro Gln Asn Leu Lys Asp Ala Ile Leu Lys Tyr
545                 550                 555                 560

Asn Val Ala Tyr Ser Lys Lys Trp Asp Phe Thr Ala Leu Ile Asp Phe
                565                 570                 575

Trp Asp Lys Val Leu Glu Glu Ala Glu Ala Gln His Leu Tyr Gln Ser
            580                 585                 590

Ile Leu Pro Asp Met Val Lys Ile Ala Leu Cys Leu Pro Asn Ile Cys
        595                 600                 605

Thr Gln Pro Ile Pro Leu Leu Lys Gln Lys Met Asn His Ser Ile Thr
    610                 615                 620

Met Ser Gln Glu Gln Ile Ala Ser Leu Leu Ala Asn Ala Phe Phe Cys
625                 630                 635                 640

Thr Phe Pro Arg Arg Asn Ala Lys Met Lys Ser Glu Tyr Ser Ser Tyr
                645                 650                 655

Pro Asp Ile Asn Phe Asn Arg Leu Phe Glu Gly Arg Ser Ser Arg Lys
            660                 665                 670

Pro Glu Lys Leu Lys Thr Leu Phe Cys Tyr Phe Arg Arg Val Thr Glu
        675                 680                 685

Lys Lys Pro Thr Gly Leu Val Thr Phe Thr Arg Gln Ser Leu Glu Asp
    690                 695                 700

Phe Pro Glu Trp Glu Arg Cys Glu Lys Pro Leu Thr Arg Leu His Val
705                 710                 715                 720

Thr Tyr Glu Gly Thr Ile Glu Glu Asn Gly Gln Gly Met Leu Gln Val
                725                 730                 735

Asp Phe Ala Asn Arg Phe Val Gly Gly Val Thr Ser Ala Gly Leu
            740                 745                 750

Val Gln Glu Glu Ile Arg Phe Leu Ile Asn Pro Glu Leu Ile Ile Ser
        755                 760                 765

Arg Leu Phe Thr Glu Val Leu Asp His Asn Glu Cys Leu Ile Ile Thr
    770                 775                 780

Gly Thr Glu Gln Tyr Ser Glu Tyr Thr Gly Tyr Ala Glu Thr Tyr Arg
785                 790                 795                 800

Trp Ser Arg Ser His Glu Asp Gly Ser Glu Arg Asp Trp Gln Arg
                805                 810                 815

Arg Cys Thr Glu Ile Val Ala Ile Asp Ala Leu His Phe Arg Arg Tyr
            820                 825                 830

Leu Asp Gln Phe Val Pro Glu Lys Met Arg Arg Glu Leu Asn Lys Ala
        835                 840                 845

Tyr Cys Gly Phe Leu Arg Pro Gly Val Ser Ser Glu Asn Leu Ser Ala
    850                 855                 860

Val Ala Thr Gly Asn Trp Gly Cys Gly Ala Phe Gly Gly Asp Ala Arg
865                 870                 875                 880

Leu Lys Ala Leu Ile Gln Ile Leu Ala Ala Ala Ala Glu Arg Asp
                885                 890                 895

Val Val Tyr Phe Thr Phe Gly Asp Ser Glu Leu Met Arg Asp Ile Tyr
            900                 905                 910
```

```
Ser Met His Ile Phe Leu Thr Glu Arg Lys Leu Thr Val Gly Asp Val
            915                 920                 925

Tyr Lys Leu Leu Leu Arg Tyr Tyr Asn Glu Glu Cys Arg Asn Cys Ser
            930                 935                 940

Thr Pro Gly Pro Asp Ile Lys Leu Tyr Pro Phe Ile Tyr His Ala Val
945                 950                 955                 960

Glu Ser Cys Ala Glu Thr Ala Asp His Ser Gly Gln Arg Thr Gly Thr
                965                 970                 975

<210> SEQ ID NO 12
<211> LENGTH: 894
<212> TYPE: PRT
<213> ORGANISM: Homo sapiens

<400> SEQUENCE: 12

Met Asp Thr Lys Gly Ile Lys Thr Ala Glu Ser Glu Ser Leu Asp Ser
1               5                   10                  15

Lys Glu Asn Asn Thr Arg Ile Glu Ser Met Met Ser Ser Val Gln
            20                  25                  30

Lys Asp Asn Phe Tyr Gln His Asn Val Glu Lys Leu Glu Asn Val Ser
            35                  40                  45

Gln Leu Ser Leu Asp Lys Ser Pro Thr Glu Lys Ser Thr Gln Tyr Leu
    50                  55                  60

Asn Gln His Gln Thr Ala Ala Met Cys Lys Trp Gln Asn Glu Gly Lys
65                  70                  75                  80

His Thr Glu Gln Leu Leu Glu Ser Glu Pro Gln Thr Val Thr Leu Val
                85                  90                  95

Pro Glu Gln Phe Ser Asn Ala Asn Ile Asp Arg Ser Pro Gln Asn Asp
            100                 105                 110

Asp His Ser Asp Thr Asp Ser Glu Glu Asn Arg Asp Asn Gln Gln Phe
            115                 120                 125

Leu Thr Thr Val Lys Leu Ala Asn Ala Lys Gln Thr Thr Glu Asp Glu
    130                 135                 140

Gln Ala Arg Glu Ala Lys Ser His Gln Lys Cys Ser Lys Ser Cys Asp
145                 150                 155                 160

Pro Gly Glu Asp Cys Ala Ser Cys Gln Gln Asp Glu Ile Asp Val Val
                165                 170                 175

Pro Glu Ser Pro Leu Ser Asp Val Gly Ser Glu Asp Val Gly Thr Gly
            180                 185                 190

Pro Lys Asn Asp Asn Lys Leu Thr Arg Gln Glu Ser Cys Leu Gly Asn
            195                 200                 205

Ser Pro Pro Phe Glu Lys Glu Ser Glu Pro Glu Ser Pro Met Asp Val
    210                 215                 220

Asp Asn Ser Lys Asn Ser Cys Gln Asp Ser Glu Ala Asp Glu Glu Thr
225                 230                 235                 240

Ser Pro Gly Phe Asp Glu Gln Glu Asp Gly Ser Ser Ser Gln Thr Ala
                245                 250                 255

Asn Lys Pro Ser Arg Phe Gln Ala Arg Asp Ala Asp Ile Glu Phe Arg
            260                 265                 270

Lys Arg Tyr Ser Thr Lys Gly Gly Glu Val Arg Leu His Phe Gln Phe
            275                 280                 285

Glu Gly Gly Glu Ser Arg Thr Gly Met Asn Asp Leu Asn Ala Lys Leu
    290                 295                 300

Pro Gly Asn Ile Ser Ser Leu Asn Val Glu Cys Arg Asn Ser Lys Gln
305                 310                 315                 320
```

```
His Gly Lys Lys Asp Ser Lys Ile Thr Asp His Phe Met Arg Leu Pro
            325                 330                 335

Lys Ala Glu Asp Arg Arg Lys Glu Gln Trp Glu Thr Lys His Gln Arg
            340                 345                 350

Thr Glu Arg Lys Ile Pro Lys Tyr Val Pro Pro His Leu Ser Pro Asp
            355                 360                 365

Lys Lys Trp Leu Gly Thr Pro Ile Glu Glu Met Arg Arg Met Pro Arg
            370                 375                 380

Cys Gly Ile Arg Leu Pro Leu Leu Arg Pro Ser Ala Asn His Thr Val
385                 390                 395                 400

Thr Ile Arg Val Asp Leu Leu Arg Ala Gly Glu Val Pro Lys Pro Phe
            405                 410                 415

Pro Thr His Tyr Lys Asp Leu Trp Asp Asn Lys His Val Lys Met Pro
            420                 425                 430

Cys Ser Glu Gln Asn Leu Tyr Pro Val Glu Asp Glu Asn Gly Glu Arg
            435                 440                 445

Thr Ala Gly Ser Arg Trp Glu Leu Ile Gln Thr Ala Leu Leu Asn Lys
            450                 455                 460

Phe Thr Arg Pro Gln Asn Leu Lys Asp Ala Ile Leu Lys Tyr Asn Val
465                 470                 475                 480

Ala Tyr Ser Lys Lys Trp Asp Phe Thr Ala Leu Ile Asp Phe Trp Asp
            485                 490                 495

Lys Val Leu Glu Glu Ala Glu Ala Gln His Leu Tyr Gln Ser Ile Leu
            500                 505                 510

Pro Asp Met Val Lys Ile Ala Leu Cys Leu Pro Asn Ile Cys Thr Gln
            515                 520                 525

Pro Ile Pro Leu Leu Lys Gln Lys Met Asn His Ser Ile Thr Met Ser
            530                 535                 540

Gln Glu Gln Ile Ala Ser Leu Leu Ala Asn Ala Phe Phe Cys Thr Phe
545                 550                 555                 560

Pro Arg Arg Asn Ala Lys Met Lys Ser Glu Tyr Ser Ser Tyr Pro Asp
            565                 570                 575

Ile Asn Phe Asn Arg Leu Phe Glu Gly Arg Ser Ser Arg Lys Pro Glu
            580                 585                 590

Lys Leu Lys Thr Leu Phe Cys Tyr Phe Arg Arg Val Thr Glu Lys Lys
            595                 600                 605

Pro Thr Gly Leu Val Thr Phe Thr Arg Gln Ser Leu Glu Asp Phe Pro
            610                 615                 620

Glu Trp Glu Arg Cys Glu Lys Pro Leu Thr Arg Leu His Val Thr Tyr
625                 630                 635                 640

Glu Gly Thr Ile Glu Glu Asn Gly Gln Gly Met Leu Gln Val Asp Phe
            645                 650                 655

Ala Asn Arg Phe Val Gly Gly Val Thr Ser Ala Gly Leu Val Gln
            660                 665                 670

Glu Glu Ile Arg Phe Leu Ile Asn Pro Glu Leu Ile Ile Ser Arg Leu
            675                 680                 685

Phe Thr Glu Val Leu Asp His Asn Glu Cys Leu Ile Ile Thr Gly Thr
            690                 695                 700

Glu Gln Tyr Ser Glu Tyr Thr Gly Tyr Ala Glu Thr Tyr Arg Trp Ser
705                 710                 715                 720

Arg Ser His Glu Asp Gly Ser Glu Arg Asp Asp Trp Gln Arg Arg Cys
            725                 730                 735
```

```
Thr Glu Ile Val Ala Ile Asp Ala Leu His Phe Arg Arg Tyr Leu Asp
            740                 745                 750

Gln Phe Val Pro Glu Lys Met Arg Arg Glu Leu Asn Lys Ala Tyr Cys
        755                 760                 765

Gly Phe Leu Arg Pro Gly Val Ser Ser Glu Asn Leu Ser Ala Val Ala
    770                 775                 780

Thr Gly Asn Trp Gly Cys Gly Ala Phe Gly Gly Asp Ala Arg Leu Lys
785                 790                 795                 800

Ala Leu Ile Gln Ile Leu Ala Ala Ala Ala Glu Arg Asp Val Val
                805                 810                 815

Tyr Phe Thr Phe Gly Asp Ser Glu Leu Met Arg Asp Ile Tyr Ser Met
            820                 825                 830

His Ile Phe Leu Thr Glu Arg Lys Leu Thr Val Gly Asp Val Tyr Lys
            835                 840                 845

Leu Leu Leu Arg Tyr Tyr Asn Glu Glu Cys Arg Asn Cys Ser Thr Pro
        850                 855                 860

Gly Pro Asp Ile Lys Leu Tyr Pro Phe Ile Tyr His Ala Val Glu Ser
865                 870                 875                 880

Cys Ala Glu Thr Ala Asp His Ser Gly Gln Arg Thr Gly Thr
                885                 890

<210> SEQ ID NO 13
<211> LENGTH: 868
<212> TYPE: PRT
<213> ORGANISM: Homo sapiens

<400> SEQUENCE: 13

Met Met Ser Ser Val Gln Lys Asp Asn Phe Tyr Gln His Asn Val Glu
1               5                   10                  15

Lys Leu Glu Asn Val Ser Gln Leu Ser Leu Asp Lys Ser Pro Thr Glu
            20                  25                  30

Lys Ser Thr Gln Tyr Leu Asn Gln His Gln Thr Ala Ala Met Cys Lys
        35                  40                  45

Trp Gln Asn Glu Gly Lys His Thr Glu Gln Leu Leu Glu Ser Glu Pro
    50                  55                  60

Gln Thr Val Thr Leu Val Pro Glu Gln Phe Ser Asn Ala Asn Ile Asp
65                  70                  75                  80

Arg Ser Pro Gln Asn Asp Asp His Ser Asp Thr Asp Ser Glu Glu Asn
                85                  90                  95

Arg Asp Asn Gln Gln Phe Leu Thr Thr Val Lys Leu Ala Asn Ala Lys
            100                 105                 110

Gln Thr Thr Glu Asp Glu Gln Ala Arg Glu Ala Lys Ser His Gln Lys
        115                 120                 125

Cys Ser Lys Ser Cys Asp Pro Gly Glu Asp Cys Ala Ser Cys Gln Gln
    130                 135                 140

Asp Glu Ile Asp Val Val Pro Glu Ser Pro Leu Ser Asp Val Gly Ser
145                 150                 155                 160

Glu Asp Val Gly Thr Gly Pro Lys Asn Asp Asn Lys Leu Thr Arg Gln
                165                 170                 175

Glu Ser Cys Leu Gly Asn Ser Pro Pro Phe Lys Glu Ser Glu Pro
            180                 185                 190

Glu Ser Pro Met Asp Val Asp Asn Ser Lys Asn Ser Cys Gln Asp Ser
        195                 200                 205

Glu Ala Asp Glu Glu Thr Ser Pro Gly Phe Asp Glu Gln Glu Asp Gly
    210                 215                 220
```

-continued

Ser Ser Ser Gln Thr Ala Asn Lys Pro Ser Arg Phe Gln Ala Arg Asp
225                 230                 235                 240

Ala Asp Ile Glu Phe Arg Lys Arg Tyr Ser Thr Lys Gly Gly Glu Val
            245                 250                 255

Arg Leu His Phe Gln Phe Glu Gly Gly Glu Ser Arg Thr Gly Met Asn
        260                 265                 270

Asp Leu Asn Ala Lys Leu Pro Gly Asn Ile Ser Ser Leu Asn Val Glu
    275                 280                 285

Cys Arg Asn Ser Lys Gln His Gly Lys Lys Asp Ser Lys Ile Thr Asp
290                 295                 300

His Phe Met Arg Leu Pro Lys Ala Glu Asp Arg Arg Lys Glu Gln Trp
305                 310                 315                 320

Glu Thr Lys His Gln Arg Thr Glu Arg Lys Ile Pro Lys Tyr Val Pro
            325                 330                 335

Pro His Leu Ser Pro Asp Lys Lys Trp Leu Gly Thr Pro Ile Glu Glu
        340                 345                 350

Met Arg Arg Met Pro Arg Cys Gly Ile Arg Leu Pro Leu Leu Arg Pro
    355                 360                 365

Ser Ala Asn His Thr Val Thr Ile Arg Val Asp Leu Leu Arg Ala Gly
370                 375                 380

Glu Val Pro Lys Pro Phe Pro Thr His Tyr Lys Asp Leu Trp Asp Asn
385                 390                 395                 400

Lys His Val Lys Met Pro Cys Ser Glu Gln Asn Leu Tyr Pro Val Glu
            405                 410                 415

Asp Glu Asn Gly Glu Arg Thr Ala Gly Ser Arg Trp Glu Leu Ile Gln
        420                 425                 430

Thr Ala Leu Leu Asn Lys Phe Thr Arg Pro Gln Asn Leu Lys Asp Ala
    435                 440                 445

Ile Leu Lys Tyr Asn Val Ala Tyr Ser Lys Lys Trp Asp Phe Thr Ala
450                 455                 460

Leu Ile Asp Phe Trp Asp Lys Val Leu Glu Glu Ala Glu Ala Gln His
465                 470                 475                 480

Leu Tyr Gln Ser Ile Leu Pro Asp Met Val Lys Ile Ala Leu Cys Leu
            485                 490                 495

Pro Asn Ile Cys Thr Gln Pro Ile Pro Leu Leu Lys Gln Lys Met Asn
        500                 505                 510

His Ser Ile Thr Met Ser Gln Glu Gln Ile Ala Ser Leu Leu Ala Asn
    515                 520                 525

Ala Phe Phe Cys Thr Phe Pro Arg Arg Asn Ala Lys Met Lys Ser Glu
530                 535                 540

Tyr Ser Ser Tyr Pro Asp Ile Asn Phe Asn Arg Leu Phe Glu Gly Arg
545                 550                 555                 560

Ser Ser Arg Lys Pro Glu Lys Leu Lys Thr Leu Phe Cys Tyr Phe Arg
            565                 570                 575

Arg Val Thr Glu Lys Lys Pro Thr Gly Leu Val Thr Phe Thr Arg Gln
        580                 585                 590

Ser Leu Glu Asp Phe Pro Glu Trp Glu Arg Cys Glu Lys Pro Leu Thr
    595                 600                 605

Arg Leu His Val Thr Tyr Glu Gly Thr Ile Glu Glu Asn Gly Gln Gly
610                 615                 620

Met Leu Gln Val Asp Phe Ala Asn Arg Phe Val Gly Gly Gly Val Thr
625                 630                 635                 640

```
Ser Ala Gly Leu Val Gln Glu Glu Ile Arg Phe Leu Ile Asn Pro Glu
            645                 650                 655

Leu Ile Ile Ser Arg Leu Phe Thr Glu Val Leu Asp His Asn Glu Cys
        660                 665                 670

Leu Ile Ile Thr Gly Thr Glu Gln Tyr Ser Glu Tyr Thr Gly Tyr Ala
        675                 680                 685

Glu Thr Tyr Arg Trp Ser Arg Ser His Glu Asp Gly Ser Glu Arg Asp
    690                 695                 700

Asp Trp Gln Arg Arg Cys Thr Glu Ile Val Ala Ile Asp Ala Leu His
705                 710                 715                 720

Phe Arg Arg Tyr Leu Asp Gln Phe Val Pro Glu Lys Met Arg Arg Glu
                725                 730                 735

Leu Asn Lys Ala Tyr Cys Gly Phe Leu Arg Pro Gly Val Ser Ser Glu
            740                 745                 750

Asn Leu Ser Ala Val Ala Thr Gly Asn Trp Gly Cys Gly Ala Phe Gly
        755                 760                 765

Gly Asp Ala Arg Leu Lys Ala Leu Ile Gln Ile Leu Ala Ala Ala Ala
    770                 775                 780

Ala Glu Arg Asp Val Val Tyr Phe Thr Phe Gly Asp Ser Glu Leu Met
785                 790                 795                 800

Arg Asp Ile Tyr Ser Met His Ile Phe Leu Thr Glu Arg Lys Leu Thr
                805                 810                 815

Val Gly Asp Val Tyr Lys Leu Leu Leu Arg Tyr Tyr Asn Glu Glu Cys
            820                 825                 830

Arg Asn Cys Ser Thr Pro Gly Pro Asp Ile Lys Leu Tyr Pro Phe Ile
        835                 840                 845

Tyr His Ala Val Glu Ser Cys Ala Glu Thr Ala Asp His Ser Gly Gln
    850                 855                 860

Arg Thr Gly Thr
865

<210> SEQ ID NO 14
<211> LENGTH: 969
<212> TYPE: PRT
<213> ORGANISM: Mus musculus

<400> SEQUENCE: 14

Met Ser Ala Gly Pro Gly Trp Glu Pro Cys Thr Lys Arg Pro Arg Trp
1               5                   10                  15

Gly Ala Ala Gly Thr Ser Ala Pro Thr Ala Ser Asp Ser Arg Ser Phe
            20                  25                  30

Pro Gly Arg Gln Arg Arg Val Leu Asp Pro Lys Asp Ala Pro Val Gln
        35                  40                  45

Phe Arg Val Pro Pro Ser Ser Pro Ala Cys Val Ser Gly Arg Ala Gly
    50                  55                  60

Pro His Arg Gly Asn Ala Thr Ser Phe Val Phe Lys Gln Lys Thr Ile
65                  70                  75                  80

Thr Thr Trp Met Asp Thr Lys Gly Pro Lys Thr Ala Glu Ser Glu Ser
                85                  90                  95

Lys Glu Asn Asn Asn Thr Arg Ile Asp Ser Met Met Ser Ser Val Gln
            100                 105                 110

Lys Asp Asn Phe Tyr Pro His Lys Val Glu Lys Leu Glu Asn Val Pro
        115                 120                 125

Gln Leu Asn Leu Asp Lys Ser Pro Thr Glu Lys Ser Ser Gln Tyr Leu
    130                 135                 140
```

-continued

```
Asn Gln Gln Gln Thr Ala Ser Val Cys Lys Trp Gln Asn Glu Gly Lys
145                 150                 155                 160

His Ala Glu Gln Leu Leu Ala Ser Glu Pro Pro Ala Gly Thr Pro Leu
                165                 170                 175

Pro Lys Gln Leu Ser Asn Ala Asn Ile Gly Gln Ser Pro His Thr Asp
            180                 185                 190

Asp His Ser Asp Thr Asp His Glu Glu Asp Arg Asp Asn Gln Gln Phe
        195                 200                 205

Leu Thr Pro Ile Lys Leu Ala Asn Thr Lys Pro Thr Val Gly Asp Gly
    210                 215                 220

Gln Ala Arg Ser Asn Cys Lys Cys Ser Gly Ser Arg Gln Ser Val Lys
225                 230                 235                 240

Asp Cys Thr Gly Cys Gln Gln Glu Glu Val Asp Val Leu Pro Glu Ser
                245                 250                 255

Pro Leu Ser Asp Val Gly Ala Glu Asp Ile Gly Thr Gly Pro Lys Asn
            260                 265                 270

Asp Asn Lys Leu Thr Gly Gln Glu Ser Ser Leu Gly Asp Ser Pro Pro
        275                 280                 285

Phe Glu Lys Glu Ser Glu Pro Glu Ser Pro Met Asp Val Asp Asn Ser
    290                 295                 300

Lys Asn Ser Cys Gln Asp Ser Glu Ala Asp Glu Glu Thr Ser Pro Val
305                 310                 315                 320

Phe Asp Glu Gln Asp Asp Arg Ser Ser Gln Thr Ala Asn Lys Leu Ser
                325                 330                 335

Ser Cys Gln Ala Arg Glu Ala Asp Gly Asp Leu Arg Lys Arg Tyr Leu
            340                 345                 350

Thr Lys Gly Ser Glu Val Arg Leu His Phe Gln Phe Glu Gly Glu Asn
        355                 360                 365

Asn Ala Gly Thr Ser Asp Leu Asn Ala Lys Pro Ser Gly Asn Ser Ser
    370                 375                 380

Ser Leu Asn Val Glu Cys Arg Ser Ser Lys Gln His Gly Lys Arg Asp
385                 390                 395                 400

Ser Lys Ile Thr Asp His Phe Met Arg Ile Ser Lys Ser Glu Asp Arg
                405                 410                 415

Arg Lys Glu Gln Cys Glu Val Arg His Gln Arg Thr Glu Arg Lys Ile
            420                 425                 430

Pro Lys Tyr Ile Pro Pro Asn Leu Pro Pro Glu Lys Lys Trp Leu Gly
        435                 440                 445

Thr Pro Ile Glu Glu Met Arg Lys Met Pro Arg Cys Gly Ile His Leu
    450                 455                 460

Pro Ser Leu Arg Pro Ser Ala Ser His Thr Val Thr Arg Val Asp
465                 470                 475                 480

Leu Leu Arg Ala Gly Glu Val Pro Lys Pro Phe Pro Thr His Tyr Lys
                485                 490                 495

Asp Leu Trp Asp Asn Lys His Val Lys Met Pro Cys Ser Glu Gln Asn
            500                 505                 510

Leu Tyr Pro Val Glu Asp Glu Asn Gly Glu Arg Thr Ala Gly Ser Arg
        515                 520                 525

Trp Glu Leu Ile Gln Thr Ala Leu Leu Asn Lys Phe Thr Arg Pro Gln
    530                 535                 540

Asn Leu Lys Asp Ala Ile Leu Lys Tyr Asn Val Ala Tyr Ser Lys Lys
545                 550                 555                 560
```

```
Trp Asp Phe Thr Ala Leu Val Asp Phe Trp Asp Lys Val Leu Glu Glu
            565                 570                 575

Ala Glu Ala Gln His Leu Tyr Gln Ser Ile Leu Pro Asp Met Val Lys
            580                 585                 590

Ile Ala Leu Cys Leu Pro Asn Ile Cys Thr Gln Pro Ile Pro Leu Leu
            595                 600                 605

Lys Gln Lys Met Asn His Ser Val Thr Met Ser Gln Glu Gln Ile Ala
            610                 615                 620

Ser Leu Leu Ala Asn Ala Phe Phe Cys Thr Phe Pro Arg Arg Asn Ala
625                 630                 635                 640

Lys Met Lys Ser Glu Tyr Ser Ser Tyr Pro Asp Ile Asn Phe Asn Arg
            645                 650                 655

Leu Phe Glu Gly Arg Ser Ser Arg Lys Pro Glu Lys Leu Lys Thr Leu
            660                 665                 670

Phe Cys Tyr Phe Arg Arg Val Thr Glu Lys Pro Thr Gly Leu Val
            675                 680                 685

Thr Phe Thr Arg Gln Ser Leu Glu Asp Phe Pro Glu Trp Glu Arg Cys
            690                 695                 700

Glu Lys Pro Leu Thr Arg Leu His Val Thr Tyr Glu Gly Thr Ile Glu
705                 710                 715                 720

Gly Asn Gly Arg Gly Met Leu Gln Val Asp Phe Ala Asn Arg Phe Val
            725                 730                 735

Gly Gly Gly Val Thr Gly Ala Gly Leu Val Gln Glu Glu Ile Arg Phe
            740                 745                 750

Leu Ile Asn Pro Glu Leu Ile Val Ser Arg Leu Phe Thr Glu Val Leu
            755                 760                 765

Asp His Asn Glu Cys Leu Ile Ile Thr Gly Thr Glu Gln Tyr Ser Glu
            770                 775                 780

Tyr Thr Gly Tyr Ala Glu Thr Tyr Arg Trp Ala Arg Ser His Glu Asp
785                 790                 795                 800

Gly Ser Glu Lys Asp Asp Trp Gln Arg Arg Cys Thr Glu Ile Val Ala
            805                 810                 815

Ile Asp Ala Leu His Phe Arg Arg Tyr Leu Asp Gln Phe Val Pro Glu
            820                 825                 830

Lys Val Arg Arg Glu Leu Asn Lys Ala Tyr Cys Gly Phe Leu Arg Pro
            835                 840                 845

Gly Val Pro Ser Glu Asn Leu Ser Ala Val Ala Thr Gly Asn Trp Gly
            850                 855                 860

Cys Gly Ala Phe Gly Gly Asp Ala Arg Leu Lys Ala Leu Ile Gln Ile
865                 870                 875                 880

Leu Ala Ala Ala Ala Glu Arg Asp Val Val Tyr Phe Thr Phe Gly
            885                 890                 895

Asp Ser Glu Leu Met Arg Asp Ile Tyr Ser Met His Thr Phe Leu Thr
            900                 905                 910

Glu Arg Lys Leu Asp Val Gly Lys Val Tyr Lys Leu Leu Leu Arg Tyr
            915                 920                 925

Tyr Asn Glu Glu Cys Arg Asn Cys Ser Thr Pro Gly Pro Asp Ile Lys
            930                 935                 940

Leu Tyr Pro Phe Ile Tyr His Ala Val Glu Ser Ser Ala Glu Thr Thr
945                 950                 955                 960

Asp Met Pro Gly Gln Lys Ala Gly Thr
            965
```

<210> SEQ ID NO 15
<211> LENGTH: 920
<212> TYPE: PRT
<213> ORGANISM: Mus musculus

<400> SEQUENCE: 15

| Met | Ser | Ala | Gly | Pro | Gly | Trp | Glu | Pro | Cys | Thr | Lys | Arg | Pro | Arg | Trp |
|---|---|---|---|---|---|---|---|---|---|---|---|---|---|---|---|
| 1 | | | | 5 | | | | | 10 | | | | | 15 | |

| Gly | Ala | Ala | Gly | Thr | Ser | Ala | Pro | Thr | Ala | Ser | Asp | Ser | Arg | Ser | Phe |
|---|---|---|---|---|---|---|---|---|---|---|---|---|---|---|---|
| | | | 20 | | | | | 25 | | | | | 30 | | |

| Pro | Gly | Arg | Gln | Arg | Arg | Val | Leu | Asp | Pro | Lys | Asp | Ala | Pro | Val | Gln |
|---|---|---|---|---|---|---|---|---|---|---|---|---|---|---|---|
| | | | 35 | | | | | 40 | | | | | 45 | | |

| Phe | Arg | Val | Pro | Pro | Ser | Ser | Pro | Ala | Cys | Val | Ser | Gly | Arg | Ala | Gly |
|---|---|---|---|---|---|---|---|---|---|---|---|---|---|---|---|
| | 50 | | | | | 55 | | | | | 60 | | | | |

| Pro | His | Arg | Gly | Asn | Ala | Thr | Ser | Phe | Val | Phe | Lys | Gln | Lys | Thr | Ile |
|---|---|---|---|---|---|---|---|---|---|---|---|---|---|---|---|
| 65 | | | | | 70 | | | | | 75 | | | | | 80 |

| Thr | Thr | Trp | Met | Asp | Thr | Lys | Gly | Pro | Lys | Thr | Ala | Glu | Ser | Glu | Ser |
|---|---|---|---|---|---|---|---|---|---|---|---|---|---|---|---|
| | | | | 85 | | | | | 90 | | | | | 95 | |

| Lys | Glu | Asn | Asn | Asn | Thr | Arg | Ile | Asp | Ser | Met | Met | Ser | Ser | Val | Gln |
|---|---|---|---|---|---|---|---|---|---|---|---|---|---|---|---|
| | | | 100 | | | | | 105 | | | | | 110 | | |

| Lys | Asp | Asn | Phe | Tyr | Pro | His | Lys | Val | Glu | Lys | Leu | Glu | Asn | Val | Pro |
|---|---|---|---|---|---|---|---|---|---|---|---|---|---|---|---|
| | | | 115 | | | | | 120 | | | | | 125 | | |

| Gln | Leu | Asn | Leu | Asp | Lys | Ser | Pro | Thr | Glu | Lys | Ser | Ser | Gln | Tyr | Leu |
|---|---|---|---|---|---|---|---|---|---|---|---|---|---|---|---|
| | 130 | | | | | 135 | | | | | 140 | | | | |

| Asn | Gln | Gln | Gln | Thr | Ala | Ser | Val | Cys | Lys | Trp | Gln | Asn | Glu | Gly | Lys |
|---|---|---|---|---|---|---|---|---|---|---|---|---|---|---|---|
| 145 | | | | | 150 | | | | | 155 | | | | | 160 |

| His | Ala | Glu | Gln | Leu | Leu | Ala | Ser | Glu | Pro | Pro | Ala | Gly | Thr | Pro | Leu |
|---|---|---|---|---|---|---|---|---|---|---|---|---|---|---|---|
| | | | | 165 | | | | | 170 | | | | | 175 | |

| Pro | Lys | Gln | Leu | Ser | Asn | Ala | Asn | Ile | Gly | Gln | Ser | Pro | His | Thr | Asp |
|---|---|---|---|---|---|---|---|---|---|---|---|---|---|---|---|
| | | | 180 | | | | | 185 | | | | | 190 | | |

| Asp | His | Ser | Asp | Thr | Asp | His | Glu | Glu | Asp | Arg | Asp | Asn | Gln | Gln | Phe |
|---|---|---|---|---|---|---|---|---|---|---|---|---|---|---|---|
| | | | 195 | | | | | 200 | | | | | 205 | | |

| Leu | Thr | Pro | Ile | Lys | Leu | Ala | Asn | Thr | Lys | Pro | Thr | Val | Gly | Asp | Gly |
|---|---|---|---|---|---|---|---|---|---|---|---|---|---|---|---|
| | 210 | | | | | 215 | | | | | 220 | | | | |

| Gln | Ala | Arg | Ser | Asn | Cys | Lys | Cys | Ser | Gly | Ser | Arg | Gln | Ser | Val | Lys |
|---|---|---|---|---|---|---|---|---|---|---|---|---|---|---|---|
| 225 | | | | | 230 | | | | | 235 | | | | | 240 |

| Asp | Cys | Thr | Gly | Cys | Gln | Gln | Glu | Glu | Val | Asp | Val | Leu | Pro | Glu | Ser |
|---|---|---|---|---|---|---|---|---|---|---|---|---|---|---|---|
| | | | | 245 | | | | | 250 | | | | | 255 | |

| Pro | Leu | Ser | Asp | Val | Gly | Ala | Glu | Asp | Ile | Gly | Thr | Gly | Pro | Lys | Asn |
|---|---|---|---|---|---|---|---|---|---|---|---|---|---|---|---|
| | | | 260 | | | | | 265 | | | | | 270 | | |

| Asp | Asn | Lys | Leu | Thr | Gly | Gln | Glu | Ser | Ser | Leu | Gly | Asp | Ser | Pro | Pro |
|---|---|---|---|---|---|---|---|---|---|---|---|---|---|---|---|
| | | | 275 | | | | | 280 | | | | | 285 | | |

| Phe | Glu | Lys | Glu | Ser | Glu | Pro | Glu | Ser | Pro | Met | Asp | Val | Asp | Asn | Ser |
|---|---|---|---|---|---|---|---|---|---|---|---|---|---|---|---|
| | 290 | | | | | 295 | | | | | 300 | | | | |

| Lys | Asn | Ser | Cys | Gln | Asp | Ser | Glu | Ala | Asp | Glu | Glu | Thr | Ser | Pro | Val |
|---|---|---|---|---|---|---|---|---|---|---|---|---|---|---|---|
| 305 | | | | | 310 | | | | | 315 | | | | | 320 |

| Phe | Asp | Glu | Gln | Asp | Asp | Arg | Ser | Ser | Gln | Thr | Ala | Asn | Lys | Leu | Ser |
|---|---|---|---|---|---|---|---|---|---|---|---|---|---|---|---|
| | | | | 325 | | | | | 330 | | | | | 335 | |

| Ser | Cys | Gln | Ala | Arg | Glu | Ala | Asp | Gly | Asp | Leu | Arg | Lys | Arg | Tyr | Leu |
|---|---|---|---|---|---|---|---|---|---|---|---|---|---|---|---|
| | | | 340 | | | | | 345 | | | | | 350 | | |

| Thr | Lys | Gly | Ser | Glu | Val | Arg | Leu | His | Phe | Gln | Phe | Glu | Gly | Glu | Asn |
|---|---|---|---|---|---|---|---|---|---|---|---|---|---|---|---|
| | | | 355 | | | | | 360 | | | | | 365 | | |

| Asn | Ala | Gly | Thr | Ser | Asp | Leu | Asn | Ala | Lys | Pro | Ser | Gly | Asn | Ser | Ser |
|---|---|---|---|---|---|---|---|---|---|---|---|---|---|---|---|
| | | | 370 | | | | | 375 | | | | | 380 | | |

-continued

```
Ser Leu Asn Val Glu Cys Arg Ser Ser Lys Gln His Gly Lys Arg Asp
385                 390                 395                 400
Ser Lys Ile Thr Asp His Phe Met Arg Ile Ser Lys Ser Glu Asp Arg
            405                 410                 415
Arg Lys Glu Gln Cys Glu Val Arg His Gln Arg Thr Glu Arg Lys Ile
                420                 425                 430
Pro Lys Tyr Ile Pro Pro Asn Leu Pro Pro Glu Lys Lys Trp Leu Gly
            435                 440                 445
Thr Pro Ile Glu Glu Met Arg Lys Met Pro Arg Cys Gly Ile His Leu
    450                 455                 460
Pro Ser Leu Arg Pro Ser Ala Ser His Thr Val Thr Val Arg Val Asp
465                 470                 475                 480
Leu Leu Arg Ala Gly Glu Val Pro Lys Pro Phe Pro Thr His Tyr Lys
                485                 490                 495
Asp Leu Trp Asp Asn Lys His Val Lys Met Pro Cys Ser Glu Gln Asn
            500                 505                 510
Leu Tyr Pro Val Glu Asp Glu Asn Gly Glu Arg Thr Ala Gly Ser Arg
            515                 520                 525
Trp Glu Leu Ile Gln Thr Ala Leu Leu Asn Lys Phe Thr Arg Pro Gln
    530                 535                 540
Asn Leu Lys Asp Ala Ile Leu Lys Tyr Asn Val Ala Tyr Ser Lys Lys
545                 550                 555                 560
Trp Asp Phe Thr Ala Leu Val Asp Phe Trp Asp Lys Val Leu Glu Glu
                565                 570                 575
Ala Glu Ala Gln His Leu Tyr Gln Ser Ile Leu Pro Asp Met Val Lys
            580                 585                 590
Ile Ala Leu Cys Leu Pro Asn Ile Cys Thr Gln Pro Ile Pro Leu Leu
            595                 600                 605
Lys Gln Lys Met Asn His Ser Val Thr Met Ser Gln Glu Gln Ile Ala
    610                 615                 620
Ser Leu Leu Ala Asn Ala Phe Phe Cys Thr Phe Pro Arg Arg Asn Ala
625                 630                 635                 640
Lys Met Lys Ser Glu Tyr Ser Ser Tyr Pro Asp Ile Asn Phe Asn Arg
                645                 650                 655
Leu Phe Glu Gly Arg Ser Ser Arg Lys Pro Glu Lys Leu Lys Thr Leu
            660                 665                 670
Phe Cys Tyr Phe Arg Arg Val Thr Glu Lys Pro Thr Gly Leu Val
            675                 680                 685
Thr Phe Thr Arg Gln Ser Leu Glu Asp Phe Pro Glu Trp Glu Arg Cys
    690                 695                 700
Glu Lys Pro Leu Thr Arg Leu His Val Thr Tyr Glu Gly Thr Ile Glu
705                 710                 715                 720
Gly Asn Gly Arg Gly Met Leu Gln Val Asp Phe Ala Asn Arg Phe Val
                725                 730                 735
Gly Gly Gly Val Thr Gly Ala Gly Leu Val Gln Glu Glu Ile Arg Phe
            740                 745                 750
Leu Ile Asn Pro Glu Leu Ile Val Ser Arg Leu Phe Thr Glu Val Leu
            755                 760                 765
Asp His Asn Glu Cys Leu Ile Ile Thr Gly Thr Glu Gln Tyr Ser Glu
    770                 775                 780
Tyr Thr Gly Tyr Ala Glu Thr Tyr Arg Trp Ala Arg Ser His Glu Asp
785                 790                 795                 800
Gly Ser Glu Lys Asp Asp Trp Gln Arg Arg Cys Thr Glu Ile Val Ala
```

```
                 805                 810                 815

Ile Asp Ala Leu His Phe Arg Arg Tyr Leu Asp Gln Phe Val Pro Glu
            820                 825                 830

Lys Val Arg Arg Glu Leu Asn Lys Ala Tyr Cys Gly Phe Leu Arg Pro
            835                 840                 845

Gly Val Pro Ser Glu Asn Leu Ser Ala Val Ala Thr Gly Asn Trp Gly
            850                 855                 860

Cys Gly Ala Phe Gly Gly Asp Ala Arg Leu Lys Ala Leu Ile Gln Ile
865                 870                 875                 880

Leu Ala Ala Ala Ala Glu Arg Asp Val Val Tyr Phe Thr Phe Gly
                885                 890                 895

Asp Ser Glu Leu Met Arg Asp Ile Tyr Ser Met His Thr Phe Leu Thr
            900                 905                 910

Glu Arg Lys Leu Asp Val Gly Glu
            915                 920

<210> SEQ ID NO 16
<211> LENGTH: 972
<212> TYPE: PRT
<213> ORGANISM: Rattus norvegicus

<400> SEQUENCE: 16

Met Ser Ala Gly Pro Gly Cys Glu Pro Cys Thr Lys Arg Pro Arg Trp
1               5                   10                  15

Gly Ala Ala Gly Thr Ser Ala Pro Thr Ala Ser Asp Ser Arg Ser Phe
            20                  25                  30

Pro Gly Arg Gln Lys Arg Val Leu Asp Pro Lys Asp Ala Pro Val Gln
        35                  40                  45

Phe Arg Val Pro Pro Ser Ser Ala Cys Val Ser Gly Arg Ala Gly
    50                  55                  60

Pro His Arg Gly Ser Val Thr Ser Phe Val Phe Lys Gln Lys Pro Ile
65                  70                  75                  80

Thr Thr Trp Met Asp Thr Lys Gly Pro Lys Thr Ala Glu Ser Glu Ser
                85                  90                  95

Lys Glu Asn Asn Asn Thr Arg Thr Asp Pro Met Met Ser Ser Val Gln
            100                 105                 110

Lys Asp Asn Phe Tyr Pro His Lys Val Glu Lys Leu Gly Asn Val Pro
        115                 120                 125

Gln Leu Asn Leu Asp Lys Ser Pro Thr Glu Lys Ser Thr Pro Tyr Leu
    130                 135                 140

Asn Gln Gln Gln Thr Ala Gly Val Cys Lys Trp His Ser Ala Gly Glu
145                 150                 155                 160

Arg Ala Glu Gln Leu Ser Ala Ser Glu Pro Ser Ala Val Thr Gln Ala
                165                 170                 175

Pro Lys Gln Leu Ser Asn Ala Asn Ile Asp Gln Ser Pro Pro Thr Asp
            180                 185                 190

Gly His Ser Asp Thr Asp His Glu Glu Asp Arg Asp Asn Gln Gln Phe
        195                 200                 205

Leu Thr Pro Val Lys Leu Ala Asn Ala Lys Gln Thr Val Gly Asp Gly
    210                 215                 220

Gln Ala Arg Ser Asn Cys Lys Cys Ser Ala Ser Cys Gln Cys Gly Gln
225                 230                 235                 240

Asp Cys Ala Gly Cys Gln Arg Glu Glu Ala Asp Val Ile Pro Glu Ser
                245                 250                 255
```

-continued

```
Pro Leu Ser Asp Val Gly Ala Glu Asp Ile Gly Thr Gly Ser Lys Asn
            260                 265                 270

Asp Asn Lys Leu Thr Gly Gln Glu Ser Gly Leu Gly Asp Ser Pro Pro
        275                 280                 285

Phe Glu Lys Glu Ser Glu Pro Glu Ser Pro Met Asp Val Asp Asn Ser
    290                 295                 300

Lys Thr Ser Cys Gln Asp Ser Glu Ala Asp Glu Ala Ser Pro Val
305                 310                 315                 320

Phe Asp Glu Gln Asp Gln Asp Arg Ser Ser Gln Thr Ala Asn
                325                 330                 335

Lys Leu Ser Ser Arg Gln Ala Arg Glu Val Asp Gly Asp Leu Arg Lys
            340                 345                 350

Arg Tyr Leu Thr Lys Gly Ser Glu Ile Arg Leu His Phe Gln Phe Glu
        355                 360                 365

Gly Gly Ser Asn Ala Gly Thr Ser Asp Leu Asn Ala Lys Pro Ser Gly
    370                 375                 380

Asn Ser Ser Ser Leu Asn Val Asp Gly Arg Ser Ser Lys Gln His Gly
385                 390                 395                 400

Lys Arg Asp Ser Lys Ile Thr Asp His Phe Val Arg Ile Pro Lys Ser
                405                 410                 415

Glu Asp Lys Arg Lys Glu Gln Cys Glu Val Arg His Gln Arg Ala Glu
            420                 425                 430

Arg Lys Ile Pro Lys Tyr Val Pro Asn Leu Pro Pro Asp Lys Lys
        435                 440                 445

Trp Leu Gly Thr Pro Ile Glu Glu Met Arg Lys Met Pro Arg Cys Gly
    450                 455                 460

Val Arg Leu Pro Leu Leu Arg Pro Ser Ala Ser His Thr Val Thr Val
465                 470                 475                 480

Arg Val Asp Leu Leu Arg Ala Gly Glu Val Pro Lys Pro Phe Pro Thr
                485                 490                 495

His Tyr Lys Asp Leu Trp Asp Asn Lys His Val Lys Met Pro Cys Ser
            500                 505                 510

Glu Gln Asn Leu Tyr Pro Val Glu Asp Glu Asn Gly Glu Arg Thr Ala
        515                 520                 525

Gly Ser Arg Trp Glu Leu Ile Gln Thr Ala Leu Leu Asn Lys Phe Thr
    530                 535                 540

Arg Pro Gln Asn Leu Lys Asp Ala Ile Leu Lys Tyr Asn Val Ala Tyr
545                 550                 555                 560

Ser Lys Lys Trp Asp Phe Thr Ala Leu Val Asp Phe Trp Asp Lys Val
                565                 570                 575

Leu Glu Glu Ala Glu Ala Gln His Leu Tyr Gln Ser Ile Leu Pro Asp
            580                 585                 590

Met Val Lys Ile Ala Leu Cys Leu Pro Asn Ile Cys Thr Gln Pro Ile
        595                 600                 605

Pro Leu Leu Lys Gln Lys Met Asn His Ser Val Thr Met Ser Gln Glu
    610                 615                 620

Gln Ile Ala Ser Leu Leu Ala Asn Ala Phe Phe Cys Thr Phe Pro Arg
625                 630                 635                 640

Arg Asn Ala Lys Met Lys Ser Glu Tyr Ser Ser Tyr Pro Asp Ile Asn
                645                 650                 655

Phe Asn Arg Leu Phe Glu Gly Arg Ser Ser Arg Lys Pro Glu Lys Leu
            660                 665                 670

Lys Thr Leu Phe Cys Tyr Phe Arg Arg Val Thr Glu Lys Lys Pro Thr
```

675                 680                 685

Gly Leu Val Thr Phe Thr Arg Gln Ser Leu Glu Asp Phe Pro Glu Trp
            690                 695                 700

Glu Arg Cys Asp Lys Pro Leu Thr Arg Leu His Val Thr Tyr Glu Gly
705                 710                 715                 720

Thr Ile Glu Gly Asn Gly Arg Gly Met Leu Gln Val Asp Phe Ala Asn
                725                 730                 735

Arg Phe Val Gly Gly Val Thr Gly Ala Gly Leu Val Gln Glu Glu
            740                 745                 750

Ile Arg Phe Leu Ile Asn Pro Glu Leu Ile Val Ser Arg Leu Phe Thr
            755                 760                 765

Glu Val Leu Asp His Asn Glu Cys Leu Ile Ile Thr Gly Thr Glu Gln
770                 775                 780

Tyr Ser Glu Tyr Thr Gly Tyr Ala Glu Thr Tyr Arg Trp Ala Arg Ser
785                 790                 795                 800

His Glu Asp Gly Ser Glu Lys Asp Asp Trp Gln Arg Cys Cys Thr Glu
                805                 810                 815

Ile Val Ala Ile Asp Ala Leu His Phe Arg Arg Tyr Leu Asp Gln Phe
            820                 825                 830

Val Pro Glu Lys Val Arg Arg Glu Leu Asn Lys Ala Tyr Cys Gly Phe
            835                 840                 845

Leu Arg Pro Gly Val Pro Pro Glu Asn Leu Ser Ala Val Ala Thr Gly
850                 855                 860

Asn Trp Gly Cys Gly Ala Phe Gly Gly Asp Ala Arg Leu Lys Ala Leu
865                 870                 875                 880

Ile Gln Leu Leu Ala Ala Ala Ala Glu Arg Asp Val Val Tyr Phe
                885                 890                 895

Thr Phe Gly Asp Ser Glu Leu Met Arg Asp Ile Tyr Ser Met His Thr
            900                 905                 910

Phe Leu Thr Glu Arg Lys Leu Asn Val Gly Lys Val Tyr Arg Leu Leu
            915                 920                 925

Leu Arg Tyr Tyr Arg Glu Glu Cys Arg Asp Cys Ser Ser Pro Gly Pro
930                 935                 940

Asp Thr Lys Leu Tyr Pro Phe Ile Tyr His Ala Ala Glu Ser Ser Ala
945                 950                 955                 960

Glu Thr Ser Asp Gln Pro Gly Gln Arg Thr Gly Thr
                965                 970

<210> SEQ ID NO 17
<211> LENGTH: 16
<212> TYPE: PRT
<213> ORGANISM: Homo sapiens

<400> SEQUENCE: 17

Ala Pro Arg Gly Lys Ser Gly Ala Ala Leu Ser Lys Lys Ser Lys Gly
1               5                   10                  15

<210> SEQ ID NO 18
<211> LENGTH: 18
<212> TYPE: PRT
<213> ORGANISM: Homo sapiens

<400> SEQUENCE: 18

Lys Lys Ser Lys Gly Gln Val Lys Glu Glu Gly Ile Asn Lys Ser Glu
1               5                   10                  15

Lys Arg

<210> SEQ ID NO 19
<211> LENGTH: 23
<212> TYPE: PRT
<213> ORGANISM: Homo sapiens

<400> SEQUENCE: 19

Gly Ser Lys Ala Glu Lys Thr Leu Gly Asp Phe Ala Ala Glu Tyr Ala
1               5                   10                  15

Lys Ser Asn Arg Ser Thr Cys
            20

<210> SEQ ID NO 20
<211> LENGTH: 34
<212> TYPE: PRT
<213> ORGANISM: Homo sapiens

<400> SEQUENCE: 20

Gly Val Lys Ser Glu Gly Lys Arg Lys Gly Asp Glu Val Asp Gly Val
1               5                   10                  15

Asp Glu Val Ala Lys Lys Lys Ser Lys Lys Glu Lys Asp Lys Asp Ser
            20                  25                  30

Lys Leu

<210> SEQ ID NO 21
<211> LENGTH: 25
<212> TYPE: PRT
<213> ORGANISM: Homo sapiens

<400> SEQUENCE: 21

Ala Arg Lys Ser Thr Gly Gly Lys Ala Pro Arg Lys Gln Leu Ala Thr
1               5                   10                  15

Lys Ala Ala Arg Lys Ser Ala Pro Ala
            20                  25

<210> SEQ ID NO 22
<211> LENGTH: 25
<212> TYPE: PRT
<213> ORGANISM: Homo sapiens

<400> SEQUENCE: 22

Ala Arg Lys Ser Thr Gly Gly Lys Ala Pro Arg Lys Gln Leu Ala Thr
1               5                   10                  15

Lys Ala Ala Arg Lys Ser Ala Pro Ala
            20                  25

<210> SEQ ID NO 23
<211> LENGTH: 25
<212> TYPE: PRT
<213> ORGANISM: Homo sapiens

<400> SEQUENCE: 23

Ala Arg Lys Ser Thr Gly Gly Lys Ala Pro Arg Lys Gln Leu Ala Thr
1               5                   10                  15

Lys Ala Ala Arg Lys Ser Ala Pro Ser
            20                  25

<210> SEQ ID NO 24
<211> LENGTH: 25
<212> TYPE: PRT
<213> ORGANISM: Homo sapiens

```
<400> SEQUENCE: 24

Ala Arg Lys Ser Thr Gly Gly Lys Ala Pro Arg Lys Gln Leu Ala Thr
1               5                   10                  15

Lys Ala Ala Arg Lys Ser Thr Pro Ser
            20                  25

<210> SEQ ID NO 25
<211> LENGTH: 25
<212> TYPE: PRT
<213> ORGANISM: Homo sapiens

<400> SEQUENCE: 25

Ala Arg Lys Ser Thr Gly Gly Lys Ala Pro Arg Lys Gln Leu Ala Thr
1               5                   10                  15

Lys Val Ala Arg Lys Ser Ala Pro Ala
            20                  25

<210> SEQ ID NO 26
<211> LENGTH: 19
<212> TYPE: PRT
<213> ORGANISM: Homo sapiens

<400> SEQUENCE: 26

Pro Glu Pro Ala Lys Ser Ala Pro Ala Pro Lys Lys Gly Ser Lys Lys
1               5                   10                  15

Ala Val Thr

<210> SEQ ID NO 27
<211> LENGTH: 49
<212> TYPE: PRT
<213> ORGANISM: Homo sapiens

<400> SEQUENCE: 27

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala Arg Arg Gly Gly Val Lys Arg Ile Ser Gly
        35                  40                  45

Leu

<210> SEQ ID NO 28
<211> LENGTH: 21
<212> TYPE: PRT
<213> ORGANISM: Homo sapiens

<400> SEQUENCE: 28

Ser Gly Arg Gly Lys Gln Gly Gly Lys Ala Arg Ala Lys Ala Lys Thr
1               5                   10                  15

Arg Ser Ser Arg Ala
            20

<210> SEQ ID NO 29
<211> LENGTH: 21
<212> TYPE: PRT
<213> ORGANISM: Homo sapiens

<400> SEQUENCE: 29

Ser Gly Arg Gly Lys Gln Gly Gly Lys Ala Arg Ala Lys Ala Lys Thr
1               5                   10                  15
```

-continued

Arg Ser Ser Arg Ala
            20

<210> SEQ ID NO 30
<211> LENGTH: 21
<212> TYPE: PRT
<213> ORGANISM: Homo sapiens

<400> SEQUENCE: 30

Ser Gly Arg Gly Lys Gln Gly Gly Lys Ala Arg Ala Lys Ala Lys Thr
1               5                   10                  15

Arg Ser Ser Arg Ala
            20

<210> SEQ ID NO 31
<211> LENGTH: 33
<212> TYPE: PRT
<213> ORGANISM: Homo sapiens

<400> SEQUENCE: 31

Lys Lys Ser Val Ala Phe Lys Lys Thr Lys Lys Glu Ile Lys Lys Val
1               5                   10                  15

Ala Thr Pro Lys Lys Ala Ser Lys Pro Lys Lys Ala Ala Ser Lys Ala
            20                  25                  30

Pro

<210> SEQ ID NO 32
<211> LENGTH: 19
<212> TYPE: PRT
<213> ORGANISM: Homo sapiens

<400> SEQUENCE: 32

Lys Ser Pro Lys Lys Ala Lys Val Ala Lys Pro Lys Lys Ala Ala Lys
1               5                   10                  15

Ser Ala Ala

<210> SEQ ID NO 33
<211> LENGTH: 25
<212> TYPE: PRT
<213> ORGANISM: Homo sapiens

<400> SEQUENCE: 33

Lys Lys Ser Ala Lys Lys Thr Pro Lys Lys Ala Lys Lys Pro Ala Ala
1               5                   10                  15

Ala Ala Gly Ala Lys Lys Ala Lys Ser
            20                  25

<210> SEQ ID NO 34
<211> LENGTH: 6
<212> TYPE: PRT
<213> ORGANISM: Homo sapiens

<400> SEQUENCE: 34

Glu Arg Ser Gly Val Ser
1               5

<210> SEQ ID NO 35
<211> LENGTH: 11
<212> TYPE: PRT
<213> ORGANISM: Homo sapiens

<400> SEQUENCE: 35

```
Ser Phe Lys Leu Asn Lys Ala Ala Ser Gly
1               5                   10

<210> SEQ ID NO 36
<211> LENGTH: 27
<212> TYPE: PRT
<213> ORGANISM: Homo sapiens

<400> SEQUENCE: 36

Ala Gln Lys Ser Asn Gln Asn Gly Lys Asp Ser Lys Pro Ser Ser Thr
1               5                   10                  15

Pro Arg Ser Lys Gly Gln Glu Ser Phe Lys Lys
            20                  25

<210> SEQ ID NO 37
<211> LENGTH: 63
<212> TYPE: PRT
<213> ORGANISM: Homo sapiens

<400> SEQUENCE: 37

Ser Gly Arg Glu Gly Lys Lys Pro Leu Lys Gln Pro Lys Lys
1               5                   10                  15

Gln Ala Lys Glu Met Asp Glu Asp Lys Ala Phe Lys Gln Lys Gln
            20                  25                  30

Lys Glu Glu Gln Lys Lys Leu Glu Glu Leu Lys Ala Lys Ala Ala Gly
        35                  40                  45

Lys Gly Pro Leu Ala Thr Gly Gly Ile Lys Lys Ser Gly Lys Lys
    50                  55                  60

<210> SEQ ID NO 38
<211> LENGTH: 19
<212> TYPE: PRT
<213> ORGANISM: Homo sapiens

<400> SEQUENCE: 38

Thr Ser Lys Ser Lys Lys Ser Val Lys Ser Ala Asn Val Lys Lys Ala
1               5                   10                  15

Asp Ser Ser

<210> SEQ ID NO 39
<211> LENGTH: 9
<212> TYPE: PRT
<213> ORGANISM: Homo sapiens

<400> SEQUENCE: 39

Ala Ala Gly Lys Ser Ser Gly Pro Thr
1               5

<210> SEQ ID NO 40
<211> LENGTH: 23
<212> TYPE: PRT
<213> ORGANISM: Homo sapiens

<400> SEQUENCE: 40

Pro Lys Ala Pro Lys Gly Lys Ser Ala Gly Arg Glu Lys Lys Val Ile
1               5                   10                  15

His Pro Tyr Ser Arg Lys Ala
            20

<210> SEQ ID NO 41
<211> LENGTH: 12
<212> TYPE: PRT
```

<213> ORGANISM: Homo sapiens

<400> SEQUENCE: 41

Ser Ser Ser Lys Ser Ser Gln Pro Leu Ala Ser Lys
1               5                   10

<210> SEQ ID NO 42
<211> LENGTH: 12
<212> TYPE: PRT
<213> ORGANISM: Homo sapiens

<400> SEQUENCE: 42

Val Ser Pro Gly Thr Ala Leu Val Gly Ser Gln Lys
1               5                   10

<210> SEQ ID NO 43
<211> LENGTH: 9
<212> TYPE: PRT
<213> ORGANISM: Homo sapiens

<400> SEQUENCE: 43

Lys Arg Lys Val Ser Ser Ala Glu Gly
1               5

<210> SEQ ID NO 44
<211> LENGTH: 9
<212> TYPE: PRT
<213> ORGANISM: Homo sapiens

<400> SEQUENCE: 44

Arg Arg Ser Ala Arg Leu Ser Ala Lys
1               5

<210> SEQ ID NO 45
<211> LENGTH: 17
<212> TYPE: PRT
<213> ORGANISM: Homo sapiens

<400> SEQUENCE: 45

Ser Glu Tyr Arg Pro Lys Ile Lys Gly Glu His Pro Gly Leu Ser Ile
1               5                   10                  15

Gly

<210> SEQ ID NO 46
<211> LENGTH: 17
<212> TYPE: PRT
<213> ORGANISM: Homo sapiens

<400> SEQUENCE: 46

Ser Ala Lys Ala Thr Ala Asp Arg Lys Ser Ala Ser Lys Pro Ile Gly
1               5                   10                  15

Phe

<210> SEQ ID NO 47
<211> LENGTH: 26
<212> TYPE: PRT
<213> ORGANISM: Homo sapiens

<400> SEQUENCE: 47

Ser Ser Val His Leu Gln Gln Asn Asn Tyr Gly Val Lys Ser Val Gly
1               5                   10                  15

Gln Gly Tyr Ser Val Gly Gln Ser Met Arg
                20                  25

<210> SEQ ID NO 48
<211> LENGTH: 31
<212> TYPE: PRT
<213> ORGANISM: Homo sapiens

<400> SEQUENCE: 48

Lys Pro Gln Pro Lys Val Gln Glu Lys Ala Asp Ile Pro Val Lys Ser
1               5                   10                  15

Ser Pro Gln Ala Ala Val Pro Tyr Lys Lys Asp Val Gly Lys Thr
            20                  25                  30

<210> SEQ ID NO 49
<211> LENGTH: 31
<212> TYPE: PRT
<213> ORGANISM: Homo sapiens

<400> SEQUENCE: 49

Gln Glu Leu Gln Ile Thr Thr Gly Arg Glu Ser Lys Arg Leu Lys Ser
1               5                   10                  15

Ser Gln Leu Leu Glu Pro Ala Val Glu Glu Thr Thr Lys Lys Glu
            20                  25                  30

<210> SEQ ID NO 50
<211> LENGTH: 31
<212> TYPE: PRT
<213> ORGANISM: Homo sapiens

<400> SEQUENCE: 50

His Arg Pro Arg Ile Leu Glu Met Asp Lys Glu Glu Asn Arg Arg Ser
1               5                   10                  15

Val Leu Leu Pro Thr His Arg Arg Arg Gly Ser Phe Ser Ser Glu
            20                  25                  30

<210> SEQ ID NO 51
<211> LENGTH: 31
<212> TYPE: PRT
<213> ORGANISM: Homo sapiens

<400> SEQUENCE: 51

Ile Leu Arg Lys Thr Arg Leu Asp Ala Pro Arg Leu Glu Thr Lys Ser
1               5                   10                  15

Leu Ser Ser Ser Val Leu Pro Pro Ser Tyr Ala Ser Asp Arg Leu
            20                  25                  30

<210> SEQ ID NO 52
<211> LENGTH: 31
<212> TYPE: PRT
<213> ORGANISM: Homo sapiens

<400> SEQUENCE: 52

Asp Lys Asn Ser Glu Lys Arg Lys Glu Gln Thr Glu Lys His Lys Ser
1               5                   10                  15

Val Pro Gly Tyr Leu Ser Glu Lys Asp Lys Lys Arg Arg Glu Ser
            20                  25                  30

<210> SEQ ID NO 53
<211> LENGTH: 31
<212> TYPE: PRT
<213> ORGANISM: Homo sapiens

<400> SEQUENCE: 53

-continued

Ser Glu Ala Lys Asp Glu Lys Glu Leu Arg Thr Ser Phe Trp Lys Ser
1               5                   10                  15

Val Leu Ala Gly Pro Leu Arg Thr Pro Leu Cys Gly Gly His Arg
            20                  25                  30

<210> SEQ ID NO 54
<211> LENGTH: 31
<212> TYPE: PRT
<213> ORGANISM: Homo sapiens

<400> SEQUENCE: 54

Glu Ser Lys Ala Arg Asp Lys Gly Asn Asn Pro Glu Thr Lys Lys Ser
1               5                   10                  15

Ile Pro Cys Pro Pro Lys Thr Thr Ala Gly Lys Lys Cys Ser Ala
            20                  25                  30

<210> SEQ ID NO 55
<211> LENGTH: 27
<212> TYPE: PRT
<213> ORGANISM: Homo sapiens

<400> SEQUENCE: 55

His Ser Arg Lys Lys Ser Ala Arg Ile Arg Arg Asn Trp Arg Lys Ser
1               5                   10                  15

Gly Pro Thr Ser Tyr Leu His Gln Ile Arg His
            20                  25

<210> SEQ ID NO 56
<211> LENGTH: 23
<212> TYPE: PRT
<213> ORGANISM: Homo sapiens

<400> SEQUENCE: 56

Met Thr His Thr Arg Arg Lys Ser Leu Pro Met Leu Ser Ser Gly Leu
1               5                   10                  15

Thr Gly Arg Arg Glu Pro Leu
            20

<210> SEQ ID NO 57
<211> LENGTH: 31
<212> TYPE: PRT
<213> ORGANISM: Homo sapiens

<400> SEQUENCE: 57

Cys Cys Ala Ala Arg Val Asp Leu Lys Glu Asp Lys Pro Arg Lys Ser
1               5                   10                  15

Leu Phe Asn Asp Ala Gly Asn Lys Lys Asn Ser Ile Lys Met Trp
            20                  25                  30

<210> SEQ ID NO 58
<211> LENGTH: 31
<212> TYPE: PRT
<213> ORGANISM: Homo sapiens

<400> SEQUENCE: 58

Asp Tyr Arg Gln Phe Arg Lys Ser Val Leu Ala Asp Gln Gly Lys Ser
1               5                   10                  15

Phe Ala Thr Ala Ser His Arg Asn Thr Glu Glu Gly Leu Lys
            20                  25                  30

<210> SEQ ID NO 59
<211> LENGTH: 31

```
<212> TYPE: PRT
<213> ORGANISM: Homo sapiens

<400> SEQUENCE: 59

Gly Asp Asp Thr Glu Glu Thr Glu Asp Tyr Arg Gln Phe Arg Lys Ser
1               5                   10                  15

Val Leu Ala Asp Gln Gly Lys Ser Phe Ala Thr Ala Ser His Arg
            20                  25                  30

<210> SEQ ID NO 60
<211> LENGTH: 31
<212> TYPE: PRT
<213> ORGANISM: Homo sapiens

<400> SEQUENCE: 60

Thr Gln Arg Asp Thr Gln Tyr Arg Ser His His Ala Gln Asp Lys Ser
1               5                   10                  15

Leu Leu Ser Gln Gly Arg Arg His Leu Trp Arg Ala Arg Glu Met
            20                  25                  30

<210> SEQ ID NO 61
<211> LENGTH: 31
<212> TYPE: PRT
<213> ORGANISM: Homo sapiens

<400> SEQUENCE: 61

Lys Gly Gly Ser Ala Thr Cys Arg Lys Ile Ser Ser Lys Thr Lys Ser
1               5                   10                  15

Ser Ser Ile Ile Gly Ser Ser Ser Ala Ser His Thr Ser Gln Ala
            20                  25                  30

<210> SEQ ID NO 62
<211> LENGTH: 31
<212> TYPE: PRT
<213> ORGANISM: Homo sapiens

<400> SEQUENCE: 62

Asp Trp Asp Asp Met Asp Asp Phe Asp Thr Ser Glu Thr Ser Lys Ser
1               5                   10                  15

Phe Val Thr Pro Pro Gln Ser His Phe Val Arg Val Ser Thr Ala
            20                  25                  30

<210> SEQ ID NO 63
<211> LENGTH: 31
<212> TYPE: PRT
<213> ORGANISM: Homo sapiens

<400> SEQUENCE: 63

Lys Glu Leu Glu Lys Arg Leu Gln Asp Val Ser Gly Gln Leu Ser Ser
1               5                   10                  15

Ser Lys Lys Pro Ala Arg Lys Glu Lys Pro Gly Ser Ala Pro Ser
            20                  25                  30

<210> SEQ ID NO 64
<211> LENGTH: 31
<212> TYPE: PRT
<213> ORGANISM: Homo sapiens

<400> SEQUENCE: 64

Lys Lys Lys Arg Lys Gly Gln Glu Asp Arg Lys Ser Lys Lys Lys Ser
1               5                   10                  15

Ala Pro Ser Ile Leu Ser Asn Gly Arg Ile Gly Gln Val Gly Lys
```

<210> SEQ ID NO 65
<211> LENGTH: 31
<212> TYPE: PRT
<213> ORGANISM: Homo sapiens

<400> SEQUENCE: 65

Glu Pro Ser Pro Leu Pro Gly Ser Leu Ile Arg Gly Gln Arg Lys Ser
1               5                   10                  15
Ala Ser Ser Phe Phe Lys Glu Leu Arg Glu Glu Arg His Cys Ala
            20                  25                  30

<210> SEQ ID NO 66
<211> LENGTH: 31
<212> TYPE: PRT
<213> ORGANISM: Homo sapiens

<400> SEQUENCE: 66

Asp Ser Arg Leu Glu Gln Tyr Thr Ser Ala Ile Glu Gly Thr Lys Ser
1               5                   10                  15
Ala Lys Pro Thr Lys Pro Ala Ala Ser Asp Leu Pro Val Pro Ala
            20                  25                  30

<210> SEQ ID NO 67
<211> LENGTH: 31
<212> TYPE: PRT
<213> ORGANISM: Homo sapiens

<400> SEQUENCE: 67

Pro Lys Ser Gly Arg Val Trp Lys Asp Arg Ser Lys Lys Arg Phe Ser
1               5                   10                  15
Gln Met Leu Gln Asp Lys Pro Leu Arg Thr Ser Trp Gln Arg Lys
            20                  25                  30

<210> SEQ ID NO 68
<211> LENGTH: 31
<212> TYPE: PRT
<213> ORGANISM: Homo sapiens

<400> SEQUENCE: 68

Arg Phe Cys Ala Phe Gly Gly Asn Pro Pro Val Thr Gly Pro Arg Ser
1               5                   10                  15
Ala Leu Ala Pro Asn Leu Leu Thr Ser Gly Lys Lys Lys Glu
            20                  25                  30

<210> SEQ ID NO 69
<211> LENGTH: 31
<212> TYPE: PRT
<213> ORGANISM: Homo sapiens

<400> SEQUENCE: 69

Asn Leu Asn Gly Phe Asp Val Glu Glu Ala Lys Ile Leu Arg Leu Ser
1               5                   10                  15
Gly Lys Pro Gln Asn Ala Pro Glu Gly Tyr Gln Asn Arg Leu Lys
            20                  25                  30

<210> SEQ ID NO 70
<211> LENGTH: 31
<212> TYPE: PRT
<213> ORGANISM: Homo sapiens

<400> SEQUENCE: 70

```
Pro Ser Lys Lys Ser Val Ala Arg Ile Gly Gln Thr Gly Thr Lys Ser
1               5                   10                  15

Val Phe Ser Gln Ser Gly Asn Ser Arg Glu Val Thr Pro Ile Leu
                20                  25                  30
```

<210> SEQ ID NO 71
<211> LENGTH: 31
<212> TYPE: PRT
<213> ORGANISM: Homo sapiens

<400> SEQUENCE: 71

```
Ala Asn Thr Lys Ala Thr Ser Gln Phe Lys Gly Tyr Arg Arg Arg Ser
1               5                   10                  15

Ser Leu Asn Gly Lys Gly Glu Ser Ser Leu Thr Ala Leu Glu Arg
                20                  25                  30
```

<210> SEQ ID NO 72
<211> LENGTH: 31
<212> TYPE: PRT
<213> ORGANISM: Homo sapiens

<400> SEQUENCE: 72

```
Gly Pro Ala Ala Gly Ser Ser Asp Glu Pro Gly Lys Arg Arg Lys Ser
1               5                   10                  15

Phe Cys Ile Ser Thr Leu Ala Asn Thr Lys Ala Thr Ser Gln Phe
                20                  25                  30
```

<210> SEQ ID NO 73
<211> LENGTH: 31
<212> TYPE: PRT
<213> ORGANISM: Homo sapiens

<400> SEQUENCE: 73

```
Ser Cys Arg Lys Lys Lys Gly Lys Gly Lys Lys Ser Val Gln Lys Ser
1               5                   10                  15

Leu Tyr Gly Glu Arg Asp Ile Ala Ser Lys Lys Pro Leu Leu Ser
                20                  25                  30
```

<210> SEQ ID NO 74
<211> LENGTH: 31
<212> TYPE: PRT
<213> ORGANISM: Homo sapiens

<400> SEQUENCE: 74

```
Arg Ser Arg His Ser Ser Ile Ser Pro Ser Thr Leu Thr Leu Lys Ser
1               5                   10                  15

Ser Leu Ala Ala Glu Leu Asn Lys Asn Lys Lys Ala Arg Ala Ala
                20                  25                  30
```

<210> SEQ ID NO 75
<211> LENGTH: 31
<212> TYPE: PRT
<213> ORGANISM: Homo sapiens

<400> SEQUENCE: 75

```
Phe Phe Val Pro Leu Lys Glu Leu Ala Asp Leu Pro Gln Asn Lys Ser
1               5                   10                  15

Ser Gln Glu Ser Ile Val Cys Glu Leu Arg Cys Lys Ser Val Tyr
                20                  25                  30
```

<210> SEQ ID NO 76

```
<211> LENGTH: 31
<212> TYPE: PRT
<213> ORGANISM: Homo sapiens

<400> SEQUENCE: 76

Arg Ser Arg Ser Ser Ala Ala Lys Leu Arg Gly Gln Lys Arg Ser
1               5                   10                  15

Gly Ala Ser Ala Ala Pro Ala Ala Ser Ala Ala Ala Ala Leu Ala
            20                  25                  30

<210> SEQ ID NO 77
<211> LENGTH: 31
<212> TYPE: PRT
<213> ORGANISM: Homo sapiens

<400> SEQUENCE: 77

Leu Phe Cys Thr Ser Cys Asn Val Val Leu Asn His Val Arg Lys Ser
1               5                   10                  15

Ala Ile Ser Asp His Leu Lys Ser Lys Thr His Thr Lys Arg Lys
            20                  25                  30

<210> SEQ ID NO 78
<211> LENGTH: 31
<212> TYPE: PRT
<213> ORGANISM: Homo sapiens

<400> SEQUENCE: 78

Val Val Leu Gln Asp Ile Leu Ala Val Arg Pro Pro Gln Ile Lys Ser
1               5                   10                  15

Leu Pro Ala Thr Pro Gln Gly Lys Asn Met Thr Pro Glu Ser Glu
            20                  25                  30

<210> SEQ ID NO 79
<211> LENGTH: 31
<212> TYPE: PRT
<213> ORGANISM: Homo sapiens

<400> SEQUENCE: 79

Glu Ser Gln Lys Ser Ser Arg Gly Gly Ser Pro Asp Leu Trp Lys Ser
1               5                   10                  15

Ser Phe Phe Ile Glu Pro Gln Lys Pro Val Phe Pro Glu Thr Arg
            20                  25                  30

<210> SEQ ID NO 80
<211> LENGTH: 31
<212> TYPE: PRT
<213> ORGANISM: Homo sapiens

<400> SEQUENCE: 80

Pro Ser Ser Trp Lys Ser Pro Ala Ser Pro Glu Ser Trp Lys Ser
1               5                   10                  15

Gly Pro Pro Glu Leu Arg Lys Thr Ala Pro Thr Leu Ser Pro Glu
            20                  25                  30

<210> SEQ ID NO 81
<211> LENGTH: 31
<212> TYPE: PRT
<213> ORGANISM: Homo sapiens

<400> SEQUENCE: 81

Val Gln Ala Lys Pro Pro Lys Val Asp Gly Ala Glu Phe Trp Lys Ser
1               5                   10                  15
```

-continued

Ser Pro Ser Ile Leu Ala Val Gln Arg Ser Ala Ile Leu Lys Lys
            20                  25                  30

<210> SEQ ID NO 82
<211> LENGTH: 31
<212> TYPE: PRT
<213> ORGANISM: Homo sapiens

<400> SEQUENCE: 82

Ala Arg Gly Ile Pro Thr Tyr Ile Tyr Tyr Phe Pro Arg Ser Lys Ser
1               5                   10                  15

Ala Val Leu His Ser Gln Ser Ser Ser Ser Ser Arg Gln Leu
            20                  25                  30

<210> SEQ ID NO 83
<211> LENGTH: 31
<212> TYPE: PRT
<213> ORGANISM: Homo sapiens

<400> SEQUENCE: 83

Lys Asp His His Tyr Gly Asp Arg Arg His Met Asp Ala His Arg Ser
1               5                   10                  15

Gly Ser Tyr Arg Pro Asn Asn Met Ser Arg Lys Arg Pro Tyr Asp
            20                  25                  30

<210> SEQ ID NO 84
<211> LENGTH: 31
<212> TYPE: PRT
<213> ORGANISM: Homo sapiens

<400> SEQUENCE: 84

Thr Ala Asp Gly Gln Thr Arg Ala Leu Val Asn His Ser Gly Leu Ser
1               5                   10                  15

Ala Pro Val Pro Arg Gly Arg Lys Gly Lys Lys Val Lys Ala Gln
            20                  25                  30

<210> SEQ ID NO 85
<211> LENGTH: 31
<212> TYPE: PRT
<213> ORGANISM: Homo sapiens

<400> SEQUENCE: 85

Ile Thr Pro Thr Ala Asp Gly Gln Thr Arg Ala Leu Val Asn His Ser
1               5                   10                  15

Gly Leu Ser Ala Pro Val Pro Arg Gly Arg Lys Gly Lys Lys Val
            20                  25                  30

<210> SEQ ID NO 86
<211> LENGTH: 31
<212> TYPE: PRT
<213> ORGANISM: Homo sapiens

<400> SEQUENCE: 86

Glu Leu Gln Ser Ala Ser Glu Thr Ser Leu Val Asn Phe Pro Lys Ser
1               5                   10                  15

Ile Pro Val Ser Gly Thr Ser Ile Gln Pro Thr Leu Gly Ala Asn
            20                  25                  30

<210> SEQ ID NO 87
<211> LENGTH: 31
<212> TYPE: PRT
<213> ORGANISM: Homo sapiens

```
<400> SEQUENCE: 87

Leu Asn Pro Ala Ser Phe Pro Arg Met Asn Gly Pro Ala Gly Lys Ser
1               5                   10                  15

Phe Val Pro Phe Pro Arg Val Gly Ser Leu Pro Gly Thr Asn Pro
            20                  25                  30

<210> SEQ ID NO 88
<211> LENGTH: 31
<212> TYPE: PRT
<213> ORGANISM: Homo sapiens

<400> SEQUENCE: 88

Glu Val Gly Ser Ser Arg Gln Leu Lys Leu Ser Ile Thr Lys Lys Ser
1               5                   10                  15

Ser Pro Ser Val Lys Pro Ala Val Asp Pro Ala Ala Ala Lys Leu
            20                  25                  30

<210> SEQ ID NO 89
<211> LENGTH: 31
<212> TYPE: PRT
<213> ORGANISM: Homo sapiens

<400> SEQUENCE: 89

Ser Pro Thr Ala Ala Thr Ser Gln Gln Gln Gln Leu Lys Asn Lys Ser
1               5                   10                  15

Ile Leu Ile Ser Ser Val Ala Ser Val His His Ala Asn Gly Leu
            20                  25                  30

<210> SEQ ID NO 90
<211> LENGTH: 18
<212> TYPE: PRT
<213> ORGANISM: Homo sapiens

<400> SEQUENCE: 90

Met Lys Ser Val Cys Pro Val Thr Ser Gly Phe Ser Ser Pro Ser Pro
1               5                   10                  15

Ser Ala

<210> SEQ ID NO 91
<211> LENGTH: 18
<212> TYPE: PRT
<213> ORGANISM: Homo sapiens

<400> SEQUENCE: 91

Met Lys Ser Ser Val Ala Gln Ile Lys Pro Ser Ser Gly His Asp Arg
1               5                   10                  15

Arg Glu

<210> SEQ ID NO 92
<211> LENGTH: 31
<212> TYPE: PRT
<213> ORGANISM: Homo sapiens

<400> SEQUENCE: 92

Gly Val Gly Ala Met Leu Ala Arg Gly Ser Ala Ser Pro His Lys Ser
1               5                   10                  15

Ser Pro Gln Pro Leu Val Ala Thr Pro Ser Gln His His Gln Gln
            20                  25                  30

<210> SEQ ID NO 93
<211> LENGTH: 31
```

```
<212> TYPE: PRT
<213> ORGANISM: Homo sapiens

<400> SEQUENCE: 93

Ala Ser Val Ala Asp Thr Pro Pro Glu Arg Arg Asn Lys Ser
1               5                   10                  15

Gly Ile Ile Ser Glu Pro Leu Asn Lys Ser Leu Arg Arg Ser Arg
            20                  25                  30

<210> SEQ ID NO 94
<211> LENGTH: 31
<212> TYPE: PRT
<213> ORGANISM: Homo sapiens

<400> SEQUENCE: 94

Tyr Pro His Ile Lys Arg Ile Ala Arg His Arg His Leu Pro Lys Ser
1               5                   10                  15

Ile Tyr Ser Gln Ile Gln Glu Gln Arg Ile Met Lys Glu Ala Arg
            20                  25                  30

<210> SEQ ID NO 95
<211> LENGTH: 31
<212> TYPE: PRT
<213> ORGANISM: Homo sapiens

<400> SEQUENCE: 95

Glu Pro Val Arg Gly Pro Ala Lys Lys Gln Lys Gln Gly Lys Lys Ser
1               5                   10                  15

Val Phe Asp Glu Glu Leu Thr Asn Thr Ser Lys Lys Ala Leu Lys
            20                  25                  30

<210> SEQ ID NO 96
<211> LENGTH: 31
<212> TYPE: PRT
<213> ORGANISM: Homo sapiens

<400> SEQUENCE: 96

Gly Gly Asp Gly Ala Glu Ala Pro Ala Lys Lys Asp Val Lys Gly Ser
1               5                   10                  15

Tyr Val Ser Ile His Ser Ser Gly Phe Arg Asp Phe Leu Leu Lys
            20                  25                  30

<210> SEQ ID NO 97
<211> LENGTH: 31
<212> TYPE: PRT
<213> ORGANISM: Homo sapiens

<400> SEQUENCE: 97

Lys Leu Pro Gln Gln Ser His Ser Ala Phe Gly Ala Thr Ser Ser Ser
1               5                   10                  15

Ser Gly Phe Gly Lys Ser Ala Pro Pro Gln Leu Pro Ser Phe Tyr
            20                  25                  30

<210> SEQ ID NO 98
<211> LENGTH: 31
<212> TYPE: PRT
<213> ORGANISM: Homo sapiens

<400> SEQUENCE: 98

Glu Glu Tyr Tyr Asp Gly Asn Thr Ser Ser Asn Ser Arg Gln Arg Ser
1               5                   10                  15

Gly Trp Ser Ser Gly Arg Ser Gly Arg Ser Gly Arg Ser Gly Gly
```

```
                        20                  25                  30

<210> SEQ ID NO 99
<211> LENGTH: 31
<212> TYPE: PRT
<213> ORGANISM: Homo sapiens

<400> SEQUENCE: 99

Glu Asp Glu Asp Asp Glu Glu Glu Glu Glu Glu Lys Glu Lys Ser
1               5                   10                  15

Leu Ile Val Glu Gly Lys Arg Glu Lys Lys Val Glu Arg Leu
                20                  25                  30

<210> SEQ ID NO 100
<211> LENGTH: 17
<212> TYPE: PRT
<213> ORGANISM: Homo sapiens

<400> SEQUENCE: 100

Met Ser Tyr Asp Tyr His Gln Asn Trp Gly Arg Asp Gly Gly Pro Arg
1               5                   10                  15

Ser

<210> SEQ ID NO 101
<211> LENGTH: 31
<212> TYPE: PRT
<213> ORGANISM: Homo sapiens

<400> SEQUENCE: 101

Thr Asp Leu Asp Cys Gln Val Gly Gly Leu Ile Cys Lys Ser Lys Ser
1               5                   10                  15

Ala Ala Ser Glu Gln His Val Phe Lys Ala Pro Ala Pro Arg Pro
                20                  25                  30

<210> SEQ ID NO 102
<211> LENGTH: 17
<212> TYPE: PRT
<213> ORGANISM: Homo sapiens

<400> SEQUENCE: 102

Met Ser Arg Phe Pro Ala Val Ala Gly Arg Ala Pro Arg Arg Gln Glu
1               5                   10                  15

Glu

<210> SEQ ID NO 103
<211> LENGTH: 31
<212> TYPE: PRT
<213> ORGANISM: Homo sapiens

<400> SEQUENCE: 103

Ala Val Gly Lys Gln Pro Ala Pro Arg Asn Leu Val Pro Lys Lys Ser
1               5                   10                  15

Ser Phe Ala Asn Val Ala Ala Ala Thr Pro Ala Ile Lys Lys Pro
                20                  25                  30

<210> SEQ ID NO 104
<211> LENGTH: 31
<212> TYPE: PRT
<213> ORGANISM: Homo sapiens

<400> SEQUENCE: 104

Ser Val Pro Met Ala Ser Pro Ala Pro Gly Arg Leu Gly Ala Met Ser
1               5                   10                  15
```

-continued

```
                1               5                  10                  15
Ala Ala Pro Ser Gln Pro Asn Ser Gln Ile Arg Gln Asn Ile Arg
            20                  25              30

<210> SEQ ID NO 105
<211> LENGTH: 31
<212> TYPE: PRT
<213> ORGANISM: Homo sapiens

<400> SEQUENCE: 105

Gln Asp Val Pro Lys Pro Val Leu Thr Ser Val Met Val Pro Lys Ser
1               5                   10                  15

Ile Leu Ala Lys Pro Ser Ser Ser Pro Asp Pro Arg Tyr Leu Ser
            20                  25              30

<210> SEQ ID NO 106
<211> LENGTH: 31
<212> TYPE: PRT
<213> ORGANISM: Homo sapiens

<400> SEQUENCE: 106

Ile Gly Arg Arg Arg Gly Arg Gln Glu Gln Arg Arg Glu Leu Lys Ser
1               5                   10                  15

Ala Gly Gly Leu Met Phe Asn Thr Gly Ile Gly Gln His Ile Leu
            20                  25              30

<210> SEQ ID NO 107
<211> LENGTH: 31
<212> TYPE: PRT
<213> ORGANISM: Homo sapiens

<400> SEQUENCE: 107

Pro Ala Val Pro Glu Thr Ala Gly Ile Lys Phe Pro Asp Phe Lys Ser
1               5                   10                  15

Ala Gly Val Thr Leu Arg Ser Gln Arg Met Lys Leu Pro Ser Ser
            20                  25              30

<210> SEQ ID NO 108
<211> LENGTH: 31
<212> TYPE: PRT
<213> ORGANISM: Homo sapiens

<400> SEQUENCE: 108

Pro Pro Lys Pro Leu Ser Lys Pro Arg Thr Pro Arg Arg Ser Lys Ser
1               5                   10                  15

Asp Gly Glu Ala Lys Pro Glu Pro Ser Pro Ser Pro Arg Ile Thr
            20                  25              30

<210> SEQ ID NO 109
<211> LENGTH: 31
<212> TYPE: PRT
<213> ORGANISM: Homo sapiens

<400> SEQUENCE: 109

Lys Ala Ser Ile Gln Ala Ala Ser Ala Glu Ser Ser Gly Gln Lys Ser
1               5                   10                  15

Phe Ala Ala Asn Gly Ile Gln Ala His Pro Glu Ser Ser Thr Gly
            20                  25              30

<210> SEQ ID NO 110
<211> LENGTH: 31
<212> TYPE: PRT
```

```
<213> ORGANISM: Homo sapiens

<400> SEQUENCE: 110

Thr Met Tyr Leu Tyr Glu Lys Ala Asn Thr Pro Glu Leu Lys Lys Ser
1               5                   10                  15

Val Ser Met Leu Ser Leu Asn Thr Pro Asn Ser Asn Arg Lys Arg
            20                  25                  30

<210> SEQ ID NO 111
<211> LENGTH: 31
<212> TYPE: PRT
<213> ORGANISM: Homo sapiens

<400> SEQUENCE: 111

Gly Ala Asp Val Lys Val His Arg Ala Arg Lys Thr Met Pro Lys Ser
1               5                   10                  15

Val Val Gly Leu His Ala Ala Ser Lys Asp Pro Arg Glu Val Arg
            20                  25                  30

<210> SEQ ID NO 112
<211> LENGTH: 25
<212> TYPE: PRT
<213> ORGANISM: Homo sapiens

<400> SEQUENCE: 112

Thr Gly Asp His Ile Pro Thr Pro Gln Asp Leu Pro Gln Arg Lys Ser
1               5                   10                  15

Ser Leu Val Thr Ser Lys Leu Ala Gly
            20                  25

<210> SEQ ID NO 113
<211> LENGTH: 31
<212> TYPE: PRT
<213> ORGANISM: Homo sapiens

<400> SEQUENCE: 113

Glu Ile Asn Arg Leu Pro Ser Ala Asn Gln Gly Ser Pro Phe Lys Ser
1               5                   10                  15

Ala Leu Ser Thr Val Ser Phe Tyr Asn Gln Asn Lys Trp Tyr Leu
            20                  25                  30

<210> SEQ ID NO 114
<211> LENGTH: 31
<212> TYPE: PRT
<213> ORGANISM: Homo sapiens

<400> SEQUENCE: 114

Phe Asn Lys Leu Val Met Pro Asn Tyr Pro Phe Ile Asn Ile Arg Ser
1               5                   10                  15

Ser Gly Val Val Pro Gln Ser Ala Pro Pro Val Pro Thr Ala Ser
            20                  25                  30

<210> SEQ ID NO 115
<211> LENGTH: 31
<212> TYPE: PRT
<213> ORGANISM: Homo sapiens

<400> SEQUENCE: 115

Glu Asn Trp Lys Lys Glu Leu Glu Lys His Arg Glu Lys Leu Leu Ser
1               5                   10                  15

Gly Ser Glu Ser Ser Ser Lys Lys Arg Gln Arg Lys Lys Lys Glu
            20                  25                  30
```

<210> SEQ ID NO 116
<211> LENGTH: 31
<212> TYPE: PRT
<213> ORGANISM: Homo sapiens

<400> SEQUENCE: 116

Met Lys Ser Leu Lys Lys His Arg Ser Pro Glu Arg Lys Ser
1               5                   10                  15

Leu Phe Ile His Glu Asn Asn Glu Lys Asn Asp Arg Asp Arg Gly
                20                  25                  30

<210> SEQ ID NO 117
<211> LENGTH: 31
<212> TYPE: PRT
<213> ORGANISM: Homo sapiens

<400> SEQUENCE: 117

Ser Gly Ser Pro Thr His Ser Leu Ser Gln Lys Ser Thr Arg Leu Ser
1               5                   10                  15

Gly Ala Ala Pro Ala His Ser Ala Ala Asp Pro Trp Glu Lys Glu
                20                  25                  30

<210> SEQ ID NO 118
<211> LENGTH: 31
<212> TYPE: PRT
<213> ORGANISM: Homo sapiens

<400> SEQUENCE: 118

Glu Pro Gly Gln Gln Gly Leu Gln Ala Ala Arg Ser Ala Lys Ser
1               5                   10                  15

Ala Leu Gly Ala Val Ser Gln Arg Ile Gln Glu Ser Cys Gln Ser
                20                  25                  30

<210> SEQ ID NO 119
<211> LENGTH: 31
<212> TYPE: PRT
<213> ORGANISM: Homo sapiens

<400> SEQUENCE: 119

Leu Ser Tyr Lys Arg Val Leu Gln Lys Thr Lys Glu Gln Arg Lys Ser
1               5                   10                  15

Leu Gly Ser Ser His Ser Asn Ser Ser Ser Ser Leu Thr Glu
                20                  25                  30

<210> SEQ ID NO 120
<211> LENGTH: 31
<212> TYPE: PRT
<213> ORGANISM: Homo sapiens

<400> SEQUENCE: 120

Pro Leu Cys Tyr Ser Phe Ile Ser Tyr Val Gln Asn Lys Ser Lys Ser
1               5                   10                  15

Leu Asn Tyr Thr Gly Glu Lys Lys Glu Lys Pro Ala Ala Val Ala
                20                  25                  30

<210> SEQ ID NO 121
<211> LENGTH: 31
<212> TYPE: PRT
<213> ORGANISM: Homo sapiens

<400> SEQUENCE: 121

```
Arg Ser Ala Glu Asp Trp Trp Trp Asp Arg Leu Ala Pro Arg Gly Ser
1               5                   10                  15

Gly Tyr His Leu Leu Gln Ser Asp Ser Met Leu Leu Val Leu Ser
            20                  25                  30
```

<210> SEQ ID NO 122
<211> LENGTH: 31
<212> TYPE: PRT
<213> ORGANISM: Homo sapiens

<400> SEQUENCE: 122

```
Gly Ser Pro Ile Pro His Asp Pro Glu Phe Gly Ser Lys Leu Ala Ser
1               5                   10                  15

Val Pro Glu Tyr Arg Tyr Ser Gln Ser Ala Pro Gly Ser Pro Val
            20                  25                  30
```

<210> SEQ ID NO 123
<211> LENGTH: 31
<212> TYPE: PRT
<213> ORGANISM: Homo sapiens

<400> SEQUENCE: 123

```
Asp Gly Ala Pro Gln Ala Lys Pro Val Pro Ala Gln Lys Leu Lys Ser
1               5                   10                  15

Ala Leu Asn Leu Asn Gln Pro Val Ser Val Ser Ser Val Ser Pro
            20                  25                  30
```

<210> SEQ ID NO 124
<211> LENGTH: 24
<212> TYPE: PRT
<213> ORGANISM: Homo sapiens

<400> SEQUENCE: 124

```
Val Asp Arg Gln Arg Glu Tyr Leu Leu Asp Met Ile Pro Pro Arg Ser
1               5                   10                  15

Ile Pro Gln Ser Ala Thr Trp Lys
            20
```

<210> SEQ ID NO 125
<211> LENGTH: 31
<212> TYPE: PRT
<213> ORGANISM: Homo sapiens

<400> SEQUENCE: 125

```
Leu Leu Gln Lys Met Gly Tyr Lys Ser Gly Gln Ala Leu Gly Lys Ser
1               5                   10                  15

Gly Gly Gly Ile Val Glu Pro Ile Pro Leu Asn Ile Lys Thr Gly
            20                  25                  30
```

<210> SEQ ID NO 126
<211> LENGTH: 31
<212> TYPE: PRT
<213> ORGANISM: Homo sapiens

<400> SEQUENCE: 126

```
Gly Gly Ile Val Glu Pro Ile Pro Leu Asn Ile Lys Thr Gly Lys Ser
1               5                   10                  15

Gly Ile Gly His Glu Ala Ser Leu Lys Arg Lys Ala Glu Glu Lys
            20                  25                  30
```

<210> SEQ ID NO 127
<211> LENGTH: 31

```
<212> TYPE: PRT
<213> ORGANISM: Homo sapiens

<400> SEQUENCE: 127

Gly Thr Lys Leu Leu Leu Pro Arg Ala Ala Ser Val Arg Gly Arg Ser
1               5                   10                  15

Ile Pro Gly Ala Ala Glu Lys Pro Lys Lys Glu Ile Pro Ala Ser
            20                  25                  30

<210> SEQ ID NO 128
<211> LENGTH: 31
<212> TYPE: PRT
<213> ORGANISM: Homo sapiens

<400> SEQUENCE: 128

Ile Glu Leu Ser Pro Thr Gly Arg Pro Lys Arg Arg Thr Arg Lys Ser
1               5                   10                  15

Ile Asn Tyr Ser Lys Ile Asp Asp Phe Pro Asn Glu Leu Glu Lys
            20                  25                  30

<210> SEQ ID NO 129
<211> LENGTH: 31
<212> TYPE: PRT
<213> ORGANISM: Homo sapiens

<400> SEQUENCE: 129

Arg Gln Pro Tyr Phe Ile Tyr Phe Pro Gln Ile Lys Thr Glu Lys Ser
1               5                   10                  15

Gly Ser Ile Gly Ala Ala Asp Ser Pro Glu Asn Trp Glu Lys Val
            20                  25                  30

<210> SEQ ID NO 130
<211> LENGTH: 23
<212> TYPE: PRT
<213> ORGANISM: Homo sapiens

<400> SEQUENCE: 130

Met Ser Glu Ser Ser Lys Ser Ser Gln Pro Leu Ala Ser Lys Gln
1               5                   10                  15

Glu Lys Asp Gly Thr Glu Lys
            20

<210> SEQ ID NO 131
<211> LENGTH: 22
<212> TYPE: PRT
<213> ORGANISM: Homo sapiens

<400> SEQUENCE: 131

Met Pro Lys Arg Lys Val Ser Ser Ala Glu Gly Ala Ala Lys Glu Glu
1               5                   10                  15

Pro Lys Arg Arg Ser Ala
            20

<210> SEQ ID NO 132
<211> LENGTH: 31
<212> TYPE: PRT
<213> ORGANISM: Homo sapiens

<400> SEQUENCE: 132

Glu Gly Ala Ala Lys Glu Glu Pro Lys Arg Arg Ser Ala Arg Leu Ser
1               5                   10                  15

Ala Lys Pro Pro Ala Lys Val Glu Ala Lys Pro Lys Lys Ala Ala
```

<210> SEQ ID NO 133
<211> LENGTH: 31
<212> TYPE: PRT
<213> ORGANISM: Homo sapiens

<400> SEQUENCE: 133

Lys Ala Lys Val Lys Asp Glu Pro Gln Arg Arg Ser Ala Arg Leu Ser
1               5                   10                  15

Ala Lys Pro Ala Pro Pro Lys Pro Glu Pro Lys Pro Lys Lys Ala
                20                  25                  30

<210> SEQ ID NO 134
<211> LENGTH: 31
<212> TYPE: PRT
<213> ORGANISM: Homo sapiens

<400> SEQUENCE: 134

Ser Lys Val Thr Lys Gln Glu Pro Thr Arg Arg Ser Ala Arg Leu Ser
1               5                   10                  15

Ala Lys Pro Ala Pro Pro Lys Pro Glu Pro Lys Pro Arg Lys Thr
                20                  25                  30

<210> SEQ ID NO 135
<211> LENGTH: 31
<212> TYPE: PRT
<213> ORGANISM: Homo sapiens

<400> SEQUENCE: 135

Lys Ala Lys Val Lys Asp Glu Pro Gln Arg Arg Ser Ala Arg Leu Ser
1               5                   10                  15

Ala Lys Pro Ala Pro Pro Lys Pro Glu Pro Arg Pro Lys Lys Ala
                20                  25                  30

<210> SEQ ID NO 136
<211> LENGTH: 31
<212> TYPE: PRT
<213> ORGANISM: Homo sapiens

<400> SEQUENCE: 136

Gln Gly Asp Met Arg Gln Glu Pro Lys Arg Arg Ser Ala Arg Leu Ser
1               5                   10                  15

Ala Met Leu Val Pro Val Thr Pro Glu Val Lys Pro Lys Arg Thr
                20                  25                  30

<210> SEQ ID NO 137
<211> LENGTH: 31
<212> TYPE: PRT
<213> ORGANISM: Homo sapiens

<400> SEQUENCE: 137

Ser Ser Asn Phe Gly Pro Met Lys Gly Gly Asn Phe Gly Gly Arg Ser
1               5                   10                  15

Ser Gly Pro Tyr Gly Gly Gly Gly Gln Tyr Phe Ala Lys Pro Arg
                20                  25                  30

<210> SEQ ID NO 138
<211> LENGTH: 31
<212> TYPE: PRT
<213> ORGANISM: Homo sapiens

<400> SEQUENCE: 138

Tyr Ser Gly Gln Gln Gln Ser Asn Tyr Gly Pro Met Lys Gly Gly Ser
1               5                   10                  15

Phe Gly Gly Arg Ser Ser Gly Ser Pro Tyr Gly Gly Gly Tyr Gly
            20                  25                  30

<210> SEQ ID NO 139
<211> LENGTH: 31
<212> TYPE: PRT
<213> ORGANISM: Homo sapiens

<400> SEQUENCE: 139

Asp Leu Asp Tyr Asp Phe Gln Arg Asp Tyr Tyr Asp Arg Met Tyr Ser
1               5                   10                  15

Tyr Pro Ala Arg Val Pro Pro Pro Pro Ile Ala Arg Ala Val
            20                  25                  30

<210> SEQ ID NO 140
<211> LENGTH: 31
<212> TYPE: PRT
<213> ORGANISM: Homo sapiens

<400> SEQUENCE: 140

Thr Pro Arg Gly Gly Asp Gly Gly Gly Gly Arg Ser Phe Ser
1               5                   10                  15

Gln Pro Glu Ala Gly Gly Ser His His Lys Val Ser Val Ser Pro
            20                  25                  30

<210> SEQ ID NO 141
<211> LENGTH: 31
<212> TYPE: PRT
<213> ORGANISM: Homo sapiens

<400> SEQUENCE: 141

Gln Pro Gln Gln Gln Arg Gly Ala Ala Lys Glu Ala Ala Gly Lys Ser
1               5                   10                  15

Ser Gly Pro Thr Ser Leu Phe Ala Val Thr Val Ala Pro Pro Gly
            20                  25                  30

<210> SEQ ID NO 142
<211> LENGTH: 31
<212> TYPE: PRT
<213> ORGANISM: Homo sapiens

<400> SEQUENCE: 142

Met Lys Trp Lys Lys Asp His Lys Leu Pro Asn Thr Lys Ile Arg Ser
1               5                   10                  15

Gly Gly Ala Ala Gly Ser Ala Gly Gly Pro Pro Gly Arg Pro Asn
            20                  25                  30

<210> SEQ ID NO 143
<211> LENGTH: 31
<212> TYPE: PRT
<213> ORGANISM: Homo sapiens

<400> SEQUENCE: 143

Met Asp Ala Ile Leu Thr Glu Ala Ile Lys Ala Cys Phe Gln Lys Ser
1               5                   10                  15

Gly Ala Ser Val Val Ala Ile Arg Lys Tyr Ile Ile His Lys Tyr
            20                  25                  30

<210> SEQ ID NO 144

```
<211> LENGTH: 31
<212> TYPE: PRT
<213> ORGANISM: Homo sapiens

<400> SEQUENCE: 144

Glu Glu Leu Glu Ala Glu Cys Phe Pro Val Lys Pro His Asn Lys Ser
1               5                   10                  15

Phe Ala His Ile Leu Glu Leu Val Lys Glu Gly Ser Ser Cys Pro
            20                  25                  30

<210> SEQ ID NO 145
<211> LENGTH: 31
<212> TYPE: PRT
<213> ORGANISM: Homo sapiens

<400> SEQUENCE: 145

Gln Gly Gln Met Pro Val Lys Gly His Ile Ser Ile Arg Ser Lys Ser
1               5                   10                  15

Ala Pro Leu Pro Ser Ala Ala Ala His Gln Gln Leu Tyr Gly
            20                  25                  30

<210> SEQ ID NO 146
<211> LENGTH: 31
<212> TYPE: PRT
<213> ORGANISM: Homo sapiens

<400> SEQUENCE: 146

Pro Arg Pro Pro Leu Gly Ser Ser Leu Ser Pro Trp Trp Arg Ser Ser
1               5                   10                  15

Leu Thr Tyr Phe Gln Gln Gln Leu Lys Pro Gly Lys Glu Asp Lys
            20                  25                  30

<210> SEQ ID NO 147
<211> LENGTH: 31
<212> TYPE: PRT
<213> ORGANISM: Homo sapiens

<400> SEQUENCE: 147

Ser Pro Arg Pro Pro Leu Gly Ser Ser Leu Ser Pro Trp Trp Arg Ser
1               5                   10                  15

Ser Leu Thr Tyr Phe Gln Gln Gln Leu Lys Pro Gly Lys Glu Asp
            20                  25                  30

<210> SEQ ID NO 148
<211> LENGTH: 31
<212> TYPE: PRT
<213> ORGANISM: Homo sapiens

<400> SEQUENCE: 148

Arg Arg Asp Asp Pro Ala Ala Arg Met Ser Arg Ser Ser Gly Arg Ser
1               5                   10                  15

Gly Ser Met Asp Pro Ser Gly Ala His Pro Ser Val Arg Gln Thr
            20                  25                  30

<210> SEQ ID NO 149
<211> LENGTH: 31
<212> TYPE: PRT
<213> ORGANISM: Homo sapiens

<400> SEQUENCE: 149

Gly Leu Lys Asn Gln Lys Pro Val Pro Ala Val Pro Gln Lys Ser
1               5                   10                  15
```

Gly Thr Ser Gly Val Pro Pro Met Ala Gly Gly Lys Lys Pro Ser
            20                  25                  30

<210> SEQ ID NO 150
<211> LENGTH: 31
<212> TYPE: PRT
<213> ORGANISM: Homo sapiens

<400> SEQUENCE: 150

Tyr Phe Ala Asp Val Ser Pro Leu Arg Ala Thr Ser Pro Ser Lys Ser
1               5                   10                  15

Val Ala His Gly Gln Ala Pro Glu Met Pro Leu Val Lys Lys Lys
            20                  25                  30

<210> SEQ ID NO 151
<211> LENGTH: 31
<212> TYPE: PRT
<213> ORGANISM: Homo sapiens

<400> SEQUENCE: 151

Gly Glu Tyr Pro Pro Gln Leu Ser Tyr Thr Glu Leu Ala Ala Lys Ser
1               5                   10                  15

Gly Gly Leu Ala Leu Pro Tyr Phe Asn Gly Thr Gly Val Gln
            20                  25                  30

<210> SEQ ID NO 152
<211> LENGTH: 19
<212> TYPE: PRT
<213> ORGANISM: Homo sapiens

<400> SEQUENCE: 152

Met Gln Arg Ser Ile Met Ser Phe Phe His Pro Lys Lys Glu Gly Lys
1               5                   10                  15

Ala Lys Lys

<210> SEQ ID NO 153
<211> LENGTH: 31
<212> TYPE: PRT
<213> ORGANISM: Homo sapiens

<400> SEQUENCE: 153

Val Lys Gly Ala Ser Phe Val Thr Ser Thr Asn Pro Arg Lys Phe Ser
1               5                   10                  15

Gly Phe Ser Ala Lys Pro Asn Asn Ser Gly Glu Ala Pro Ser Ser
            20                  25                  30

<210> SEQ ID NO 154
<211> LENGTH: 31
<212> TYPE: PRT
<213> ORGANISM: Homo sapiens

<400> SEQUENCE: 154

Lys Leu Thr Thr Thr Gly Gln Val Thr Ser Pro Val Lys Gly Ala Ser
1               5                   10                  15

Phe Val Thr Ser Thr Asn Pro Arg Lys Phe Ser Gly Phe Ser Ala
            20                  25                  30

<210> SEQ ID NO 155
<211> LENGTH: 31
<212> TYPE: PRT
<213> ORGANISM: Homo sapiens

<400> SEQUENCE: 155

```
Glu Lys Arg Lys Lys Asn Ala Pro Lys Glu Ala Ser Arg Leu Lys Ser
1               5                   10                  15

Ile Leu Lys Leu Asp Gly Asp Val Leu Met Lys Asp Val Gln Glu
            20                  25                  30
```

<210> SEQ ID NO 156
<211> LENGTH: 31
<212> TYPE: PRT
<213> ORGANISM: Homo sapiens

<400> SEQUENCE: 156

```
Ser Gly Ser Ser Ala Ser Ser Val Thr Val Thr Arg Ser Tyr Arg Ser
1               5                   10                  15

Val Gly Gly Ser Gly Gly Gly Ser Phe Gly Asp Asn Leu Val Thr
            20                  25                  30
```

<210> SEQ ID NO 157
<211> LENGTH: 27
<212> TYPE: PRT
<213> ORGANISM: Homo sapiens

<400> SEQUENCE: 157

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr
            20                  25
```

<210> SEQ ID NO 158
<211> LENGTH: 31
<212> TYPE: PRT
<213> ORGANISM: Homo sapiens

<400> SEQUENCE: 158

```
Lys Thr Glu Gly Lys Pro Ala Glu Val Lys Met Thr Ala Lys Ser
1               5                   10                  15

Val Pro Ala Asp Leu Ser Arg Pro Lys Ser Thr Ser Thr Ser Ser
            20                  25                  30
```

<210> SEQ ID NO 159
<211> LENGTH: 31
<212> TYPE: PRT
<213> ORGANISM: Homo sapiens

<400> SEQUENCE: 159

```
Leu Pro Lys His Val Asp Ser Ile Ile Asn Lys Arg Leu Ser Lys Ser
1               5                   10                  15

Ser Ala Thr Leu Trp Asn Ser Pro Ser Arg Asn Arg Ser Leu Gln
            20                  25                  30
```

<210> SEQ ID NO 160
<211> LENGTH: 31
<212> TYPE: PRT
<213> ORGANISM: Homo sapiens

<400> SEQUENCE: 160

```
Ser Leu Val Ala Pro Ala Leu Asn Lys Pro Lys Pro Leu Thr Ser
1               5                   10                  15

Ser Ser Ala Ala Pro Gln Arg Pro Ile Ser Thr Gln Arg Thr Ala
            20                  25                  30
```

<210> SEQ ID NO 161

```
<211> LENGTH: 31
<212> TYPE: PRT
<213> ORGANISM: Homo sapiens

<400> SEQUENCE: 161

Gly Gly Gly Ala Pro Arg Arg Glu Pro Val Pro Phe Pro Ser Gly Ser
1               5                   10                  15

Ala Gly Pro Gly Pro Arg Gly Pro Arg Ala Thr Glu Ser Gly Lys
            20                  25                  30

<210> SEQ ID NO 162
<211> LENGTH: 31
<212> TYPE: PRT
<213> ORGANISM: Homo sapiens

<400> SEQUENCE: 162

Leu Lys Gly Ile Pro Ile Lys Lys Thr Lys Gly Cys Arg Lys Ser
1               5                   10                  15

Cys Ser Gly Phe Val Gln Ser Asp Ser Lys Arg Glu Ser Val Cys
            20                  25                  30

<210> SEQ ID NO 163
<211> LENGTH: 31
<212> TYPE: PRT
<213> ORGANISM: Homo sapiens

<400> SEQUENCE: 163

Met Pro Pro Ser Ser Ser Ser Glu Leu Gln Glu Ser Arg Gly Leu Ser
1               5                   10                  15

Asn Phe Thr Ser Thr His Leu Leu Lys Glu Asp Glu Gly Val
            20                  25                  30

<210> SEQ ID NO 164
<211> LENGTH: 31
<212> TYPE: PRT
<213> ORGANISM: Homo sapiens

<400> SEQUENCE: 164

Tyr Lys Lys Leu Ser Ala Lys Arg Ala Asp Leu Gln Ser Thr Phe Ser
1               5                   10                  15

Gly Gly Arg Ile Pro Lys Lys Phe Ala Arg Gly Thr Ser Leu
            20                  25                  30

<210> SEQ ID NO 165
<211> LENGTH: 31
<212> TYPE: PRT
<213> ORGANISM: Homo sapiens

<400> SEQUENCE: 165

Asn Arg Gln Ala Thr Phe Ser Gly Arg Thr Lys Ser Ser Tyr Lys Ser
1               5                   10                  15

Ile Leu Pro Tyr Pro Val Ser Pro Lys Gln Lys Tyr Ser His Val
            20                  25                  30

<210> SEQ ID NO 166
<211> LENGTH: 31
<212> TYPE: PRT
<213> ORGANISM: Homo sapiens

<400> SEQUENCE: 166

Asp Val Lys Ser Gln Lys Glu Asn Val Leu Gln Tyr Cys Arg Lys Ser
1               5                   10                  15
```

Gly Leu Gln Thr Asp Tyr Ala Thr Glu Lys Glu Ser Ala Asp Gly
            20                  25                  30

<210> SEQ ID NO 167
<211> LENGTH: 31
<212> TYPE: PRT
<213> ORGANISM: Homo sapiens

<400> SEQUENCE: 167

Pro Asn Thr Pro Leu Lys Arg Gly Glu Ala Pro Thr Lys Arg Lys Ser
1               5                   10                  15

Leu Val Met His Thr Pro Pro Val Leu Lys Lys Ile Ile Lys Glu
            20                  25                  30

<210> SEQ ID NO 168
<211> LENGTH: 31
<212> TYPE: PRT
<213> ORGANISM: Homo sapiens

<400> SEQUENCE: 168

Glu Ile Ser Ser Val Lys Leu Val Ser Arg Tyr Gly Glu Leu Lys Ser
1               5                   10                  15

Val Pro Thr Thr Gln Cys Leu Asp Asn Ser Lys Asn Glu Ser
            20                  25                  30

<210> SEQ ID NO 169
<211> LENGTH: 31
<212> TYPE: PRT
<213> ORGANISM: Homo sapiens

<400> SEQUENCE: 169

Arg Ser Gln His Asp Ile Leu Gln Met Ile Cys Ser Lys Arg Arg Ser
1               5                   10                  15

Gly Ala Ser Glu Ala Asn Leu Ile Val Ala Lys Ser Trp Ala Asp
            20                  25                  30

<210> SEQ ID NO 170
<211> LENGTH: 31
<212> TYPE: PRT
<213> ORGANISM: Homo sapiens

<400> SEQUENCE: 170

Ser Ala Lys Lys Arg Lys Lys Ser Ser Ser Glu Ala Leu Phe Lys Ser
1               5                   10                  15

Phe Ser Ser Ala Pro Pro Leu Ile Leu Thr Cys Ser Ala Asp Lys
            20                  25                  30

<210> SEQ ID NO 171
<211> LENGTH: 31
<212> TYPE: PRT
<213> ORGANISM: Homo sapiens

<400> SEQUENCE: 171

Lys Glu His Lys Glu Lys Pro Ser Lys Asp Ser Arg Glu His Lys Ser
1               5                   10                  15

Ala Phe Lys Glu Pro Ser Arg Asp His Asn Lys Ser Ser Lys Glu
            20                  25                  30

<210> SEQ ID NO 172
<211> LENGTH: 20
<212> TYPE: PRT
<213> ORGANISM: Homo sapiens -continued

<400> SEQUENCE: 172

Met Pro Ala Arg Ser Gly Ala Gln Phe Cys Arg Arg Met Gly Gln Lys
1               5                   10                  15

Lys Gln Arg Pro
            20

<210> SEQ ID NO 173
<211> LENGTH: 31
<212> TYPE: PRT
<213> ORGANISM: Homo sapiens

<400> SEQUENCE: 173

Arg Glu Arg Cys Leu Gly Pro Thr Thr Pro Gly Pro Tyr Arg Ser
1               5                   10                  15

Ile Tyr Phe Ser Ser Pro Lys Gly His Leu Thr Arg Leu Gly Leu
            20                  25                  30

<210> SEQ ID NO 174
<211> LENGTH: 31
<212> TYPE: PRT
<213> ORGANISM: Homo sapiens

<400> SEQUENCE: 174

Ala Thr Ser Ile Ser Ser Glu Thr Lys Asn Thr Leu Arg Ala Phe Ser
1               5                   10                  15

Ala Pro Gln Asn Ser Glu Ser Gln Ala His Val Ser Gly Gly Gly
            20                  25                  30

<210> SEQ ID NO 175
<211> LENGTH: 31
<212> TYPE: PRT
<213> ORGANISM: Homo sapiens

<400> SEQUENCE: 175

Glu Glu Tyr Ile Pro Leu Asp Ser Asp Thr Val Ser Thr Thr Arg Ser
1               5                   10                  15

Gly Ala Ile Phe Thr Lys Ala Tyr Gln Arg Met Val Leu Asp Ala
            20                  25                  30

<210> SEQ ID NO 176
<211> LENGTH: 31
<212> TYPE: PRT
<213> ORGANISM: Homo sapiens

<400> SEQUENCE: 176

Tyr Leu Glu Thr His Pro Arg Pro Lys Pro Asp Pro Val Lys Ser
1               5                   10                  15

Val Ser Ser Val Leu Ser Ser Leu Thr Pro Ala Lys Val Ala Pro
            20                  25                  30

<210> SEQ ID NO 177
<211> LENGTH: 31
<212> TYPE: PRT
<213> ORGANISM: Homo sapiens

<400> SEQUENCE: 177

His Tyr Gly Leu Ser Asp Ser Arg Lys Arg Thr Arg Thr Gly Arg Ser
1               5                   10                  15

Trp Pro Ala Ala Ile Pro His Leu Arg Arg Arg Gly Arg Leu
            20                  25                  30

<210> SEQ ID NO 178
<211> LENGTH: 31
<212> TYPE: PRT
<213> ORGANISM: Homo sapiens

<400> SEQUENCE: 178

Ser Arg Glu Val Ser Asn Gly Ile Glu Lys Lys Gly Lys Lys Ser
1               5                   10                  15

Val Gly Arg Pro Pro Gly Pro Tyr Thr Arg Lys Met Ile Gln Lys
            20                  25                  30

<210> SEQ ID NO 179
<211> LENGTH: 31
<212> TYPE: PRT
<213> ORGANISM: Homo sapiens

<400> SEQUENCE: 179

Pro Pro Met Phe Leu Cys Ile Lys Val Gly Lys Pro Met Arg Lys Ser
1               5                   10                  15

Phe Ala Thr His Thr Ala Ala Met Val Gln Gln Tyr Gly Lys Arg
            20                  25                  30

<210> SEQ ID NO 180
<211> LENGTH: 31
<212> TYPE: PRT
<213> ORGANISM: Homo sapiens

<400> SEQUENCE: 180

Pro Val Ser Pro Pro Glu Gly Met Thr Glu Pro Gly His Ser Arg Ser
1               5                   10                  15

Ala Val Tyr Pro Leu Leu Tyr Arg Asp Gly Glu Gln Thr Glu Pro
            20                  25                  30

<210> SEQ ID NO 181
<211> LENGTH: 31
<212> TYPE: PRT
<213> ORGANISM: Homo sapiens

<400> SEQUENCE: 181

Asn Ile Ala Arg Lys Gln Pro Met Leu Asp Ala Ala Thr Gly Lys Ser
1               5                   10                  15

Val Trp Gly Ser Leu Ala Val Gln Asn Ser Pro Lys Gly Cys His
            20                  25                  30

<210> SEQ ID NO 182
<211> LENGTH: 31
<212> TYPE: PRT
<213> ORGANISM: Homo sapiens

<400> SEQUENCE: 182

Met Asp Thr Ala Thr Ala Thr Glu Gln Ala Lys Gln Leu Val Lys Ser
1               5                   10                  15

Gly Ala Ile Ser Ala Ile Lys Ala Glu Thr Lys Asn Ser Gly Phe
            20                  25                  30

<210> SEQ ID NO 183
<211> LENGTH: 31
<212> TYPE: PRT
<213> ORGANISM: Homo sapiens

<400> SEQUENCE: 183

Glu Pro Gly Met Pro Ser Pro Thr Thr Leu Lys Lys Ser Glu Lys Ser
1               5                   10                  15

```
Gly Phe Ser Ser Pro Ser Pro Ser Gln Thr Ser Ser Leu Gly Thr
            20                  25                  30
```

<210> SEQ ID NO 184
<211> LENGTH: 31
<212> TYPE: PRT
<213> ORGANISM: Homo sapiens

<400> SEQUENCE: 184

```
Glu Ser Ser Ser Tyr Tyr Ser Met Ser Pro Gly Ala Met Arg Arg Ser
1               5                   10                  15

Leu Pro Ser Thr Ser Ser Thr Ser Ser Thr Lys Arg Leu Lys Ser
            20                  25                  30
```

<210> SEQ ID NO 185
<211> LENGTH: 31
<212> TYPE: PRT
<213> ORGANISM: Homo sapiens

<400> SEQUENCE: 185

```
Pro Thr Tyr Ser Thr Pro Ser Thr Ser Pro Ala Asn Arg Phe Val Ser
1               5                   10                  15

Val Gly Pro Arg Asp Pro Ser Phe Val Asn Ile Pro Gln Gln Thr
            20                  25                  30
```

<210> SEQ ID NO 186
<211> LENGTH: 31
<212> TYPE: PRT
<213> ORGANISM: Homo sapiens

<400> SEQUENCE: 186

```
Ile Thr Val Pro Leu Ser Val Ile Ser Gln Pro Met Lys Gly Lys Ser
1               5                   10                  15

Val Val Thr Ala Pro Ile Ile Lys Gly Asn Leu Gly Ala Asn Leu
            20                  25                  30
```

<210> SEQ ID NO 187
<211> LENGTH: 31
<212> TYPE: PRT
<213> ORGANISM: Homo sapiens

<400> SEQUENCE: 187

```
Pro Phe Val Tyr Leu Ala Ser Lys Met Thr Gln Pro Gln Ser Lys Ser
1               5                   10                  15

Ala Phe Pro Leu Ser Arg Lys Asn Lys Gly Ser Gly Ser Leu Asp
            20                  25                  30
```

<210> SEQ ID NO 188
<211> LENGTH: 31
<212> TYPE: PRT
<213> ORGANISM: Homo sapiens

<400> SEQUENCE: 188

```
Pro Tyr Ser Ser Val Pro Pro Ser Ala Pro Pro Lys Lys Ser
1               5                   10                  15

Leu Gly Thr Gln Pro Pro Lys Lys Ala Val Glu Lys Gln Gln Pro
            20                  25                  30
```

<210> SEQ ID NO 189
<211> LENGTH: 31
<212> TYPE: PRT
<213> ORGANISM: Homo sapiens

```
<400> SEQUENCE: 189

Met Val Ala Thr Thr Lys Pro Lys Ala Thr Lys Ala Leu Ser
1               5                   10                  15

Leu Pro Ala Lys Gln Ala Pro Gln Gly Ser Arg Asp Ser Ser Ser
                20                  25                  30

<210> SEQ ID NO 190
<211> LENGTH: 31
<212> TYPE: PRT
<213> ORGANISM: Homo sapiens

<400> SEQUENCE: 190

Ser Pro Glu Ala Lys Pro Leu Pro Gly Lys Leu Pro Lys Gly Ile Ser
1               5                   10                  15

Ala Gly Ala Val Gln Thr Ala Gly Lys Lys Gly Pro Gln Ser Leu
                20                  25                  30

<210> SEQ ID NO 191
<211> LENGTH: 31
<212> TYPE: PRT
<213> ORGANISM: Homo sapiens

<400> SEQUENCE: 191

Arg Arg Phe Pro Ala Gly Gly Lys Arg Gly Arg Gly Ala Lys Gly Ser
1               5                   10                  15

Gly Arg Pro Leu Pro Gly Arg Lys Arg Gln Pro Trp Pro Pro Pro
                20                  25                  30

<210> SEQ ID NO 192
<211> LENGTH: 31
<212> TYPE: PRT
<213> ORGANISM: Homo sapiens

<400> SEQUENCE: 192

Pro Leu Glu Arg Pro Leu Gly Thr Ala Asp Pro Arg Leu Asp Lys Ser
1               5                   10                  15

Ile Gly Ala Ala Ser Pro Arg Pro Gln Ser Leu Glu Lys Thr Ser
                20                  25                  30

<210> SEQ ID NO 193
<211> LENGTH: 31
<212> TYPE: PRT
<213> ORGANISM: Homo sapiens

<400> SEQUENCE: 193

Trp Tyr Trp Arg Gln Ser Ser Asp Arg Phe Pro Arg His Gln Lys Ser
1               5                   10                  15

Phe Asn Pro Ala Val Lys Asn Ser Tyr Tyr Pro Arg Lys Tyr Asp
                20                  25                  30

<210> SEQ ID NO 194
<211> LENGTH: 31
<212> TYPE: PRT
<213> ORGANISM: Homo sapiens

<400> SEQUENCE: 194

Lys Lys Ala Ala Pro Ala Ser Thr Lys Gln Ala Asp Arg Arg Gln Ser
1               5                   10                  15

Met Ala Phe Ser Ile Leu Asn Thr Pro Lys Lys Leu Gly Asn Ser
                20                  25                  30
```

<210> SEQ ID NO 195
<211> LENGTH: 31
<212> TYPE: PRT
<213> ORGANISM: Homo sapiens

<400> SEQUENCE: 195

Val Glu Glu Pro Asp Ser Ala Asn Ser Ser Phe Tyr Ser Thr Arg Ser
1               5                   10                  15

Ala Pro Ala Ser Gln Ala Ser Leu Arg Ala Thr Ser Ser Thr Gln
            20                  25                  30

<210> SEQ ID NO 196
<211> LENGTH: 31
<212> TYPE: PRT
<213> ORGANISM: Homo sapiens

<400> SEQUENCE: 196

Asn Lys Gly Gly Val Arg Thr Pro Val Pro Arg Gly Arg Leu Ser
1               5                   10                  15

Val Ala Ser Thr Pro Ile Ser Gln Arg Arg Ser Gln Gly Arg Ser
            20                  25                  30

<210> SEQ ID NO 197
<211> LENGTH: 31
<212> TYPE: PRT
<213> ORGANISM: Homo sapiens

<400> SEQUENCE: 197

Ser Val Ala Ser Thr Pro Ile Ser Gln Arg Arg Ser Gln Gly Arg Ser
1               5                   10                  15

Cys Gly Pro Ala Ser Gln Ser Thr Leu Gly Leu Lys Gly Ser Leu
            20                  25                  30

<210> SEQ ID NO 198
<211> LENGTH: 31
<212> TYPE: PRT
<213> ORGANISM: Homo sapiens

<400> SEQUENCE: 198

Ser Ser Gly Asn Arg Asp Ser Lys Val Pro Ser Glu Gly Lys Lys Ser
1               5                   10                  15

Leu Tyr Thr Asp Glu Ser Ser Lys Pro Gly Lys Asn Lys Arg Thr
            20                  25                  30

<210> SEQ ID NO 199
<211> LENGTH: 31
<212> TYPE: PRT
<213> ORGANISM: Homo sapiens

<400> SEQUENCE: 199

Pro Ala Ser Gln Ser Thr Leu Gly Leu Lys Gly Ser Leu Lys Arg Ser
1               5                   10                  15

Ala Ile Ser Ala Ala Lys Thr Gly Val Arg Phe Ser Ala Ala Thr
            20                  25                  30

<210> SEQ ID NO 200
<211> LENGTH: 31
<212> TYPE: PRT
<213> ORGANISM: Homo sapiens

<400> SEQUENCE: 200

Ile Arg Glu Glu Arg Thr Leu Thr Pro Ile Ser Gly Gly Gln Arg Ser

-continued

```
                1               5                  10                 15
Ser Val Val Pro Ser Val Ile Leu Lys Pro Glu Asn Ile Lys Lys
        20                  25                 30

<210> SEQ ID NO 201
<211> LENGTH: 31
<212> TYPE: PRT
<213> ORGANISM: Homo sapiens

<400> SEQUENCE: 201

Ala Ala Ala Ala Ala Ala Ala Gly Ala Ala Gly Gly Arg Gly Ser
1               5                  10                 15
Gly Pro Gly Arg Arg Arg His Leu Val Pro Gly Ala Gly Gly Glu
        20                  25                 30

<210> SEQ ID NO 202
<211> LENGTH: 31
<212> TYPE: PRT
<213> ORGANISM: Homo sapiens

<400> SEQUENCE: 202

Glu Val Lys Ala Glu Pro Val Glu Val Ala Pro Arg Gly Lys Ser
1               5                  10                 15
Gly Ala Ala Leu Ser Lys Lys Ser Lys Gly Gln Val Lys Glu Glu
        20                  25                 30

<210> SEQ ID NO 203
<211> LENGTH: 31
<212> TYPE: PRT
<213> ORGANISM: Homo sapiens

<400> SEQUENCE: 203

Asn Leu Ala Ala Ala Arg Leu Thr Gly Pro Ser His Ser Lys Gly Ser
1               5                  10                 15
Leu Gly Glu Glu Arg Asn Pro Thr Ser Lys Tyr Tyr Arg Asn Lys
        20                  25                 30

<210> SEQ ID NO 204
<211> LENGTH: 31
<212> TYPE: PRT
<213> ORGANISM: Homo sapiens

<400> SEQUENCE: 204

Val Val Leu Tyr Leu Leu Arg Val Cys Leu Ala Met Ala Trp Lys Ser
1               5                  10                 15
Gly Gly Ala Ser His Ser Glu Leu Ile His Asn Leu Arg Lys Asn
        20                  25                 30

<210> SEQ ID NO 205
<211> LENGTH: 31
<212> TYPE: PRT
<213> ORGANISM: Homo sapiens

<400> SEQUENCE: 205

Pro Asn Asn Asn Asn Asn Asn Ser Lys His Thr Gly His Lys Ser
1               5                  10                 15
Ala Cys Val Pro Asn Met Thr Glu Arg Arg Arg Asp Glu Leu Ser
        20                  25                 30

<210> SEQ ID NO 206
<211> LENGTH: 28
<212> TYPE: PRT
```

<213> ORGANISM: Homo sapiens

<400> SEQUENCE: 206

Met Gly Gly Leu Glu Lys Lys Tyr Glu Arg Gly Ser Ala Thr Asn
1               5                   10                  15

Tyr Ile Thr Arg Asn Lys Ala Arg Lys Lys Leu Gln
            20                  25

<210> SEQ ID NO 207
<211> LENGTH: 31
<212> TYPE: PRT
<213> ORGANISM: Homo sapiens

<400> SEQUENCE: 207

Gly Phe Val Ile Gln Glu Gly Ala Glu Pro Phe Pro Val Gly Arg Ser
1               5                   10                  15

Ser Leu Leu Val Gly Asn Leu Lys Lys Tyr Ala Gln Gly Phe
            20                  25                  30

<210> SEQ ID NO 208
<211> LENGTH: 31
<212> TYPE: PRT
<213> ORGANISM: Homo sapiens

<400> SEQUENCE: 208

Lys Ala Gly Ala Ala Thr His Asn Arg Arg Ala Ser Lys Ala Ser
1               5                   10                  15

Leu Pro Pro Leu Thr Lys Asp Thr Lys Lys Gln Pro Thr Gly Thr
            20                  25                  30

<210> SEQ ID NO 209
<211> LENGTH: 27
<212> TYPE: PRT
<213> ORGANISM: Homo sapiens

<400> SEQUENCE: 209

Ala Thr Pro Arg Lys Asp Gly Pro Lys Arg Ser Val Leu Ser Lys Ser
1               5                   10                  15

Val Pro Gly Tyr Lys Val Glu Glu Lys Ser Pro
            20                  25

<210> SEQ ID NO 210
<211> LENGTH: 31
<212> TYPE: PRT
<213> ORGANISM: Homo sapiens

<400> SEQUENCE: 210

Ala Leu Thr Lys Met Glu Pro Pro Lys Lys Gly Lys Ala Thr Lys Ser
1               5                   10                  15

Val Leu Ser Val Pro Asn Lys Asp Val Val His Met Gln Asn Asp
            20                  25                  30

<210> SEQ ID NO 211
<211> LENGTH: 31
<212> TYPE: PRT
<213> ORGANISM: Homo sapiens

<400> SEQUENCE: 211

His Gly Gln Glu Thr Thr Asp Ser Ser Asp Lys Lys Glu Lys Lys Ser
1               5                   10                  15

Phe Ser Leu Glu Glu Lys Ser Lys Ile Ser Lys Asn Arg Val His
            20                  25                  30

<210> SEQ ID NO 212
<211> LENGTH: 31
<212> TYPE: PRT
<213> ORGANISM: Homo sapiens

<400> SEQUENCE: 212

Asp Val Tyr Ala Ala Gly Tyr Ser Tyr Asn Asn Trp Ala Ala Lys Ser
1               5                   10                  15

Leu Ala Pro Ala Pro Leu Ser Thr Lys Ser Phe Thr Phe Phe Asn
            20                  25                  30

<210> SEQ ID NO 213
<211> LENGTH: 31
<212> TYPE: PRT
<213> ORGANISM: Homo sapiens

<400> SEQUENCE: 213

Pro Phe Lys Asn Thr Glu Asn Ile Lys Asn Ser His Leu Lys Lys Ser
1               5                   10                  15

Ala Phe Leu Thr Glu Val Ser Gln Lys Glu Asn Tyr Ala Gly Ala
            20                  25                  30

<210> SEQ ID NO 214
<211> LENGTH: 31
<212> TYPE: PRT
<213> ORGANISM: Homo sapiens

<400> SEQUENCE: 214

Cys Leu Thr Pro Gln Pro Arg Ala Pro Ala Ala Leu Pro Asn Arg Ser
1               5                   10                  15

Leu Ala Val Ala Gly Gly Thr Pro Arg Ala Ala Pro Lys Lys Arg
            20                  25                  30

<210> SEQ ID NO 215
<211> LENGTH: 31
<212> TYPE: PRT
<213> ORGANISM: Homo sapiens

<400> SEQUENCE: 215

Pro Gln Ile Thr Pro Pro Val Met Ile Leu Lys Lys Lys Arg Ser
1               5                   10                  15

Ile Gly Ala Ser Pro Asn Pro Phe Ser Val His Thr Ala Thr Ala
            20                  25                  30

<210> SEQ ID NO 216
<211> LENGTH: 31
<212> TYPE: PRT
<213> ORGANISM: Homo sapiens

<400> SEQUENCE: 216

Pro Ala Glu Val Asp Pro Asp Thr Ile Leu Lys Ala Leu Phe Lys Ser
1               5                   10                  15

Ser Gly Ala Ser Val Thr Thr Gln Pro Thr Glu Phe Lys Ile Lys
            20                  25                  30

<210> SEQ ID NO 217
<211> LENGTH: 31
<212> TYPE: PRT
<213> ORGANISM: Homo sapiens

<400> SEQUENCE: 217

Arg Ala Ala Glu Ile Ser Ala Met Leu Lys Ala Val Thr Gln Lys Ser
1               5                   10                  15

Ser Asn Ser Leu Val Phe Gln Thr Leu Pro Arg His Met Arg Arg
                20                  25                  30

<210> SEQ ID NO 218
<211> LENGTH: 31
<212> TYPE: PRT
<213> ORGANISM: Homo sapiens

<400> SEQUENCE: 218

Thr Leu Ser Ser Gly Phe Val Ala Asp Arg Gly Val Lys His His Ser
1               5                   10                  15

Gly Gly Glu Lys Pro Phe Gln Ala Gln Lys Gln Glu Pro His Pro
                20                  25                  30

<210> SEQ ID NO 219
<211> LENGTH: 18
<212> TYPE: PRT
<213> ORGANISM: Homo sapiens

<400> SEQUENCE: 219

Met Lys Ser Val Ile Tyr His Ala Leu Ser Gln Lys Glu Ala Asn Asp
1               5                   10                  15

Ser Asp

<210> SEQ ID NO 220
<211> LENGTH: 31
<212> TYPE: PRT
<213> ORGANISM: Homo sapiens

<400> SEQUENCE: 220

Arg Gln Pro Glu Tyr Arg Asp Met Arg Asp Gly Phe Arg Lys Ser
1               5                   10                  15

Phe Tyr Ser Ser His Tyr Ala Arg Glu Arg Ser Pro Tyr Lys Arg
                20                  25                  30

<210> SEQ ID NO 221
<211> LENGTH: 31
<212> TYPE: PRT
<213> ORGANISM: Homo sapiens

<400> SEQUENCE: 221

Glu Arg Lys Thr Gln Leu Lys Val Ala Pro Glu Thr Lys Val Lys Ser
1               5                   10                  15

Ser Gln Pro Gln Ala Gly Ser Gln Gly Pro Gln Thr Phe Arg Gln
                20                  25                  30

<210> SEQ ID NO 222
<211> LENGTH: 31
<212> TYPE: PRT
<213> ORGANISM: Homo sapiens

<400> SEQUENCE: 222

Ser Gly Pro Leu Met Lys Lys His Arg Arg Asn Gly Leu Ser Arg Ser
1               5                   10                  15

Ser Gly Ala Gln Pro Ala Ser Leu Pro Thr Thr Ser Gln Arg Lys
                20                  25                  30

<210> SEQ ID NO 223
<211> LENGTH: 31
<212> TYPE: PRT

-continued

<213> ORGANISM: Homo sapiens

<400> SEQUENCE: 223

Thr Thr Thr Thr Pro Ser Pro Ser Ala Ile Lys Ala Ala Lys Ser
1               5                   10                  15

Ala Ala Leu Gln Val Thr Lys Gln Ile Thr Gln Glu Glu Asp Asp
            20                  25                  30

<210> SEQ ID NO 224
<211> LENGTH: 31
<212> TYPE: PRT
<213> ORGANISM: Homo sapiens

<400> SEQUENCE: 224

Phe Ala His Lys Arg Ser Glu Arg Leu Gln Arg Ala Pro Leu Lys Ser
1               5                   10                  15

Val Gly Pro Asp Phe Gly Lys Lys Arg Leu Gly Leu Pro Gly Asp
            20                  25                  30

<210> SEQ ID NO 225
<211> LENGTH: 31
<212> TYPE: PRT
<213> ORGANISM: Homo sapiens

<400> SEQUENCE: 225

Lys Lys Tyr Ser Ser Leu Asn Leu Phe Asp Thr Tyr Lys Gly Lys Ser
1               5                   10                  15

Leu Glu Ile Gln Lys Pro Ala Val Ala Pro Arg His Gly Leu Gln
            20                  25                  30

<210> SEQ ID NO 226
<211> LENGTH: 31
<212> TYPE: PRT
<213> ORGANISM: Homo sapiens

<400> SEQUENCE: 226

Glu Arg Arg Glu Lys Leu Lys Thr Ser Arg Asp Lys Leu Arg Lys Ser
1               5                   10                  15

Phe Thr Pro Asp His Val Val Tyr Ala Arg Ser Lys Thr Ala Val
            20                  25                  30

<210> SEQ ID NO 227
<211> LENGTH: 31
<212> TYPE: PRT
<213> ORGANISM: Homo sapiens

<400> SEQUENCE: 227

Arg Gln Phe Val Asp Gly Pro Pro Gly Pro Val Lys Lys Thr Arg Ser
1               5                   10                  15

Ile Gly Ser Ala Val Asp Gln Gly Asn Glu Ser Ile Val Ala Lys
            20                  25                  30

<210> SEQ ID NO 228
<211> LENGTH: 19
<212> TYPE: PRT
<213> ORGANISM: Homo sapiens

<400> SEQUENCE: 228

Met Arg Arg Ser Ala Ala Pro Ser Gln Leu Gln Gly Asn Ser Phe Lys
1               5                   10                  15

Lys Pro Lys

```
<210> SEQ ID NO 229
<211> LENGTH: 31
<212> TYPE: PRT
<213> ORGANISM: Homo sapiens

<400> SEQUENCE: 229

Gly Ser Lys Leu Ser Asp Arg Pro Leu His Ala Leu Lys Arg Lys Ser
1               5                   10                  15

Ala Phe Met Ala Pro Val Pro Thr Lys Lys Arg Asn Leu Val Leu
            20                  25                  30

<210> SEQ ID NO 230
<211> LENGTH: 31
<212> TYPE: PRT
<213> ORGANISM: Homo sapiens

<400> SEQUENCE: 230

Gln Ser Ala Pro Ser Thr Val His Gly Gly Ile Gln Lys Met Met Ser
1               5                   10                  15

Lys Pro Gln Thr Ser Gly Ala Tyr Val Leu Asn Lys Val Pro Val
            20                  25                  30

<210> SEQ ID NO 231
<211> LENGTH: 31
<212> TYPE: PRT
<213> ORGANISM: Homo sapiens

<400> SEQUENCE: 231

Pro Ala Gly Pro His Ala His Ser Pro Val Pro Pro Gly Ile Lys Ser
1               5                   10                  15

Ile Gln Gly Ile His Pro Ala Lys Lys Ala Ile Met His Gly Arg
            20                  25                  30

<210> SEQ ID NO 232
<211> LENGTH: 31
<212> TYPE: PRT
<213> ORGANISM: Homo sapiens

<400> SEQUENCE: 232

Gln Gly Leu Asn Phe Thr Ser Lys Thr Ala Glu Gly His Pro Lys Ser
1               5                   10                  15

Leu Phe Ile Gly Glu Lys Ala Val Leu Leu Lys Thr Lys Lys Lys
            20                  25                  30

<210> SEQ ID NO 233
<211> LENGTH: 31
<212> TYPE: PRT
<213> ORGANISM: Homo sapiens

<400> SEQUENCE: 233

Gly Gly Ser Tyr Arg Asp Ser Tyr Glu Ser Tyr Gly Asn Ser Arg Ser
1               5                   10                  15

Ala Pro Pro Thr Arg Gly Pro Pro Ser Tyr Gly Ser Ser
            20                  25                  30

<210> SEQ ID NO 234
<211> LENGTH: 31
<212> TYPE: PRT
<213> ORGANISM: Homo sapiens

<400> SEQUENCE: 234

Lys Lys Ser Gly Gly Ser Gly Glu Arg Asn Ser Thr Pro Leu Lys Ser
```

```
                1               5                  10                  15
Ala Ala Ala Met Glu Ser Ala Gln Ser Ser Arg Leu Pro Trp Glu
            20                  25                  30

<210> SEQ ID NO 235
<211> LENGTH: 26
<212> TYPE: PRT
<213> ORGANISM: Homo sapiens

<400> SEQUENCE: 235

Val Ser Lys Ser Ala His Ser Leu Gln Pro Ser Ile Ser Gln Lys Ser
1               5                  10                  15

Val Phe Gln Met Phe Gln Arg Cys Thr Lys
            20                  25

<210> SEQ ID NO 236
<211> LENGTH: 30
<212> TYPE: PRT
<213> ORGANISM: Homo sapiens

<400> SEQUENCE: 236

Met Ala Pro Ala Lys Lys Gly Gly Glu Lys Lys Lys Gly Arg Ser Ala
1               5                  10                  15

Ile Asn Glu Val Val Thr Arg Glu Tyr Thr Ile Asn Ile His
            20                  25                  30

<210> SEQ ID NO 237
<211> LENGTH: 31
<212> TYPE: PRT
<213> ORGANISM: Homo sapiens

<400> SEQUENCE: 237

Cys Leu Glu Glu Lys Pro Gly Asp Arg Gly Lys Leu Ala Arg Ala Ser
1               5                  10                  15

Gly Asn Tyr Ala Thr Val Ile Ser His Asn Pro Glu Thr Lys Lys
            20                  25                  30

<210> SEQ ID NO 238
<211> LENGTH: 31
<212> TYPE: PRT
<213> ORGANISM: Homo sapiens

<400> SEQUENCE: 238

Gln Ala Gln Lys Leu Arg Asn Ser Ala Lys Gly Lys Val Pro Lys Ser
1               5                  10                  15

Ala Leu Asp Glu Tyr Arg Lys Arg Glu Cys Arg Asp His Leu Arg
            20                  25                  30

<210> SEQ ID NO 239
<211> LENGTH: 31
<212> TYPE: PRT
<213> ORGANISM: Homo sapiens

<400> SEQUENCE: 239

Phe Met Ala Phe Asn Arg Gly Lys Arg Glu Gly Phe Phe Leu Lys Ser
1               5                  10                  15

Val Glu Asn Ala Pro Leu Ala Lys Arg Arg Lys Gln Lys Leu Arg
            20                  25                  30

<210> SEQ ID NO 240
<211> LENGTH: 31
<212> TYPE: PRT
```

<213> ORGANISM: Homo sapiens

<400> SEQUENCE: 240

Gly Leu Asn Arg Asn Met Thr Ala Glu Phe Lys Lys Thr Asp Lys Ser
1               5                   10                  15

Ile Leu Val Ser Pro Thr Gly Pro Ser Arg Val Ala Phe Asp Pro
            20                  25                  30

<210> SEQ ID NO 241
<211> LENGTH: 31
<212> TYPE: PRT
<213> ORGANISM: Homo sapiens

<400> SEQUENCE: 241

Asp Thr Pro Phe Leu Pro Lys Pro Leu Phe Phe Arg Arg Ala Lys Ser
1               5                   10                  15

Ser Thr Ala Thr His Pro Pro Gly Pro Ala Val Gln Leu Asn Lys
            20                  25                  30

<210> SEQ ID NO 242
<211> LENGTH: 31
<212> TYPE: PRT
<213> ORGANISM: Homo sapiens

<400> SEQUENCE: 242

Glu Glu Arg Ala Glu Ala Leu Asp Arg Gln Arg Thr Lys Asn Ile Ser
1               5                   10                  15

Ala Ile Ser Tyr Ile Asn Gln Arg Asn Arg Glu Trp Asn Ile Val
            20                  25                  30

<210> SEQ ID NO 243
<211> LENGTH: 29
<212> TYPE: PRT
<213> ORGANISM: Homo sapiens

<400> SEQUENCE: 243

Ile Thr Ser Lys Ala Pro Pro Ala Lys Asp Gly Ala Pro Arg Arg Ser
1               5                   10                  15

Leu Asn Leu Glu Asp Tyr Lys Lys Arg Arg Gly Leu Ile
            20                  25

<210> SEQ ID NO 244
<211> LENGTH: 31
<212> TYPE: PRT
<213> ORGANISM: Homo sapiens

<400> SEQUENCE: 244

Glu Thr Thr Val Gln Lys Val Ala Arg Val Lys Ala Pro Asn Lys Ser
1               5                   10                  15

Leu Pro Ser Ala Val Tyr Cys Ile Glu Asp Lys Met Ala Ile Asp
            20                  25                  30

<210> SEQ ID NO 245
<211> LENGTH: 31
<212> TYPE: PRT
<213> ORGANISM: Homo sapiens

<400> SEQUENCE: 245

Tyr Lys Asp Gln Asn Glu Asn Arg Trp Gln Asn Arg Lys Pro Leu Ser
1               5                   10                  15

Gly Asn Ser Asn Ser Ser Gly Ser Glu Ser Phe Lys Phe Val Glu
            20                  25                  30

<210> SEQ ID NO 246
<211> LENGTH: 31
<212> TYPE: PRT
<213> ORGANISM: Homo sapiens

<400> SEQUENCE: 246

Lys Lys Glu Ala Gly Gly Gly Val Gly Pro Gly Ala Lys Ser
1               5                   10                  15

Ala Ala Gln Ala Ala Gln Thr Asn Ser Asn Ala Ala Gly Lys
            20                  25                  30

<210> SEQ ID NO 247
<211> LENGTH: 31
<212> TYPE: PRT
<213> ORGANISM: Homo sapiens

<400> SEQUENCE: 247

Ser Arg Gly Lys Arg Glu Phe Asp Arg His Ser Gly Ser Asp Arg Ser
1               5                   10                  15

Ser Phe Ser His Tyr Ser Gly Leu Lys His Glu Asp Lys Arg Gly
            20                  25                  30

<210> SEQ ID NO 248
<211> LENGTH: 31
<212> TYPE: PRT
<213> ORGANISM: Homo sapiens

<400> SEQUENCE: 248

Asn Asn Arg Ala Tyr Ser Lys Asn Lys Lys Gly Gln Val Lys Arg Ser
1               5                   10                  15

Ile Phe Ala Ser Pro Glu Ser Val Thr Gly Lys Val Gly Val Gly
            20                  25                  30

<210> SEQ ID NO 249
<211> LENGTH: 31
<212> TYPE: PRT
<213> ORGANISM: Homo sapiens

<400> SEQUENCE: 249

Ser Ala Asn Met Met Lys Lys Arg Thr Ser His Lys Lys His Arg Ser
1               5                   10                  15

Ser Val Gly Pro Ser Lys Pro Val Ser Gln Pro Arg Arg Asn Ile
            20                  25                  30

<210> SEQ ID NO 250
<211> LENGTH: 31
<212> TYPE: PRT
<213> ORGANISM: Homo sapiens

<400> SEQUENCE: 250

Ser Gly Pro Gly Arg Ser Ile Ser Gly Ser Ile Pro Ala Gly Arg Thr
1               5                   10                  15

Val Ser Asn Ser Val Pro Gly Arg Pro Val Ser Ser Leu Gly Pro
            20                  25                  30

<210> SEQ ID NO 251
<211> LENGTH: 31
<212> TYPE: PRT
<213> ORGANISM: Homo sapiens

<400> SEQUENCE: 251

-continued

Gln Glu Pro Pro Lys Val Glu Ser Lys Pro Lys Val Pro Leu Lys Ser
1               5                   10                  15

Ala Pro Pro Pro Met Asn Phe Thr Asp Leu Leu Arg Leu Ala Glu
            20                  25                  30

<210> SEQ ID NO 252
<211> LENGTH: 31
<212> TYPE: PRT
<213> ORGANISM: Homo sapiens

<400> SEQUENCE: 252

Ala Ser Arg Thr Gln Lys Ser Ala Val Glu His Lys Ala Lys Lys Ser
1               5                   10                  15

Leu Ser His Pro Ser His Ser Arg Pro Gly Pro Met Val Thr Pro
            20                  25                  30

<210> SEQ ID NO 253
<211> LENGTH: 31
<212> TYPE: PRT
<213> ORGANISM: Homo sapiens

<400> SEQUENCE: 253

Arg Leu Val Gly Thr Thr Asn Gln Gly Asp Gln Arg Ile Leu Arg Ser
1               5                   10                  15

Ser Ala Pro Pro Ser Leu Ala Gly Pro Ala Val Ser His Arg Gly
            20                  25                  30

<210> SEQ ID NO 254
<211> LENGTH: 26
<212> TYPE: PRT
<213> ORGANISM: Homo sapiens

<400> SEQUENCE: 254

His His Lys Lys Glu Lys Lys Arg Lys Lys Glu Lys His Ser Ser
1               5                   10                  15

Thr Pro Asn Ser Ser Glu Phe Ser Arg Lys
            20                  25

<210> SEQ ID NO 255
<211> LENGTH: 17
<212> TYPE: PRT
<213> ORGANISM: Homo sapiens

<400> SEQUENCE: 255

Met Ser Gly Gly Gly Val Ile Arg Gly Pro Ala Gly Asn Asn Asp Cys
1               5                   10                  15

Arg

<210> SEQ ID NO 256
<211> LENGTH: 31
<212> TYPE: PRT
<213> ORGANISM: Homo sapiens

<400> SEQUENCE: 256

Asn Arg Ala Ala Arg Thr Thr Lys Gln Arg Arg Ser Thr Asn Lys Ser
1               5                   10                  15

Ala Phe Ser Ile Asn His Val Ser Arg Gln Val Thr Ser Ser Gly
            20                  25                  30

<210> SEQ ID NO 257
<211> LENGTH: 31
<212> TYPE: PRT

```
<213> ORGANISM: Homo sapiens

<400> SEQUENCE: 257

Arg Pro Gln Pro Leu Thr Phe Ser Pro Ser Trp Gly Gly Pro Lys Ser
1               5                   10                  15

Leu Pro Val Pro Ala Pro Pro Gly Glu Val Gly Thr Thr Pro Ser
            20                  25                  30

<210> SEQ ID NO 258
<211> LENGTH: 31
<212> TYPE: PRT
<213> ORGANISM: Homo sapiens

<400> SEQUENCE: 258

Arg Lys Arg Asp Lys Gln Pro Gly Glu Thr Asn Gly Glu Lys Lys Ser
1               5                   10                  15

Ala Phe Ala Thr Tyr Lys Val Lys Ala Ala Ser Ala His Pro
            20                  25                  30

<210> SEQ ID NO 259
<211> LENGTH: 31
<212> TYPE: PRT
<213> ORGANISM: Homo sapiens

<400> SEQUENCE: 259

Arg Asp Lys Ala Ser Gly Asp Val Lys Glu Lys Gly Lys Gly Ser
1               5                   10                  15

Leu Gly Ser Gln Gly Ala Lys Asp Glu Pro Glu Glu Glu Leu Gln
            20                  25                  30

<210> SEQ ID NO 260
<211> LENGTH: 31
<212> TYPE: PRT
<213> ORGANISM: Homo sapiens

<400> SEQUENCE: 260

Ser Asp Gly Glu Val Pro Thr Ala Val Ala Pro Ala Gln Glu Lys Ser
1               5                   10                  15

Leu Gly Asn Ile Leu Gln Ala Lys Pro Thr Ser Pro Ala Lys
            20                  25                  30

<210> SEQ ID NO 261
<211> LENGTH: 31
<212> TYPE: PRT
<213> ORGANISM: Homo sapiens

<400> SEQUENCE: 261

Gly Lys Gly Leu Gln Val Lys Ala Ala Ser Val Pro Val Lys Gly Ser
1               5                   10                  15

Leu Gly Gln Gly Thr Ala Pro Val Leu Pro Gly Lys Thr Gly Pro
            20                  25                  30

<210> SEQ ID NO 262
<211> LENGTH: 31
<212> TYPE: PRT
<213> ORGANISM: Homo sapiens

<400> SEQUENCE: 262

Arg Ser Ala Lys Lys Arg Arg Lys Asn Ala Leu Ile Arg His Lys Ser
1               5                   10                  15

Ile Ala Glu Val Ser Gln Asn Leu Arg Gln Ile Glu Ile Pro Lys
            20                  25                  30
```

<210> SEQ ID NO 263
<211> LENGTH: 31
<212> TYPE: PRT
<213> ORGANISM: Homo sapiens

<400> SEQUENCE: 263

Asp Asn Phe Lys Lys Asn Lys Gly Tyr His Lys Leu Leu Thr Lys Ser
1               5                   10                  15

Val Ala Glu Thr Pro Val His Lys Gln Ile Ser Lys Arg Leu Leu
            20                  25                  30

<210> SEQ ID NO 264
<211> LENGTH: 31
<212> TYPE: PRT
<213> ORGANISM: Homo sapiens

<400> SEQUENCE: 264

Gly Tyr Tyr Lys Asp Ile Val Glu Asn Ile Cys Gly Arg Glu Lys Ser
1               5                   10                  15

Gly Ile Gln Pro Leu Cys Pro Glu Arg Ser His Ile Ser Asp Gln
            20                  25                  30

<210> SEQ ID NO 265
<211> LENGTH: 31
<212> TYPE: PRT
<213> ORGANISM: Homo sapiens

<400> SEQUENCE: 265

Val Arg Ile Asn Leu Gln Gln Gln Pro Pro Leu Gln Ile Lys Ser
1               5                   10                  15

Val Pro Leu Pro Thr Leu Lys Met Gln Thr Thr Leu Val Pro Pro
            20                  25                  30

<210> SEQ ID NO 266
<211> LENGTH: 31
<212> TYPE: PRT
<213> ORGANISM: Homo sapiens

<400> SEQUENCE: 266

Phe Lys Lys Leu Ala Leu Ala Gly Ile Gly Gln Pro Val Lys Lys Ser
1               5                   10                  15

Val Ser Gln Val Thr Lys Ser Val Asp Phe His Phe Arg Thr Asp
            20                  25                  30

<210> SEQ ID NO 267
<211> LENGTH: 31
<212> TYPE: PRT
<213> ORGANISM: Homo sapiens

<400> SEQUENCE: 267

Ala Ala Arg Phe Ser Pro Lys Val Ser Leu Pro Lys Thr Lys Leu Ser
1               5                   10                  15

Leu Pro Gly Ser Ser Lys Ser Glu Thr Ser Lys Pro Gly Pro Ser
            20                  25                  30

<210> SEQ ID NO 268
<211> LENGTH: 31
<212> TYPE: PRT
<213> ORGANISM: Homo sapiens

<400> SEQUENCE: 268

Val Asp Asn Gln Ala Lys Ser Pro Thr Thr Gln Ser Pro Lys Ser
1               5                   10                  15

Ser Phe Leu Ala Ser Leu Asn Pro Lys Thr Trp Gly Arg Leu Ser
                20                  25                  30

<210> SEQ ID NO 269
<211> LENGTH: 31
<212> TYPE: PRT
<213> ORGANISM: Homo sapiens

<400> SEQUENCE: 269

Glu Thr Lys Gly Phe Leu Gln Gly Ala Pro Ala Gly Gly Glu Lys Ser
1               5                   10                  15

Gly Ala Leu Pro Gln Gln Tyr Pro Ala Ser Gly Glu Asn Lys Ser
                20                  25                  30

<210> SEQ ID NO 270
<211> LENGTH: 31
<212> TYPE: PRT
<213> ORGANISM: Homo sapiens

<400> SEQUENCE: 270

Pro Ser Ser Glu Val Ala Lys Pro Ser Glu Lys Asn Ser Asn Lys Ser
1               5                   10                  15

Ile Pro Ala Leu Gln Ser Ser Asp Ser Gly Asp Leu Gly Lys Trp
                20                  25                  30

<210> SEQ ID NO 271
<211> LENGTH: 31
<212> TYPE: PRT
<213> ORGANISM: Homo sapiens

<400> SEQUENCE: 271

Gln Asp Ala Leu Ser Lys Ser Leu Gln Asn Leu Pro Ser Arg Ser
1               5                   10                  15

Val Ser Lys Pro Ser Leu Phe Ser Ser Val Gln Leu Tyr Arg Gln
                20                  25                  30

<210> SEQ ID NO 272
<211> LENGTH: 31
<212> TYPE: PRT
<213> ORGANISM: Homo sapiens

<400> SEQUENCE: 272

Arg Pro Ser Gln Lys Lys Ser Arg Val Lys Ile Asn Trp Leu Lys Ser
1               5                   10                  15

Ala Thr Lys Gln Pro Ser Ile Leu Ser Lys Phe Cys Ser Leu Gly
                20                  25                  30

<210> SEQ ID NO 273
<211> LENGTH: 31
<212> TYPE: PRT
<213> ORGANISM: Homo sapiens

<400> SEQUENCE: 273

Ser Glu Asp Asp Ser Ala Val Pro Leu Ala Lys Ala Ala Pro Lys Ser
1               5                   10                  15

Gly Pro Ser Val Pro Val Ser Val Gln Thr Lys Asp Asp Val Tyr
                20                  25                  30

<210> SEQ ID NO 274
<211> LENGTH: 31

```
<212> TYPE: PRT
<213> ORGANISM: Homo sapiens

<400> SEQUENCE: 274

Asn Ser Phe Ser Lys Ser Thr Asn Ser Ser Asp Val Ser Ala Lys Ser
1               5                   10                  15
Gly Ala Val Thr Phe Ser Ser Gln Gly Arg Val Asn Pro Phe Lys
            20                  25                  30

<210> SEQ ID NO 275
<211> LENGTH: 29
<212> TYPE: PRT
<213> ORGANISM: Homo sapiens

<400> SEQUENCE: 275

Asn Arg Ala Ser Thr Ala Ala Ser Ser Ala Leu Gly Phe Ser Lys Ser
1               5                   10                  15
Ser Ser Pro Ser Ala Ser Leu Thr Glu Asn Glu Val Lys
            20                  25

<210> SEQ ID NO 276
<211> LENGTH: 31
<212> TYPE: PRT
<213> ORGANISM: Homo sapiens

<400> SEQUENCE: 276

Pro Pro Pro Val Lys Ile Ala Trp Lys Thr Ala Ala Arg Lys Ser
1               5                   10                  15
Leu Pro Ala Ser Ile Thr Met His Lys Gly Ser Leu Asp Leu Gln
            20                  25                  30

<210> SEQ ID NO 277
<211> LENGTH: 27
<212> TYPE: PRT
<213> ORGANISM: Homo sapiens

<400> SEQUENCE: 277

Met Asp Leu Gly Ser Pro Ser Leu Pro Lys Lys Ser Leu Pro Val Pro
1               5                   10                  15
Gly Ala Leu Glu Gln Val Ala Ser Arg Leu Ser
            20                  25

<210> SEQ ID NO 278
<211> LENGTH: 31
<212> TYPE: PRT
<213> ORGANISM: Homo sapiens

<400> SEQUENCE: 278

Glu Pro Val Leu Gly Asp Val Arg Glu Ser Thr Ala Phe Ser Arg Ser
1               5                   10                  15
Leu Leu Pro Val Lys Pro Val Glu Ile Glu Ile Glu Thr Pro Glu
            20                  25                  30

<210> SEQ ID NO 279
<211> LENGTH: 31
<212> TYPE: PRT
<213> ORGANISM: Homo sapiens

<400> SEQUENCE: 279

Ser Ala Leu Pro Tyr Ser Ser Phe Ser Ser Asp Gln Gly Leu Gly Glu
1               5                   10                  15
Ser Ser Ala Ala Pro Ser Gln Pro Ile Thr Ala Val Lys Asp Met
```

<210> SEQ ID NO 280
<211> LENGTH: 31
<212> TYPE: PRT
<213> ORGANISM: Homo sapiens

<400> SEQUENCE: 280

Ser Gly Tyr Gln Gly Gly Glu Gln Phe Gly Met Asp Phe Ser Arg Ser
1               5                   10                  15

Gly Leu Gly Leu His Ser Ser Phe Ser Arg Val Met Ile Gly Ser
            20                  25                  30

<210> SEQ ID NO 281
<211> LENGTH: 17
<212> TYPE: PRT
<213> ORGANISM: Homo sapiens

<400> SEQUENCE: 281

Met Ser Gly Gly Leu Ala Pro Ser Lys Ser Thr Val Tyr Val Ser Asn
1               5                   10                  15

Leu

<210> SEQ ID NO 282
<211> LENGTH: 31
<212> TYPE: PRT
<213> ORGANISM: Homo sapiens

<400> SEQUENCE: 282

Asn Cys Val Lys Arg Lys Ser Asp Ala Ala Lys Glu His Lys Lys Ser
1               5                   10                  15

Phe Asn His Ser Leu Ser Asp Thr Arg Lys Gly Lys Lys Gln Thr
            20                  25                  30

<210> SEQ ID NO 283
<211> LENGTH: 31
<212> TYPE: PRT
<213> ORGANISM: Homo sapiens

<400> SEQUENCE: 283

Thr His Ser Gly Glu Lys Asn Cys Lys Cys Asp Glu Cys Gly Lys Ser
1               5                   10                  15

Phe Asn Tyr Ser Ser Val Leu Asp Gln His Lys Arg Ile His Thr
            20                  25                  30

<210> SEQ ID NO 284
<211> LENGTH: 31
<212> TYPE: PRT
<213> ORGANISM: Homo sapiens

<400> SEQUENCE: 284

Ile His Pro Gly Lys Lys Ala His Glu Cys Lys Glu Cys Gly Lys Ser
1               5                   10                  15

Phe Ser Tyr Asn Ser Leu Leu Leu Gln His Arg Thr Ile His Thr
            20                  25                  30

<210> SEQ ID NO 285
<211> LENGTH: 31
<212> TYPE: PRT
<213> ORGANISM: Homo sapiens

<400> SEQUENCE: 285

-continued

His Arg Asp Gly Phe Pro Gln Pro Arg Arg Gly Arg Lys Lys Ser
1               5                  10                  15

Ile Val Ala Val Glu Pro Arg Ser Leu Ile Gln Gly Ala Phe Gln
                20                  25                  30

<210> SEQ ID NO 286
<211> LENGTH: 31
<212> TYPE: PRT
<213> ORGANISM: Homo sapiens

<400> SEQUENCE: 286

Asn Thr Ala Ala Glu Phe Gly Glu Pro Leu Pro Lys Arg Leu Lys Ser
1               5                  10                  15

Ser Val Val Ala Leu Asp Val Asp Gln Pro Gly Ala Asn Tyr Arg
                20                  25                  30

<210> SEQ ID NO 287
<211> LENGTH: 31
<212> TYPE: PRT
<213> ORGANISM: Homo sapiens

<400> SEQUENCE: 287

Ile His Thr Gly Lys Lys Ser His Lys Cys Ala Asp Cys Gly Lys Ser
1               5                  10                  15

Phe Phe Gln Ser Ser Asn Leu Ile Gln His Arg Arg Ile His Thr
                20                  25                  30

<210> SEQ ID NO 288
<211> LENGTH: 31
<212> TYPE: PRT
<213> ORGANISM: Homo sapiens

<400> SEQUENCE: 288

Ser Gln Gly Asn Thr Ser Ser Arg Arg Lys Thr Lys Ser Lys Ser
1               5                  10                  15

Ile Ala Ile Glu Asn Lys Glu Gln Lys Thr Gly Lys Thr Asn Glu
                20                  25                  30

<210> SEQ ID NO 289
<211> LENGTH: 31
<212> TYPE: PRT
<213> ORGANISM: Homo sapiens

<400> SEQUENCE: 289

Pro Tyr Ser Cys Pro Glu Cys Gly Lys Ser Phe Gly Val Arg Lys Ser
1               5                  10                  15

Leu Ile Ile His His Arg Ser His Thr Lys Glu Arg Pro Tyr Glu
                20                  25                  30

<210> SEQ ID NO 290
<211> LENGTH: 31
<212> TYPE: PRT
<213> ORGANISM: Homo sapiens

<400> SEQUENCE: 290

Thr Asp His Lys His Asp Val Tyr Trp Lys Ser Phe Asn Gln Lys Ser
1               5                  10                  15

Val Leu Ile Thr Glu Asp Arg Val Pro Lys Gly Ser Tyr Ala Phe
                20                  25                  30

<210> SEQ ID NO 291
<211> LENGTH: 31

<212> TYPE: PRT
<213> ORGANISM: Homo sapiens

<400> SEQUENCE: 291

```
Leu Leu Asn Ser Asn Lys Ser Gly Ala Ala Phe Asn Gln Ser Lys Ser
1               5                   10                  15
Leu Thr Leu Pro Gln Thr Cys Asn Arg Glu Lys Ile Tyr Thr Cys
            20                  25                  30
```

<210> SEQ ID NO 292
<211> LENGTH: 31
<212> TYPE: PRT
<213> ORGANISM: Homo sapiens

<400> SEQUENCE: 292

```
Tyr His Ala Gly Glu Arg Pro His Arg Cys Ala Asp Cys Gly Lys Ser
1               5                   10                  15
Phe Val Tyr Gly Ser His Leu Ala Arg His Arg Arg Thr His Thr
            20                  25                  30
```

<210> SEQ ID NO 293
<211> LENGTH: 31
<212> TYPE: PRT
<213> ORGANISM: Homo sapiens

<400> SEQUENCE: 293

```
Ser Cys Glu Ile Asn Asn Ser Thr Lys Phe Ser Gly Asp Gly Lys Ser
1               5                   10                  15
Phe Leu His Gly Asn Tyr Glu Glu Leu Tyr Ser Ala Ala Lys Phe
            20                  25                  30
```

<210> SEQ ID NO 294
<211> LENGTH: 31
<212> TYPE: PRT
<213> ORGANISM: Homo sapiens

<400> SEQUENCE: 294

```
Ile His Thr Gly Glu Lys Pro Cys Glu Cys Lys Gln Cys Gly Lys Ser
1               5                   10                  15
Phe Ser Tyr Ser Ala Thr His Arg Ile His Lys Arg Thr His Thr
            20                  25                  30
```

<210> SEQ ID NO 295
<211> LENGTH: 31
<212> TYPE: PRT
<213> ORGANISM: Homo sapiens

<400> SEQUENCE: 295

```
Arg Gln Gln Gln Glu Gly Thr Asn Leu Pro Asp Val Pro Asn Lys Ser
1               5                   10                  15
Ala Pro Ser Pro Thr Ser Asn Ser Thr Tyr Leu Thr Met Asn Ala
            20                  25                  30
```

<210> SEQ ID NO 296
<211> LENGTH: 31
<212> TYPE: PRT
<213> ORGANISM: Homo sapiens

<400> SEQUENCE: 296

```
Val Thr Lys Ala Met Pro Val Thr Lys Pro Ile Thr Val Thr Lys Ser
1               5                   10                  15
Val Pro Val Thr Lys Pro Val Pro Val Thr Lys Pro Ile Thr Val
```

<210> SEQ ID NO 297
<211> LENGTH: 31
<212> TYPE: PRT
<213> ORGANISM: Homo sapiens

<400> SEQUENCE: 297

Val His Thr Gly Lys Lys Ser Glu Lys Thr Lys Asn Cys Gly Lys Ser
1               5                   10                  15

Phe Thr Asn Phe Ser Gln Leu Ser Ala His Ala Lys Thr His Lys
            20                  25                  30

<210> SEQ ID NO 298
<211> LENGTH: 31
<212> TYPE: PRT
<213> ORGANISM: Homo sapiens

<400> SEQUENCE: 298

Lys Ile Cys Ile Pro Asn Glu Tyr Arg Lys Gly Ser Thr Val Lys Ser
1               5                   10                  15

Ser Leu Ile Thr His Gln Gln Thr His Thr Glu Glu Lys Ser Tyr
            20                  25                  30

<210> SEQ ID NO 299
<211> LENGTH: 31
<212> TYPE: PRT
<213> ORGANISM: Homo sapiens

<400> SEQUENCE: 299

Ser Ser Gly Leu Lys Asn Ser Ala Glu Phe Asn Arg Asp Gly Lys Ser
1               5                   10                  15

Leu Phe His Ala Asn His Lys Gln Phe Tyr Thr Glu Met Lys Phe
            20                  25                  30

<210> SEQ ID NO 300
<211> LENGTH: 31
<212> TYPE: PRT
<213> ORGANISM: Homo sapiens

<400> SEQUENCE: 300

Tyr Lys Thr Asp Trp His Arg Tyr Asn Leu Arg Arg Lys Val Ala Ser
1               5                   10                  15

Met Ala Pro Val Thr Ala Glu Gly Phe Gln Glu Arg Val Arg Ala
            20                  25                  30

<210> SEQ ID NO 301
<211> LENGTH: 31
<212> TYPE: PRT
<213> ORGANISM: Homo sapiens

<400> SEQUENCE: 301

Lys Lys Thr Phe Met Lys Asp Ser Val Val Gly Ser Ser Lys Lys Ser
1               5                   10                  15

Ala Thr Tyr Ile Cys Lys Met Cys Pro Phe Thr Thr Ser Ala Lys
            20                  25                  30

<210> SEQ ID NO 302
<211> LENGTH: 31
<212> TYPE: PRT
<213> ORGANISM: Homo sapiens

<400> SEQUENCE: 302

-continued

Val His Thr Arg Glu Lys Pro Tyr Lys Cys Glu Asp Arg Gly Arg Ser
1               5                   10                  15

Phe Gly Trp Ser Thr Asn Leu Asn Glu Tyr Lys Lys Ile His Thr
            20                  25                  30

<210> SEQ ID NO 303
<211> LENGTH: 31
<212> TYPE: PRT
<213> ORGANISM: Homo sapiens

<400> SEQUENCE: 303

Lys Pro Asn Arg Cys His Glu Cys Gly Lys Thr Val Arg Asp Lys Ser
1               5                   10                  15

Gly Leu Ala Glu His Trp Arg Ile Arg Thr Gly Glu Lys Pro Tyr
            20                  25                  30

<210> SEQ ID NO 304
<211> LENGTH: 31
<212> TYPE: PRT
<213> ORGANISM: Homo sapiens

<400> SEQUENCE: 304

Arg Pro Phe Ser Cys Gly Ile Cys Gly Lys Ser Phe Ser Gln Arg Ser
1               5                   10                  15

Ala Leu Ile Pro His Ala Arg Ser His Ala Arg Glu Lys Pro Phe
            20                  25                  30

<210> SEQ ID NO 305
<211> LENGTH: 31
<212> TYPE: PRT
<213> ORGANISM: Homo sapiens

<400> SEQUENCE: 305

Arg His Thr Gly Lys Lys Pro Phe Lys Cys Lys Asn Arg Gly Lys Ser
1               5                   10                  15

Phe Cys Met Leu Ser Gln Leu Thr Gln His Lys Lys Ile His Thr
            20                  25                  30

<210> SEQ ID NO 306
<211> LENGTH: 20
<212> TYPE: PRT
<213> ORGANISM: Homo sapiens

<400> SEQUENCE: 306

Met Met Ala Lys Ser Ala Leu Arg Glu Asn Gly Thr Asn Ser Glu Thr
1               5                   10                  15

Phe Arg Gln Arg
            20

<210> SEQ ID NO 307
<211> LENGTH: 31
<212> TYPE: PRT
<213> ORGANISM: Homo sapiens

<400> SEQUENCE: 307

Gln Glu Gln Met Asn Pro Lys Glu Lys Leu Lys Pro Phe Gln Arg Ser
1               5                   10                  15

Gly Leu Pro Phe Pro Lys Ser Gly Val Val Ser Arg Leu Glu Gln
            20                  25                  30

<210> SEQ ID NO 308

```
<211> LENGTH: 31
<212> TYPE: PRT
<213> ORGANISM: Homo sapiens

<400> SEQUENCE: 308

Asn Gly Leu Asp Glu Ser Phe Cys Gly Arg Thr Leu Arg Asn Arg Ser
1               5                   10                  15

Ile Ala His Pro Glu Glu Ile Ser Ser Asn Ser Gln Val Arg Ser
                20                  25                  30

<210> SEQ ID NO 309
<211> LENGTH: 31
<212> TYPE: PRT
<213> ORGANISM: Homo sapiens

<400> SEQUENCE: 309

Pro Gln Glu Ser Thr Pro Ala Pro Pro Lys Lys Asp Ile Lys Gly Ser
1               5                   10                  15

Tyr Val Ser Ile His Ser Ser Gly Phe Arg Asp Phe Leu Leu Lys
                20                  25                  30

<210> SEQ ID NO 310
<211> LENGTH: 7
<212> TYPE: PRT
<213> ORGANISM: Artificial Sequence
<220> FEATURE:
<223> OTHER INFORMATION: Exemplary Motif Sequence

<400> SEQUENCE: 310

Lys Ala Ala Ser Ala Ala Ala
1               5

<210> SEQ ID NO 311
<211> LENGTH: 7
<212> TYPE: PRT
<213> ORGANISM: Artificial Sequence
<220> FEATURE:
<223> OTHER INFORMATION: Exemplary Motif Sequence

<400> SEQUENCE: 311

Ala Ala Ala Ser Ala Arg Ala
1               5
```

SITE-SPECIFIC SERINE ADP-RIBOSYLATED PROTEINS AND PEPTIDES AND METHOD FOR PRODUCING THE SAME

This application contains a Sequence Listing that has been submitted electronically in ASCII format and is hereby incorporated by reference in its entirety. The ASCII copy, created on Nov. 18, 2024, is named "009848-0560487-CORRECTED Sequence listing.txt" and is 211,995 bytes in size.

The present invention relates to a method for producing a site-specifically serine ADP-ribosylated protein or peptide, comprising: (a) subjecting a protein or peptide comprising or consisting of an amino acid sequence comprising two or more serines, wherein at least one serine is phosphorylated and at least one serine is non-phosphorylated, to a serine ADP-ribosylation reaction. The present invention also relates to a site-specifically serine ADP-ribosylated protein or peptide produced by the method of the invention.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention is in the technical field of a chemically complex protein post-translational modification (PTM) called ADP-ribosylation (ADPr). The biological and clinical importance of this modification is well established: ADPr and the enzymes responsible therefore (known as poly (ADP-ribose) polymerase (PARPs)) have been found to play a role in many key cellular processes, including maintenance of genomic stability, cell differentiation and proliferation, cytoplasmic stress responses, and microbial virulence. Moreover, dysregulation of ADPr has been linked to diseases including cancer, diabetes, neurodegenerative disorders, and heart failure, leading to the development of therapeutic PARP inhibitors, many of which are currently in clinical trials. In particular, the PARP-1 inhibitors Olaparib (brand name Lynparza), Rucaparib (brand name Rubraca) and Niraparib (brand name Zejula) are EU- and FDA-approved therapeutic agents for cancer therapy.

Despite the clear biological and clinical importance of ADPr, further progress in the field is limited by the difficulties in elucidating the underlying molecular mechanisms. This is due to a lack of essential tools and reagents, ranging from the modified proteins and peptides themselves up to site-specific antibodies, tools which are commercially available for other biologically important protein modifications.

Recently it has been reported that ADP-ribosyl can be attached to serine, a previously unknown and unexpected amino acid target residue for this PTM (Leidecker et al., 2016, Nat Chem Biol 12, 998-1000). Shortly afterwards it was shown that this new form of ADPr, which is called serine-ADP-ribosylation (Ser-ADPr), is a widespread PTM that targets hundreds of different substrates, including PARP-1 itself (Bonfiglio et al., 2017, Mol Cell 65, 932-940 e936). The required elements for the in vitro modification of a target substrate with ADP-ribose on serine are PARP-1 or -2 (including variants, such as PARP-1 E988Q), Histone PARylation factor 1 (HPF1), NAD$^+$, activated (i.e. sonicated) DNA and the substrate itself, all of them contained in a reactor (e.g. a tube) in which an uncontrolled ADP-ribosylation of both the substrate and the modifying enzyme occurs (Bonfiglio et al., 2017, Mol Cell 65, 932-940 e936). The inventors have also recently filed the EP application 18 15 4508.8 which describes an ADP-ribosylation method resulting in essentially pure serine ADP-ribosylated forms of proteins or peptides in a cost-effective manner on a scale varying from small (a few µg) to large (several milligrams).

Hence, at present peptides and proteins with one or more serines that can be enzymatically ADP-ribosylated can be produced. However when peptides and proteins comprise two or more serines, this either creates peptides and proteins, wherein all serines that can be enzymatically ADP-ribosylated are in fact ADP-ribosylated or—in case the conditions are selected, so that not essentially pure serine ADP-ribosylated forms are obtained—it creates a mixture of different partially ADP-ribosylated species.

However, in these cases where a protein or peptide comprises two or more serines, it is currently not possible to generate a protein or peptide wherein one or more selected serines are enzymatically site-specifically ADP-ribosylated. This is because no enzymatic method is available for site-specifically adding an ADP-ribosyl group to a selected serine within a protein or peptide. Site-specific serine ADP-ribosylated proteins or peptides are important, for example, because they allow for the generation of antibodies which are specific for the ADP-ribosylation of a serine within a given protein or peptide. Since serine is the major residue for ADP-ribosylation upon DNA damage (Palazzo et al. (2018), eLife; 7: e34334) such antibodies have the potential of becoming a sensitive and specific marker of DNA single-strand break repair. A standard approach to prevent ADPr of selected serines is converting these serines into alanines (FIG. 3). However, the final ADP-ribosylated product is not identical to naturally-occurring amino acid sequences with two or more serines, which is a drawback for downstream applications such as the generation of antibodies. This drawback is overcome by the present invention.

The technical problem underlying the present invention is therefore the provision of a method which allows the production of a protein or peptide that comprises two or more serines, wherein one or more selected serines are site-specifically ADP-ribosylated.

The solution to this technical problem is achieved by providing the embodiments characterized in the claims.

The present invention thus relates in a first aspect to a method for producing a site-specifically serine ADP-ribosylated protein or peptide, comprising: (a) subjecting a protein or peptide comprising or consisting of an amino acid sequence comprising two or more serines, wherein at least one serine is phosphorylated and at least one serine is non-phosphorylated, to a serine ADP-ribosylation reaction.

With respect to step (a) is to be understood that in this step the at least one non-phosphorylated serine becomes ADP-ribosylated whereas the at least one phosphorylated serine is protected from serine ADP-ribosylation. Thus, this step results in a site-specifically serine ADP-ribosylated protein or peptide. It is therefore preferred that the at least one serine being non-phosphorylated and thus to be site-specifically serine ADP-ribosylated has a free side chain (—CH$_2$—OH) carrying no chemical modification. It is more preferred that also the amino acids, in particular the side chains of the amino acids neighbouring the at least one serine being non-phosphorylated and thus to be site-specifically serine ADP-ribosylated carry no chemical modification, such as a post-translational modification. The neighbouring amino acids designate with increased preference one, two, three and four amino acids on each side of said at least one serine.

A site-specifically serine ADP-ribosylated protein or peptide shall designate a protein or peptide having an amino acid sequence comprising two or more serines, wherein at least one serine is ADP-ribosylated and at least one serine is not ADP-ribosylated.

The term "two or more serines" means, for example, 2, 3, 4 or 5. Similarly, the term "at least one" means, for example, 2, 3, 4 or 5.

The term "comprising" preferably means "consisting of".

The method of the invention generally does not result in the production of a single site-specifically serine ADP-ribosylated protein or peptide but in a plurality of site-specifically serine ADP-ribosylated proteins or peptides that are all characterized by the same site-specific serine ADP-ribosylation pattern. The term "plurality" will be further defined herein below.

The terms "protein" (wherein "protein" is interchangeably used with "polypeptide") and "peptide" as used herein describe a group of molecules consisting of amino acids. Whereas peptides consist of up to 30 amino acids, "proteins" consist of more than 30 amino acids. Peptides and proteins may further form dimers, trimers and higher oligomers, i.e. consisting of more than one molecule which may be identical or non-identical. The corresponding higher order structures are, consequently, termed homo- or heterodimers, homo- or heterotrimers etc. Peptides and proteins are preferably composed of the 20 naturally-occurring amino acids being encoded by the genetic code optionally plus selenocysteine. However, the peptides and proteins may also comprise one or more non-natural amino acids, noting that about 500 amino acids are known in the art. Any non-natural amino acid is preferably an α-amino acids (generic formula $H_2NCHRCOOH$, where R is an organic substituent known as a "side chain" of the amino acid).

Serine (2-Amino-3-hydroxypropanoic acid) is an α-amino acid that is used in the biosynthesis of proteins. The side chain of serine comprises a hydroxymethyl group, and serine is therefore a polar amino acid.

The term "phosphorylation" as used herein refers to the attachment of a phosphoryl group ($-PO_3^{2-}$) (also designated phosphate group herein) to a molecule. Protein and peptide phosphorylation is considered the most abundant post-translational modification in eukaryotes (Vlastaridis et al. (2017), GigaScience, 6:1-11). Phosphorylation can occur on serine, threonine and tyrosine side chains through phosphoester bond formation, on histidine, lysine and arginine through phosphoramidate bonds, and on aspartic acid and glutamic acid through mixed anhydride linkages. In accordance with the method of the first aspect of the invention phosphorylation occurs at least on one serine. Phosphorylation is reversible. Kinases phosphorylate proteins and peptides whereas phosphatases dephosphorylate proteins and peptides. Since phosphorylated serine is commercially available, proteins and peptides with two or more serines can also be synthesized with at least one phosphorylated serine.

Adenosine diphosphate (ADP; also known as adenosine pyrophosphate (APP)) is an important organic compound in cellular metabolism and is inter alia essential for the flow of energy in living cells. ADP consists of three structural components: a sugar backbone attached to a molecule of adenine and two phosphate groups bonded to the 5'-carbon atom of ribose. ADP-ribose is a related molecular species in which a second ribose is bound via its 5'-carbon to the second phosphate of ADP.

ADP-ribosylation (ADPr) is the addition of one or more ADP-ribose moieties to one or more amino acids of a protein or peptide. Originally, acidic amino acids (glutamate and aspartate) were described as the main sites of ADP-ribosylation. However, many other ADP-ribose acceptor sites such as serine, arginine, cysteine, lysine, diphthamide, phosphoserine, and asparagine have been identified in subsequent works. In accordance with the present invention the one or more amino acids to which one or more ADP-ribose moieties are added is/are serine(s). Said, ADP-ribosylation of serine is referred to herein as serine-ADP-ribosylation (Ser-ADPr). ADPr may be mono-ADP-ribosylation or poly-ADP-ribosylation. Serine-mono-ADP ribosylation is the addition of only one ADP-ribose to a serine side chain. Serine-poly-ADP ribosylation is the addition of two or more ADP-riboses to the side chain of a serine (O-linkage). The method of the present invention may employ wild-type poly-(ADP-ribose) polymerases (PARPs) that catalyse the transfer of a single or multiple ADP-ribose molecules to target proteins. Hence, the use of wild-type PARPs results in a combination of Ser-mono-ADPr and Ser-poly-ADPr. Means for obtaining exclusively Ser-mono-ADP-ribosylated proteins and peptides will be discussed herein below.

A serine ADP-ribosylation reaction therefore refers to a chemical reaction occurring in a reaction mixture which comprises the protein or peptide to be ADP-ribosylated and the elements required for the in vitro modification of serines by ADP-ribose. Suitable reaction mixtures and the required elements are known from the prior art referred to herein above. Further details will be provided herein below.

In accordance with the present invention the amino acid sequence of the protein or peptide to be modified comprises at least two serines, so that by the method of the present invention a site-specifically ADP-ribosylated protein or peptide is obtained. A serine can be at the C-terminus and/or the N-terminus of the protein or peptide. Preferably the serines are surrounded by other amino acids.

As is demonstrated in the examples herein below it has surprisingly been found by the inventors that the post-translational modification of serine by a phosphoryl group and an ADP-ribose are mutually exclusive. If a serine is phosphorylated it cannot be ADP-ribosylated and vice versa. For this reason a phosphoryl group on a serine serves as a protection group against the addition of an ADP-ribose in an ADP-ribosylation reaction. The phosphoryl group at the serine is stable throughout the ADP-ribosylation reaction and cannot be removed. This in turn allows the site-specific addition of ADP-ribose to selected serines within the amino acid sequence of a protein or peptide in an ADP-ribosylation reaction, wherein the one or more serines that shall not become ADP-ribosylated carry a phosphoryl group. For example, in the case of an amino acid sequence with three serines two serines may carry a phosphoryl group, so that only one selected serine becomes ADP-ribosylated, or only one serine may carry a phosphoryl group, so that two selected serines become ADP-ribosylated. The use of the phosphoryl group as a protection group for serines offers several advantages. Phosphorylated serine is commercially available, so that proteins and peptides can be synthesized by standard procedures and then directly subjected to the ADP-ribosylation reaction. Moreover, the phosphoryl group can be easily removed from the serines after the ADP-ribosylation reaction by dephosphorylation. Dephosphorylation is the removal of a phosphate group from an organic compound by hydrolysis. By dephosphorylation proteins and peptides may be obtained having an amino acid sequence identical to the respective natural-occurring proteins or peptides, expect that one or more selected serines thereof are serine ADP-ribosylated.

It can be expected that what is demonstrated herein below in the examples for the phosphoryl group on serines as protection group against ADP-ribosylation is transferable to other post-translational modifications, as well.

Hence, the present invention relates in a broader context also to a method for producing a site-specifically serine ADP-ribosylated protein or peptide, comprising: (a) subjecting a protein or peptide comprising or consisting of an amino acid sequence comprising two or more serines, wherein at least one serine contains a post-translational modification (PTM) different to ADPr and at least one serine does not contain any PTM, to a serine ADP-ribosylation reaction.

With respect to this step (a) is to be understood that the at least one serine not containing a PTM becomes ADP-ribosylated whereas the at least one serine with the PTM is protected from serine ADP-ribosylation. Thus, this step results in a site-specifically serine ADP-ribosylated protein or peptide. It is therefore preferred that the at least one serine without a PTM and thus to be site-specifically serine ADP-ribosylated has a free side chain (—CH$_2$—OH) carrying no chemical modification. It is more preferred that also the amino acids, in particular the side chains of the amino acids neighbouring the at least one serine without a PTM and thus to be site-specifically serine ADP-ribosylated carry no chemical modification, such as a PTM. The neighbouring amino acids designate with increased preference one, two, three and four amino acids on each side of said at least one serine.

The at least one serine containing a PTM preferably contains an O-linked PTM; i.e. a PTM which is covalently linked to the oxygen of the hydroxyl group within the side chain of serine. Also ADP-ribose and the phosphoryl group are linked to said oxygen, so that also other PTMs than a phosphoryl group being linked linked to said oxygen might serve as protection group against ADP-ribosylation in a serine ADP-ribosylation reaction.

Non-limiting and preferred examples of such O-linked PTMs are O-linked glycosylation and O-acylation.

The O-linked glycosylation is preferably selected from O—N-acetylgalactosamine, O-fucose, O-glucose, O—N-acetylglucosamine, and O-mannose.

O-linked glycosylation occurs in the Golgi apparatus in eukaryotes, and also in archaea and bacteria. The enzymes (glycosyltransferases) which mediate O-linked glycosylation in the Golgi apparatus are known and may be employed to generate a peptide comprising or consisting of an amino acid sequence comprising two or more serines which is to be site-specifically serine ADP-ribosylated, wherein at least one serine contains an O-linked glycosylation as PTM. However, it is preferred to synthesize the protein or peptide to be site-specifically serine ADP-ribosylated. Means and methods for the synthesis of a protein or peptide will be discussed in more detail herein below. During the synthesis one or more serines which contain a PTM can be used, so that a protein or peptide comprising or consisting of an amino acid sequence comprising two or more serines is obtained, wherein at least one serine contains a post-translational modification (PTM) different to ADPr and at least one serine does not contain any PTM. For instance, methods for the site-specific incorporation of glycosylated serine into proteins and peptides as well as for the generation of glycosylated serine-analogs are available (see, for example, Fahmi et al. (2007). Am. Chem. Soc., 129 (12): 3586-3597 and Quast et al. (2015), FEBS Letters, 589 (15): 1703-1712).

Moreover, O-linked glycosylation is reversible, so that it is possible to remove O-linked glycosylation after the ADP-ribosylation reaction. Also the enzymes (e.g. β-N-acetylglucosaminidase) involved in the removal of O-linked glycosylation are known to the skilled person. Commercial kits for the removal of O-linked glycosylation are also available, for example, from prozyme. Hence, in case the PTM is O-linked glycosylation the above-method may further comprise as step (b) (after step (a)) removing the O-linked glycosylation from the at least one O-glycosylated serine.

In the following preferred embodiments of the first aspect of the invention and further aspects of the invention will be described. These preferred embodiments and the further aspects apply to the above broader method, as well. For instance, also step (a) of the braoder method may comprises the synthesis of the protein or peptide to be site-specifically serine ADP-ribosylated, wherein the synthesis preferably comprises a solid-phase peptide synthesis. The ADP-ribosylation reaction may be carried out as described herein below for the first aspect of the invention. Likewise the site-specifically serine ADP-ribosylated protein or peptide produced by the broader method may be purified as described herein below in connection with the first aspect of the invention. The broader method may additional comprise the formulation of site-specifically serine ADP-ribosylated protein or peptide as a composition (e.g. a pharmaceutical, diagnostic or cosmetic composition), as well. The site-specifically serine ADP-ribosylated protein or peptide produced by the broader method may comprise further PTMs as detailed herein below in connection with the first aspect of the invention.

Moreover, the invention as described herein also relates to a site-specifically serine ADP-ribosylated protein or peptide produced by the above broader method; a binding molecule (preferably an antibody) specifically binding to the a site-specifically serine ADP-ribosylated protein or peptide produced by the above broader method; and a composition (e.g. a pharmaceutical, diagnostic or cosmetic composition) comprising a site-specifically serine ADP-ribosylated protein or peptide produced by the above broader method.

The broader method may also be implemented into the method of the sixth aspect of the invention, wherein the above-described post-translational modification (PTM) different to ADPr may also be used instead of the phosphoryl group in order to protect a serine form ADP-ribosylation in a serine ADP-ribosylation reaction.

Turning now back to the first aspect of the invention, it is in accordance with a preferred embodiment of the first aspect of the invention that the method further comprises (b) removing the phosphate group(s) from the at least one phosphorylated serine.

As mentioned, by dephosphorylation proteins and peptides may be obtained having an amino acid sequence identical to the respective natural-occurring proteins or peptides, except that one or more selected serines thereof are serine ADP-ribosylated.

In the context of the claimed method, step (b) follows step (a).

In accordance with a more preferred embodiment of the first aspect of the invention the phosphate group(s) is/are removed by an enzyme, preferably a phosphatase, more preferably an enzyme selected from the group consisting of protein serine/threonine phosphatases, and most preferably selected from the group consisting of the lambda protein phosphatase and alkaline phosphatase, wherein the alkaline phosphatase is preferably selected from calf intestinal phosphatase (CIP), antarctic phosphatase (AnP), and shrimp alkaline phosphatase (SAP).

As discussed above, phosphate groups are removed from serines by a hydrolysis reaction. Hydrolysis is generally the cleavage of biomolecules where a water molecule is consumed to effect the separation of a larger molecule into component parts. The hydrolysis reaction is often catalyzed by enzymes, so called hydrolases.

A phosphatase is an enzyme that uses water to cleave a phosphoric acid monoester into a phosphate ion and an alcohol. Because a phosphatase enzyme catalyzes the hydrolysis of its substrate, it is a subcategory of hydrolases. The phosphatase is a protein phosphatase and able to remove a phosphate group from the phosphorylated amino acid residue of its substrate protein.

Serine/threonine phosphatases are protein phosphatases that can dephosphorylate serines and threonines. This is because serines and threonines have similar side-chain compositions that contain a hydroxyl group and thus may be dephosphorylated by the same enzymes.

The lambda protein phosphatase is a $Mn^{2+}$-dependent protein phosphatase with activity towards phosphorylated serine, threonine and tyrosine residues. It can be used to release phosphate groups from phosphorylated serine, threonine and tyrosine residues in proteins and peptides.

Antarctic phosphatase (AnP) is a heat labile alkaline phosphatase purified from a recombinant source. AnP inter alia hydrolyses ribo-, as well as deoxyribonucleoside triphosphates (NTPs and dNTPs).

Akaline phosphatase (ALP) is found across a multitude of organisms, including prokaryotes and eukaryotes, with the same general function but in different structural forms suitable to the environment they function. The akaline phosphatase inter alia hydrolyses ribo-, as well as deoxyribonucleoside triphosphates (NTPs and dNTPs).

Shrimp alkaline phosphatase (SAP) is a heat labile alkaline phosphatase that ca be purified from its natural source or also a recombinant source (rSAP). Rapid and irreversible heat inactivation eliminates unwanted activity.

The akaline phosphatase is preferably calf intestinal phosphatase (CIP), antarctic phosphatase (AnP), and shrimp alkaline phosphatase (SAP).

It is also possible to combine enzymes, for example, CIP and antarctic phosphatase. Antarctic phosphatase has a very high specific activity comparable to CIP, but CIP cannot be completely heat inactivated. Antarctic phosphatase is heat inactivated in minutes, but requires added zinc as co-factor. Hence, the exact properties of the enzymes may be used to adjust the dephosphorylation reaction.

In accordance with a further preferred embodiment of the first aspect of the invention step (a) comprises the synthesis of the protein or peptide as defined in the method of the invention, wherein the synthesis preferably comprises a solid-phase peptide synthesis.

As mentioned, phosphorylated serine is commercially available, so that phosphorylated proteins and peptides to be site-specifically serine ADP-ribosylated can be synthesized by standard procedures and then directly subjected to the ADP-ribosylation reaction. Accordingly, this synthesis may form part of the method of the invention, e.g., as step (a) (i) prior to the ADP-ribosylation, which is then step (a) (ii).

The synthesis of proteins and peptides including proteins and peptides, wherein one or more selected serines are phosphorylated are art-established methods. In these methods multiple amino acids are linked via amide bonds, also known as peptide bonds, in order to generate the amino acid sequence forming the desired protein or peptide. The synthesis generally comprises the condensation reaction of the carboxyl group of one amino acid to the amino group of another. Protecting group strategies are usually necessary to prevent undesirable side reactions with the various amino acid side chains.

The chemical synthesis of peptides can be carried out using classical solution-phase techniques, although these have been replaced in most research and development settings by solid-phase methods. The currently most used method for the production of synthetic proteins and peptides in the lab is solid-phase peptide synthesis. The basic concept in solid phase peptide synthesis is the step-wise construction of a peptide chain attached to an insoluble polymeric support. This approach permits unreacted reagents to be removed by washing without loss of product. Synthesis of the peptide chain proceeds from the carboxyl end to the amino terminus of the peptide. The carboxyl moiety of each incoming amino acid is activated by one of several strategies and couples with the α-amino group of the preceding amino acid. The α-amino group of the incoming residue is temporarily blocked in order to prevent peptide bond formation at this site. The residue is de-blocked at the beginning of the next synthesis cycle. In addition, reactive side chains on the amino acids are modified with appropriate protecting groups. The peptide chain is extended by reiteration of the synthesis cycle. Excess reagents are used to drive reactions as close to completion as possible. This generates the maximum possible yield of the final product. After fully assembling the peptide the side-chain protecting groups are removed, and the peptide is cleaved from the solid support, using conditions that inflict minimal damage on labile residues.

Also longer peptide chains and proteins may be generated by chemical ligating smaller peptides. Moreover, split inteins, spontaneous isopeptide bond formation and sortase ligation may be used to generate longer peptide chains and proteins (Banerjee and Howarth (2018), Current Opinion in Biotechnology, 51 (16-23)).

In accordance with another preferred embodiment of the first aspect of the invention the ADP-ribosylation reaction is carried out in an ADP-ribosylation reaction mixture, said mixture comprising (i) a buffered solution, (ii) NAD+, (iii) PARP-1, PARP-2 or the PARP-1 variant E988Q, (iv) HPF1, (v) sonicated DNA, said sonicated DNA preferably comprising DNA fragments of 10 to 330 bp, and (vi) the protein or peptide as defined in the method of the invention.

As discussed above, the required reaction mixture and elements for the in vitro modification of serines by ADP-ribose are known from the prior art (Bonfiglio et al., 2017, Mol Cell 65, 932-940 e936). Accordingly, for producing serine ADP-ribosylated proteins or peptides a buffered solution, $NAD^+$, one of PARP-1, PARP-2 and PARP-1 E988Q, HPF1, sonicated DNA, and the substrate proteins or peptides to be serine ADP-ribosylated are required.

The buffered solution comprises preferably 5 to 60 mM, more preferably 10 to 60 mM of a buffer. The nature of the buffer will be further defined herein below. Moreover, the buffered solution preferably has a pH between 5.0 and 9.0, more preferably between 5.5 to 8.5, and most preferably between 6.1 to 8.3. Preferably 0.2 to 2.5 mM $NAD^+$, at least 50 nM (more preferably 50 to 3000 nM) PARP-1, PARP-2 or the PARP-1 variant E988Q, at least 100 nM (more preferably 100 to 5000 nM) HPF1, at least 10 μg/mL (more preferably 10 μg/mL to 200 μg/mL) sonicated DNA, said sonicated DNA preferably comprising DNA fragments of 10 to 330 bp, and up to 600 M protein or peptide are comprised in the reaction mixture. Using such a buffered solution and the reactants in the indicated concentrations results in the very efficient ADP-ribosylation of serines in proteins or peptides, unless protected by phosphorylation.

Nicotinamide adenine dinucleotide (NAD) is a coenzyme found in all living cells. The compound is a dinucleotide consisting of an adenine base and nicotinamide. NAD exists in two forms, an oxidized and reduced form abbreviated as $NAD^+$ and NADH respectively. The $NAD^+$ used in the method of the invention can be radioactive $NAD^+$. The use of radioactive $NAD^+$ results in the radioactive labelling of serine ADP-ribosylated peptides and proteins. Herein, the concentration of 0.2 to 2.5 mM $NAD^+$ is preferably a concentration of 1.5 to 2.5 mM $NAD^+$ and more preferably a concentration of 1.8 to 2.2 mM $NAD^+$.

Poly (ADP-ribose) polymerase (PARP) is a family of proteins involved in a number of cellular processes, such as DNA repair, genomic stability, and programmed cell death. Currently the PARP family comprises 17 members (10 putative). The method of the invention employs PARP-1, PARP-2 or the PARP-1 variant E988Q. PARP-1 (also known as $NAD^+$ ADP-ribosyltransferase 1 or poly [ADP-ribose] synthase 1) is an enzyme that in humans is encoded by the PARP-1 gene and PARP-2, an enzyme that in humans is encoded by the PARP-2 gene. PARP-1 and PARP-2 contain a catalytic domain and are capable of catalyzing a poly (ADP-ribosyl)ation reaction. PARP-2 has a catalytic domain being homologous to that of PARP-1, but PARP-2 lacks the N-terminal DNA binding domain of PARP-1 which activates the C-terminal catalytic domain of PARP-1. For the action of PARP-1 and PARP-2, $NAD^+$ is required as substrate for generating ADP-ribose monomers, as is sonicated DNA, said DNA mimicking DNA with breaks. The PARP-1 E988Q mutant is incapable of poly (ADP-ribosyl)ation activity but instead mono (ADP-ribosyl)ates (Sharifti et al., EMBO J. 2013 May 2; 32 (9): 1225-1237). Since the PARP enzyme is the most sensitive compound of the method it is preferably added last to the aqueous buffered solution.

The amino acid sequence of human PARP-1 is shown in SEQ ID NO: 1, of human PARP-1 E988Q in SEQ ID NO: 2, of mouse PARP-1, isoforms 1 and 2 in SEQ ID NOs 3 and 4 and of rat PARP-1 in SEQ ID NO: 5. The sequence identity of human PARP-1 with mouse and rat PARP-1 is 92%. Accordingly, PARP-1 is preferably a sequence being at least 90% identical to SEQ ID NO: 1. PARP-1 is more preferably a sequence being with increasing preference at least 95%, at least 98% or at least 99% identical to any one of SEQ ID NOs 1 to 5.

The amino acid sequences of human PARP-2, isoforms 1 and 2 are shown in SEQ ID NOs 6 and 7, and of mouse PARP-2 in SEQ ID NO: 8. The sequence identity of human PARP-2 with mouse PARP-2 is 84%. Accordingly, PARP-2 is preferably a sequence being at least 80%, preferably at least 84% identical to SEQ ID NO: 6 or 7. PARP-2 is more preferably a sequence being with increasing preference at least 95%, at least 98% or at least 99% identical to any one of SEQ ID NOs 6 to 8.

In accordance with the present invention, the term "percent (%) sequence identity" describes the number of matches ("hits") of identical amino acids of two or more aligned amino acid sequences as compared to the number of amino acid residues making up the overall length of the template amino acid sequences. In other terms, using an alignment, for two or more sequences or subsequences the percentage of amino acid residues that are the same (e.g. 80%, 85%, 90% or 95% identity) may be determined, when the (sub) sequences are compared and aligned for maximum correspondence over a window of comparison, or over a designated region as measured using a sequence comparison algorithm as known in the art, or when manually aligned and visually inspected. The sequences which are compared to determine sequence identity may thus differ by substitution(s), addition(s) or deletion(s) of amino acids.

The skilled person is also aware of suitable programs to align amino acid sequences. The percentage sequence identity of amino acid sequences can, for example, be determined with programmes such as CLUSTLAW, FASTA and BLAST. Preferably the BLAST programme is used, namely the NCBI BLAST algorithm (Stephen F. Altschul, Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402).

PARP-1 and -2 are activated by DNA breaks and cleave $NAD^+$ thereby generating nicotinamide and ADP-ribose. In higher eukaryotes, PARP-1 and -2 translate the occurrence of DNA breaks detected by its zinc-finger domain into a signal (poly ADP-ribose) which is synthesized and amplified by its DNA-damage dependent catalytic domain. Hence, the ADP-ribosylation activity of PARP-1 and -2 requires the presence of DNA breaks. DNA breaks are present in sonicated DNA. Sonicated DNA is DNA that has been fragmented by sonication. Sonication is the act of applying brief periods of ultrasound energy to DNA, so that the DNA is sheared into smaller fragments, preferably fragments of 10 to 330 bp.

Histone PARylation factor 1 (HPF1) acts as a cofactor for serine ADP-ribosylation by conferring serine specificity on PARP-1 and PARP-2. Quantitative proteomics revealed that histone serine ADPr does not occur in cells lacking HPF1. Moreover, adding HPF1 to in vitro PARP-1/PARP-2 reactions is necessary and sufficient for serine-specific ADPr of histones and PARP-1 itself (Bonfiglio et al., 2017, Mol Cell 65, 932-940 e936).

The amino acid sequence of human HPF1 is shown in SEQ ID NO: 9 and of mouse HPF1 in SEQ ID NO: 10. The sequence identity of human HPF1 with mouse HPF1 is 89%. Accordingly, HPF1 is preferably a sequence being at least 85%, preferably at least 89% identical to SEQ ID NO: 9. HPF1 is more preferably a sequence being with increasing preference at least 95%, at least 98% or at least 99% identical to SEQ ID NO: 9 or 10.

The up to 600 μM protein or peptide, said protein or peptide comprising at least two serines, is preferably between 60 and 600 μM protein or peptide, said protein or peptide comprising at least two serines, and is more preferably between 100 and 600 μM protein or peptide, said protein or peptide comprising at least two serines.

In accordance with a more preferred embodiment of the first aspect of the invention, the reaction mixture further comprises at least 1 μM, preferably 1 to 10 M PARG and/or the ADP-ribosylated protein or peptide is incubated with at least 1 μM, preferably 1 to 10 UM PARG.

In accordance with this preferred embodiment a site-specifically serine mono-ADP-ribosylated protein or peptide is obtained.

Poly(ADP-ribose) glycohydrolase (PARG) is an enzyme which generates free ADP-ribose from the poly-ADP-ribose chain but cannot cleave the ADP-ribose-protein bond, therefore leading to a serine mono-ADP-ribosylated protein or peptide. Hence, the simultaneous addition of PARG to the reaction mixture provides a means for reducing Ser-poly-ADPr into single Ser-mono-ADPr. The amino acid sequences of human PARG, isoforms 1, 2 and 3 are shown in SEQ ID NOs 11, 12 and 13, of mouse PARG, isoforms 1 and 2 in SEQ ID NOs 14 and 15 and of rat PARG in SEQ ID NO: 16. The sequence identity of human PARG with mouse and rat PARG is 87% and 85%, respectively. Accordingly, PARG is preferably a sequence being at least 85% identical to one or more of SEQ ID NOs 11, 12 and 13. PARG is more preferably a sequence being with increasing preference at least 95%, at least 98% or at least 99% identical to any one of SEQ ID NOs 11 to 16.

An alternative strategy the PARP-1 mutant E988Q could be employed by using, which only mono-ADP-ribosylates and, therefore, produces Ser-mono-ADPr. Hence, in case PARG is present it is preferred to use PARP-1 or PARP-2 instead of the PARP-1 mutant E988Q.

In accordance with another more preferred embodiment of the first aspect of the invention, the ADP-ribosylation reaction is carried out at 15-35° C. and preferably at room temperature.

The ADP-ribosylation reaction is very robust and works at temperatures that might be found in a laboratory, i.e. 15-35° C. Room temperature preferably refers to a temperature range of 18-27° C. and more preferably 20-25° C.

In accordance with a further more preferred embodiment of the first aspect of the invention, the ADP-ribosylation reaction is carried out for at least 90 min, preferably at least 120 min, more preferably at least 240 min, and most preferably at least 320 min.

Carrying out the reaction for at least 90 min ensures the effective ADP-ribosylation of the unprotected target serine/s of the protein or peptide. In particular for longer proteins/peptides carrying many serines that are to be ADP-ribosylation it may be advantageous to prolong the reaction time to at least 120 min or at least 240 min or at least 320 min.

In accordance with a more preferred embodiment of the first aspect of the invention, a fresh pool of 0.2 to 2.5 mM $NAD^+$ is added to the reaction mixture at least every 90 minutes, preferably at least every 60 minutes and more preferably at least every 45 minutes.

Also here the concentration of 0.2 to 2.5 mM $NAD^+$ is preferably a concentration of 1.5 to 2.5 mM $NAD^+$ and more preferably a concentration of 1.8 to 2.2 mM $NAD^+$. Also described herein is a concentration of 1 to 2 mM $NAD^+$. Connected with the reaction time, the addition of a fresh pool of $NAD^+$ was tested during the optimization of the conditions of the Ser-ADP-ribosylation of proteins or peptides. It was found that it is preferred to add fresh $NAD^+$ to the solution constituting the reaction mixture at least every 90 minutes in order to effectively ADP-ribosylate the target serine/s of the protein or peptide. In particular for longer substrates, it may be advantageous to add fresh $NAD^+$ to the reaction mixture at least every 60 minutes or 45 minutes.

After the reaction has been carried out it can be stopped by the addition of a PARP inhibitor. The PARP inhibitor is preferably Olaparib, and Olaparib is preferably used at a concentration of about 2 µm. In this connection the term "about" is preferably ±20% and more preferably ±10%. Another example of a PARP inhibitor is Rucaparib.

In accordance with another more preferred embodiment of the first aspect of the invention, the at least two serines are each neighboured by at least one basic amino acid.

The at least one basic amino acid is with increasing preference at least two, at least three and at least four basic amino acids. The basic amino acids are preferably Lys and/or Arg. The term "neighboured" means that at least one basic amino acid can be found up to three amino acids adjacent to the serine to be ADP-ribosylated, either N-terminally or C-terminally (i.e. at amino acid positions -3 to +3). Non-limiting examples of such a motif are "KAASAAA" (SEQ ID NO. 310) and "AAASARA" (SEQ ID NO. 311). The at least one basic amino acid is preferably up to two amino acids adjacent to the serine to be ADP-ribosylated (i.e. at amino acid positions -2 to +2) and more preferably directly adjacent to the serine (i.e. at amino acid positions -1 and/or +1). The motif "KS" (i.e. Lysine at the -1 amino acid position) is most preferred since it can be frequently found in nature. Among all these options it is preferred that the serine is neighboured on both sides by at least one basic amino acid Related to the above more preferred embodiment of the first aspect of the invention, it is preferred that the protein or peptide to be ADP-ribosylated has an isoelectric point of at least 8.0.

The isoelectric point is the pH at which a particular molecule carries no net electrical charge in the statistical mean. Among the naturally-occurring amino acids the basic amino acids Lys and Arg have the highest isoelectric point. The isoelectric point of Lys is 9.74 and the isoelectric point of Arg is 10.76. Hence, a protein or peptide having an isoelectric point of at least 8.0 is a protein or peptide that carries no net electrical charge at a basic pH of 8.0 or higher.

Within the proteins or peptides the serines being neighboured by at least one basic amino acid are particularly well recognized by the Ser-ADP-ribosylation machinery. Also particularly well recognized by the Ser-ADP-ribosylation machinery are proteins and peptides having an overall basic isoelectric point of at least 8.0. The same holds true for the following preferred embodiment.

In accordance with a yet further preferred embodiment of the first aspect of the invention, the peptide or protein to be site-specifically ADP-ribosylated contains a positively charged tail, preferably a poly-arginine and/or poly-lysine tail.

The term "positively charged tail" refers to a C- or N-terminal tail of the peptide or protein to be site-specifically Ser-ADPr, which comprises or consists of at least 3 basic amino acids, preferably Lys and/or Arg residues. The positively charged tail preferably comprises or consists of at least 4 basic amino acids, preferably Lys and/or Arg residues. The addition of a positively charged tail may further boost the reaction efficiently.

In accordance with a yet further more preferred embodiment, the reaction mixture further comprises (e) 10 to 80 mM NaCl or KCl, and/or (f) 0.5 to 2 mM $MgCl_2$.

The activity of enzymes may be affected by the addition of inorganic salts, e.g., during in vitro assays. The concentration of salts, the identity of the ions, and the ionic strength of the solution can affect the activity of an enzyme. The enzymatic activity of PARP does not require the presence of inorganic salts, so that peptides and proteins can be highly efficiently Ser-ADP-ribosylated even in the absence of salts in the aqueous buffered solution. However, it is also possible to use PARP in connection with inorganic salts. A non-limiting example of inorganic salt conditions is the use of 10 to 80 mM NaCl or KCl, and/or 0.5 to 2 mM $MgCl_2$ in the aqueous buffered solution.

In accordance with a more preferred embodiment, the buffer is a Tris-HCl buffer and is preferably used at a final concentration of 40-60 mM, a Hepes buffer and is preferably used at a final concentration of 40-60 mM, more preferably about 50 mM, or a phosphate buffer and is preferably used at a final concentration of 5-20 mM, more preferably about 10 mM.

Tris has a pKa of 8.07 at 25° C., which means that Tris-HCl buffer has an effective pH range between 7.5 and 9.0. The useful buffer range for Tris-HCl (7.5 to 9) coincides with the physiological pH typical of most living organisms.

This and its low cost make Tris-HCl one of the most common buffers in the biology/biochemistry laboratory. In this respect it is noted that the pH of a solution is defined as the negative logarithm to the base 10 of the hydrogen ion concentration in g ions $L^{-1}$ (pH=−log 10 [$H^+$]). Thus pH can also be defined as the logarithm to the base 10 of the reciprocal of $H^+$ ion concentration. During the ionization of weak acid HA, where the ionization is not complete, the dissociation constant is the ratio of the dissociated and undissociated components (Ka=[$H^+$]×[$A^-$]/[HA]). Hence, pKa is defined as the negative logarithm to the base 10 of the Ka in g ions $L^{-1}$ or as logarithm to the base 10 of the reciprocal of Ka. The relationship between pH and pKa is given by Henderson-Hasselbach equation (pH=pKa+log [$A^-$]/[HA]).

Hepes (4-(2-hydroxyethyl)-1-piperazineethanesulfonic acid) is a zwitterionic organic chemical buffering agent. Hepes has a $pK_{a1}$ (25 C)=3 and a $pK_{a2}$ (25 C)=7.5 and accordingly has buffering capacity at pH ranges between 2.5 to 3.5 and 6.8 to 8.2. The latter pH range coincides with the physiological pH typical of most living organisms.

Phosphates have a very high buffering capacity and are highly soluble in water. Gomori buffers, the most commonly used phosphate buffers, consist of a mixture of monobasic dihydrogen phosphate and dibasic monohydrogen phosphate. By varying the amount of each salt, a range of buffers can be prepared that buffer well between pH 5.8 and 8.0.

In accordance with another preferred embodiment, the reaction mixture is an aqueous buffered solution, wherein the solvent of the aqueous buffered solution is preferably water.

An aqueous buffered solution is a solution in which one of the solvents is water. In this respect it is preferred that water is the only solvent so that the aqueous solution is water.

In accordance with a preferred embodiment of the first aspect of the invention, the method further comprises purifying the site-specifically serine ADP-ribosylated protein or peptide.

Once the method of the present invention has been carried out, the reaction mixture comprises the site-specifically serine ADP-ribosylated proteins or peptides and in addition the ingredients needed for the ADP-ribosylation reaction. In accordance with the above preferred embodiment the site-specifically Ser-ADP-ribosylated proteins or peptides are separated from these ingredients and thereby purified. Means and methods for purifying the site-specifically serine ADP-ribosylated proteins or peptides from the reaction mixture are known in the art and preferred examples will be further detailed herein below.

In accordance with a preferred embodiment of the first aspect of the invention, the site-specifically serine ADP-ribosylated protein or peptide is purified by StageTip fractionation employing C8, C18, SCX, SAX or SDB-RPS chromatography media, cation or anion exchange chromatography, hydrophilic interaction chromatography, phosphopeptide enrichment, enrichment with an ADP-ribose-binding protein domain, boronate affinity chromatography, filtering the reaction with an ultrafiltration device, a spin column or a combination thereof.

Stage tips can be used to rapidly purify proteins and peptides from a reaction mix. C8, C18, SAX and SCX stage tips are commercially available. C8, C18, SAX, SCX and SDB-RPS are chromatography materials that are loaded into pipet tips. C8 and C18 are silica-based materials. SCX and SAX refer to strong cation exchange and strong anion exchange resins and membranes, respectively. SDB-RPS is a styrenedivinylbenzene resin that has been modified with sulfonic acid groups to make it hydrophilic. Because SDB-RPS displays both reversed phase and cation exchange interactions, both affinities can be considered to design selective extractions.

Cation and anion exchange chromatography are forms of ion exchange chromatography, which can be used to separate molecules based on their net surface charge. Cation exchange chromatography uses a negatively charged ion exchange resin with an affinity for molecules having net positive surface charges. Anion-exchange chromatography is a process that separates substances based on their charges using an ion-exchange resin containing positively charged groups, such as diethyl-aminoethyl groups (DEAE). Cation and anion exchange chromatography are used both for preparative and analytical purposes and can separate a large range of molecules, including serine ADP-ribosylated proteins or peptides. Depending on the overall charge of the proteins or peptides cation and anion exchange chromatography is used.

Hydrophilic interaction chromatography (or hydrophilic interaction liquid chromatography, HILIC) is a variant of normal-phase liquid chromatography that partly overlaps with other chromatographic applications such as ion chromatography and reversed phase liquid chromatography. HILIC uses hydrophilic stationary phases with reversed-phase type eluents.

Phosphopeptide enrichment enables efficient enrichment of phosphorylated peptides and proteins from complex and fractionated protein digests. Since the ADP-ribosylated protein or peptide contains phosphate groups, phosphopeptide enrichment can be used for its purification. For example, $TiO_2$ and Fe-NTA phosphopeptide enrichment kits are commercially available.

ADP-ribose-binding domains are domains of proteins that bind to ADP-ribose moieties (Vivelo and Leung (2015), Proteomics. 2015 January; 15 (0): 203-217). Thus, these domains can be used to purify ADP-ribosylated proteins or peptides. Several protein domains that bind mono- and poly (ADP)-ribose are known, such as the WWE domain, the PBZ (PAR-binding zinc finger) domain, the PBM (PAR-binding motif), the Af1521 macrodomain, and the catalytically inactive E756D mutant of PARG (PARG-DEAD approach).

Boronate affinity chromatography is a unique means for selective separation and enrichment of cis-diol-containing compounds. Cis-diol-containing biomolecules are an important class of compounds, including glycoproteins, glycopeptides, ribonucleosides, ribonucleotides, saccharides, and catecholamines.

Ultrafiltration devices are commercially available for the concentration of biological samples. They can be used, for example, in either a swing bucket or fixed angle rotors which accept 2.0 mL centrifuge tubes at maximum speed 10,000× g. During centrifugation the serine ADP-ribosylated peptides flow through the filter whereas other ingredients of the reaction mixture, such as PARP and HPF are retained on the filter.

Spin columns, such as the G25 spin columns are microspin columns that were initially designed for the rapid purification of DNA for use in a wide range of applications, including desalting, buffer exchange, and removal of unincorporated nucleotides from end-labelled oligonucleotides. When used in connection with serine ADP-ribosylated proteins or peptides as comprised in the reaction mixture other ingredients of the reaction mixture, such as $NAD^+$, can be removed.

In accordance with a further preferred embodiment of the first aspect of the invention, the method further comprises formulating the produced site-specifically serine ADP-ribosylated protein or peptide into a composition, preferably a pharmaceutical, diagnostic or cosmetic composition.

A composition comprises the produced site-specifically serine ADP-ribosylated proteins or peptides formulated together with at least one further compound. Accordingly, "formulating" means bringing together, preferably mixing the produced site-specifically serine ADP-ribosylated proteins or peptides and at least one further compound.

In accordance with the present invention, the term "pharmaceutical composition" relates to a composition for administration to a patient, preferably a human patient. As mentioned, the pharmaceutical composition of the invention comprises the produced site-specifically serine ADP-ribosylated proteins or peptides. It may, optionally, comprise further molecules capable of altering the characteristics of said proteins or peptides thereby, for example, stabilizing, modulating and/or activating their function. The composition may be in solid, liquid or gaseous form and may be, inter alia, in the form of (a) powder(s), (a) tablet(s), (a) solution(s) or (an) aerosol(s). The pharmaceutical composition of the present invention may, optionally and additionally, comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician.

The diagnostic composition of the invention is useful in the detection of an undesired physiological condition or a disease. Accordingly, the diagnostic composition of the invention may be used for assessing the onset or the disease status and in particular a disease state.

The diagnostic composition of the invention can be administered as sole active agent or can be administered in combination with other agents, if the diagnostic composition is, for example, used to identify sites of undesired physiological condition or a disease.

A cosmetic composition according to the invention is for use in non-therapeutic applications. Cosmetic compositions may also be defined by their intended use, as compositions intended to be rubbed, poured, sprinkled, or sprayed on, or otherwise applied to the human body for cleansing, beautifying, promoting attractiveness, or altering the appearance. The particular formulation of the cosmetic composition according to the invention is not limited. Envisaged formulations include rinse solutions, emulsions, creams, milks, gels such as hydrogels, ointments, suspensions, dispersions, powders, solid sticks, foams, sprays and shampoos. For this purpose, the cosmetic composition according to the invention may further comprise cosmetically acceptable diluents and/or carriers. Choosing appropriate carriers and diluents in dependency of the desired formulation is within the skills of the skilled person. Suitable cosmetically acceptable diluents and carriers are well known in the art and include agents referred to in WO 2006/053613. Preferred formulations for said cosmetic composition are rinse solutions and creams.

In accordance with another preferred embodiment of the first aspect of the invention, the protein or peptide further comprises at least one post-translational modification other than serine ADP-ribosylation and serine phosphorylation.

A post-translational modification (PTM) refers to a naturally-occurring covalent and generally enzymatic modification of proteins following protein biosynthesis. Post-translational modifications can occur on the amino acid side chains or at the protein's C- or N-termini of a protein or peptide. They can extend the chemical repertoire of the 20 naturally-ocurring amino acids by modifying an existing functional group or introducing a new one, such as phosphate. A post-translational modification may be introduced into the protein or peptide as defined in the method of the invention by the use of an enzyme but also synthetically during protein synthesis as describe herein above for phosphorylated serine.

The at least one post-translational modification may be added to the protein or peptide as defined in the method of the invention before or after the serine ADP-ribosylation reaction. In case the at least one post-translational modification is added before it can be added, for example, during the synthesis of the protein or peptide as described herein above in connection with the addition of the at least one phosphorylated serine.

The post-translational modification is not particularly limited, unless it may reduce or even prevent the serine ADP-ribosylation of the at least one serine which is to be serine ADP-ribosylated in the method of the invention. For this reason it is preferred that said at least one serine to be serine ADP-ribosylated does not comprise any additional post-translational modification. As mentioned above, it is in particular preferred that the at least one serine to be serine ADP-ribosylated has a free side chain (—$CH_2$—OH) carrying no chemical modification.

In accordance with a more preferred embodiment of the first aspect of the invention, the post-translational modification is selected from lipidation, N- or O-linked glycosylation, phosphorylation of an amino acid other than serine, acetylation, amidation, hydroxylation, mono- or di- or tri-methylation, ubiquitylation, SUMOylation, neddylation, butyrylation, propionylation, crotonylation, 2-hydroxyisobutyrylation, malonylation, succinylation, citrullination and pyrrolidone carboxylic acid and sulfation.

Within the above list of post-translational modification a selection from the subgroup consisting of N- or O-linked glycosylation, phosphorylation of an amino acid other than serine, acetylation, mono- or di- or tri-methylation, ubiquitylation, SUMOylation, neddylation, butyrylation, propionylation, crotonylation, 2-hydroxyisobutyrylation, malonylation, succinylation, and citrullination (R) is preferred.

These post-translational modifications are the most frequent post-translational modifications as were reported in the prior art (see selene.princeton.edu/PTMCuration/).

In accordance with a preferred embodiment of the first aspect of the invention, the method is carried out ex vivo or in vitro.

Ex vivo and in vitro are carried out outside the human oir animal body and do not comprise methods for treatment of the human or animal body by surgery or therapy and diagnostic methods practised on the human or animal body.

The present invention relates in a second aspect to a site-specifically serine ADP-ribosylated protein or peptide produced by the method of the first aspect of the invention.

As discussed herein above, the method of the first aspect of the invention allows for the first time to control which serine(s) in a protein and peptide with two or more serines become(s) ADP-ribosylated and which not by enzymatic means.

For this reason the method of the first aspect of the invention allows for the first time to enzymatically generate site-specifically serine ADP-ribosylated proteins or peptides. Hence, the present invention is directed in a second aspect to these site-specifically serine ADP-ribosylated protein or peptide.

The site-specifically serine ADP-ribosylated protein or peptide is preferably not present as a single, isolated site-specifically serine ADP-ribosylated protein or peptide but is a plurality of site-specifically serine ADP-ribosylated proteins or peptides, wherein each copy of the protein or peptide within the plurality has the site-specific serine ADP-ribosylation pattern as generated by the method of the first aspect of the invention. In this respect the term plurality means with increasing preference at least 10 copies, at least 100 copies, at least 1000 copies, at least 10000 copies, and at least 100000 copies of the discussed protein or peptide.

The present invention relates in a third aspect to a site-specifically serine ADP-ribosylated protein or peptide comprising or consisting of (i) the amino acid sequence of any one of SEQ ID NOs 17 to 309, wherein within the amino acid sequence at least one serine is ADP-ribosylated and at least one serine is not ADP-ribosylated, and wherein the at least one serine not being ADP-ribosylated is optionally phosphorylated, or (ii) an amino acid sequence being at least 80%, preferably at least 85%, more preferably at least 90% and most preferably at least 95% identical to the amino acid sequence of (i), provided that at least two, preferably all the serines within the amino acid sequence of (i) are conserved.

Also described herein is a site-specifically serine ADP-ribosylated protein or peptide comprising or consisting of an amino acid sequence which differs by the amino acid sequence of (i) by up to three, preferably up two and most preferably by one amino acid substitution, deletion or insertion, provided that at least two, preferably all the serines within the amino acid sequence of (i) are conserved. In this context a substitution is preferred over a deletion or insertion. The substitution is preferably a conservative substitution, noting that a conservative substitution is an amino acid replacement that changes a given amino acid to a different amino acid with similar biochemical properties (e.g. charge, hydrophobicity and size).

For example, with respect to a protein or peptide comprising or consisting of the amino acid sequence of SEQ ID NO: 17, the serine in amino acid position 6 of SEQ ID NO: 17 is ADP-ribosylated whereas the serine in amino acid in position 14 of SEQ ID NO: 17 is not ADP-ribosylated or vice versa, and the serine not being ADP-ribosylated can optionally be phosphorylated. The production of a peptide consisting of SEQ ID NO: 17, wherein the serine in amino acid position 6 of SEQ ID NO: 17 is ADP-ribosylated whereas the serine in amino acid position 14 of SEQ ID NO: 1 is not ADP-ribosylated due to the protection by a phosphate group is illustrated herein below in Example 1.

SEQ ID NOs 17 to 309 are all amino acid sequences being a part of a naturally-occurring protein. All amino acid sequences comprise at least two serines.

For example, SEQ ID NO: 17 is a fragment of the enzyme PARP-1, i.e. amino acids positions 494 to 514 of the human PARP-1 amino acid sequence. Ser499 of PARP-1 is the main endogenous ADPr site upon DNA damage. Hence, a protein or peptide of SEQ ID NO: 17 with a serine ADPr in amino acid position 6 and no serine ADPr in amino acid position 14 may be used to generate antibodies or other binding molecules specifically recognizing this protein or peptide carrying this modification. Such an antibody or other binding molecule may then be used to detect DNA damage. SEQ ID NOs 18 (amino acid position 505-523), 19 (amino acid position 103-125) and 20 (amino acid positions 200-234) are different fragments of the enzyme PARP-1.

SEQ ID NOs 21 to 25 are all amino acid sequences of 25 amino acids derived from histone 3 variants. The histone 3 peptides are highly conserved and amino acid differences can only be found in positions 18 (A or V), 23 (A or T) and 25 (A or S). Hence, SEQ ID NOs 21 to 25 share among each other a sequence identity of above 80%. SEQ ID NOs 26 and 27 are amino acidc sequences being derived from histone 2B and histone 4, respectively. SEQ ID NOs 28 to 30 are peptides of 21 amino acids and are derived from histone 2A variants. The three histone 2A peptides are fully conserved. The production of a site-specific ADP-ribosylated form of a H2B peptide corresponding to the human amino acid sequence (1-32) is illustrated in Example 1. The production of a site-specific ADP-ribosylated form of a H2A peptide corresponding to the human amino acid sequence (1-19) is illustrated in Example 2. Within SEQ ID NOs 28 to 30 it is preferred that the serine at amino acid at position 1 is ADP-ribosylated while the amino acids at positions 18 and 19 are not ADP-ribosylated. SEQ ID NOs 31 to 35 are derived from histone H1 variants but share no significant sequence similarity. Histone ADP-ribosylation plays a role in DNA repair, replication and transcription; see for review Messner and Hottiger (2011), Trends in Cell Biology, 21 (9): 534-542. Moreover, Histones are a substrate of the enzyme PARP-1.

The proteins and peptides comprising or consisting of SEQ ID NOs 36 to 309 are all endogenous targets of serine ADP-ribosylation upon DNA damage in vivo.

The at least one serine not being ADP-ribosylated is optionally phosphorylated since in the method of the invention the at least one serine not to be ADP-ribosylated is protected from ADPr by a phosphate group. As also detailed herein above, after ADPr has been added to the desired target serine(s), the phosphate group may be removed.

The proviso that the serines within the amino acid sequence of (i) are conserved means that the serines may not be replaced by another amino acid or deleted from the amino acid sequence. The proviso preferably also requires that no additional serines are added to the amino acid sequence.

The present invention relates in a fourth aspect to a binding molecule, preferably an antibody, specifically binding to the site-specifically serine ADP-ribosylated protein or peptide of the second or third aspect of the invention.

A binding molecule of the fourth aspect is a compound being capable of specifically binding to the site-specifically serine ADP-ribosylated protein or peptide of the second or third aspect of the invention. Specific binding designates that the binding molecule does not or essentially does not bind to other proteins or peptides than the site-specifically serine ADP-ribosylated protein or peptide of the second or third aspect of the invention.

In particular, it is preferred that the binding molecule is not capable to bind the same protein or peptide with a different serine ADP-ribosylion pattern and also with no serine ADP-ribosylation. A binding molecule of the fourth aspect is, for example, suitable for research purposes. For example, an antibody binding to the protein of the fourth aspect can be used in immuonassays, such as an ELISA or Western Blot. Immunoassays are biochemical tests that can measure the presence or concentration of the protein of the fourth aspect in a sample (e.g. a solution). The binding molecule of the fourth aspect is preferably capable of inhibiting the protein or peptide of the second or third aspect. In this case the binding molecule is designated inhibitor.

Preferably, the binding molecule is an antibody.

The term "antibody" as used in accordance with the present invention comprises, for example, polyclonal or monoclonal antibodies. Furthermore, also derivatives or fragments thereof, which still retain the binding specificity to the target, e.g. the site-specifically ADP-ribosylated protein or peptide, are comprised in the term "antibody". Antibody fragments or derivatives comprise, inter alia, Fab or Fab' fragments, Fd, F(ab')2, Fv or scFv fragments, single domain VH or V-like domains, such as VhH or V-NAR-domains, as well as multimeric formats such as minibodies, diabodies, tribodies or triplebodies, tetrabodies or chemically conjugated Fab'-multimers (see, for example, Harlow and Lane "Antibodies, A Laboratory Manual", Cold Spring Harbor Laboratory Press, 198; Harlow and Lane "Using Antibodies: A Laboratory Manual" Cold Spring Harbor Laboratory Press, 1999; Altshuler E P, Serebryanaya D V, Katrukha A G. 2010, Biochemistry (Mosc)., vol. 75 (13), 1584; Holliger P, Hudson P J. 2005, Nat Biotechnol., vol. 23 (9), 1126). The multimeric formats in particular comprise bispecific antibodies that can simultaneously bind to two different types of antigen. The first antigen can be found on the protein of the invention. The second antigen may, for example, be a tumor marker that is specifically expressed on cancer cells or a certain type of cancer cells. Non-limting examples of bispecific antibodies formats are Biclonics (bispecific, full length human lgG antibodies), DART (Dual-affinity Re-targeting Antibody) and BiTE (consisting of two single-chain variable fragments (scFvs) of different antibodies) molecules (Kontermann and Brinkmann (2015), Drug Discovery Today, 20 (7): 838-847).

The term "antibody" also includes embodiments such as chimeric (human constant domain, non-human variable domain), single chain and humanised (human antibody with the exception of non-human CDRs) antibodies.

Various techniques for the production of antibodies are well known in the art and described, e.g. in Harlow and Lane (1988) and (1999) and Altshuler et al., 2010, loc. cit. Thus, polyclonal antibodies can be obtained from the blood of an animal following immunisation with an antigen in mixture with additives and adjuvants and monoclonal antibodies can be produced by any technique which provides antibodies produced by continuous cell line cultures. Examples for such techniques are described, e.g. in Harlow E and Lane D, Cold Spring Harbor Laboratory Press, 1988; Harlow E and Lane D, Using Antibodies: A Laboratory Manual, Cold Spring Harbor Laboratory Press, 1999 and include the hybridoma technique originally described by Köhler and Milstein, 1975, the trioma technique, the human B-cell hybridoma technique (see e.g. Kozbor D, 1983, Immunology Today, vol. 4, 7; Li J, et al. 2006, PNAS, vol. 103 (10), 3557) and the EBV-hybridoma technique to produce human monoclonal antibodies (Cole et al., 1985, Alan R. Liss, Inc, 77-96). Furthermore, recombinant antibodies may be obtained from monoclonal antibodies or can be prepared de novo using various display methods such as phage, ribosomal, mRNA, or cell display. A suitable system for the expression of the recombinant (humanised) antibodies may be selected from, for example, bacteria, yeast, insects, mammalian cell lines or transgenic animals or plants (see, e.g., U.S. Pat. No. 6,080,560; Holliger P, Hudson P J. 2005, Nat Biotechnol., vol. 23 (9), 11265). Further, techniques described for the production of single chain antibodies (see, inter alia, U.S. Pat. No. 4,946,778) can be adapted to produce single chain antibodies specific for an epitope of the site-specifically ADP-ribosylated protein or peptide. Surface plasmon resonance as employed in the BIAcore system can be used to increase the efficiency of phage antibodies.

The binding molecule may also be a small molecule, an antibody mimetic or an aptamer.

The "small molecule" as used herein is preferably an organic molecule. Organic molecules relate or belong to the class of chemical compounds having a carbon basis, the carbon atoms linked together by carbon-carbon bonds. The original definition of the term organic related to the source of chemical compounds, with organic compounds being those carbon-containing compounds obtained from plant or animal or microbial sources, whereas inorganic compounds were obtained from mineral sources. Organic compounds can be natural or synthetic. The organic molecule is preferably an aromatic molecule and more preferably a heteroaromatic molecule. In organic chemistry, the term aromaticity is used to describe a cyclic (ring-shaped), planar (flat) molecule with a ring of resonance bonds that exhibits more stability than other geometric or connective arrangements with the same set of atoms. Aromatic molecules are very stable, and do not break apart easily to react with other substances. In a heteroaromatic molecule at least one of the atoms in the aromatic ring is an atom other than carbon, e.g. N, S, or O. For all above-described organic molecules the molecular weight is preferably in the range of 200 Da to 1500 Da and more preferably in the range of 300 Da to 1000 Da.

Alternatively, the "small molecule" in accordance with the present invention may be an inorganic compound. Inorganic compounds are derived from mineral sources and include all compounds without carbon atoms (except carbon dioxide, carbon monoxide and carbonates). Preferably, the small molecule has a molecular weight of less than about 2000 Da, or less than about 1000 Da such as less than about 500 Da, and even more preferably less than about Da amu. The size of a small molecule can be determined by methods well-known in the art, e.g., mass spectrometry. The small molecules may be designed, for example, based on the crystal structure of the target molecule, where sites presumably responsible for the biological activity can be identified and verified in in vivo assays such as in vivo high-throughput screening (HTS) assays.

As used herein, the term "antibody mimetics" refers to compounds which, like antibodies, can specifically bind antigens, such the site-specifically serine ADP-ribosylated protein or peptide in the present case, but which are not structurally related to antibodies. Antibody mimetics are usually artificial peptides or proteins with a molar mass of about 3 to 20 kDa. For example, an antibody mimetic may be selected from the group consisting of affibodies, adnectins, anticalins, DARPins, avimers, nanofitins, affilins, Kunitz domain peptides and Fynomers®.

These polypeptides are well known in the art and are described in further detail herein below.

The term "affibody", as used herein, refers to a family of antibody mimetics which is derived from the Z-domain of staphylococcal protein A. Structurally, affibody molecules are based on a three-helix bundle domain which can also be incorporated into fusion proteins. In itself, an affibody has a molecular mass of around 6 kDa and is stable at high temperatures and under acidic or alkaline conditions. Target specificity is obtained by randomisation of 13 amino acids located in two alpha-helices involved in the binding activity of the parent protein domain (Feldwisch J, Tolmachev V.; (2012) Methods Mol Biol. 899:103-26).

The term "adnectin" (also referred to as "monobody"), as used herein, relates to a molecule based on the 10th extracellular domain of human fibronectin III (10Fn3), which adopts an Ig-like β-sandwich fold of 94 residues with 2 to 3 exposed loops, but lacks the central disulphide bridge (Gebauer and Skerra (2009) Curr Opinion in Chemical Biology 13:245-255). Adnectins with the desired target specificity, i.e. against the site-specifically ADP-ribosylated protein or peptide, can be genetically engineered by introducing modifications in specific loops of the protein.

The term "anticalin", as used herein, refers to an engineered protein derived from a lipocalin (Beste G, Schmidt F S, Stibora T, Skerra A. (1999) Proc Natl Acad Sci USA. 96 (5): 1898-903; Gebauer and Skerra (2009) Curr Opinion in Chemical Biology 13:245-255). Anticalins possess an eight-stranded ß-barrel which forms a highly conserved core unit among the lipocalins and naturally forms binding sites for ligands by means of four structurally variable loops at the open end. Anticalins, although not homologous to the IgG superfamily, show features that so far have been considered typical for the binding sites of antibodies: (i) high structural plasticity as a consequence of sequence variation and (ii) elevated conformational flexibility, allowing induced fit to targets with differing shape.

As used herein, the term "DARPin" refers to a designed ankyrin repeat domain (166 residues), which provides a rigid interface arising from typically three repeated β-turns. DARPins usually carry three repeats corresponding to an artificial consensus sequence, wherein six positions per repeat are randomised. Consequently, DARPins lack structural flexibility (Gebauer and Skerra, 2009).

The term "avimer", as used herein, refers to a class of antibody mimetics which consist of two or more peptide sequences of 30 to 35 amino acids each, which are derived from A-domains of various membrane receptors and which are connected by linker peptides. Binding of target molecules occurs via the A-domain and domains with the desired binding specificity, i.e. for the site-specifically ADP-ribosylated protein or peptide, can be selected, for example, by phage display techniques. The binding specificity of the different A-domains contained in an avimer may, but does not have to be identical (Weidle U H, et al., (2013), Cancer Genomics Proteomics; 10 (4): 155-68).

A "nanofitin" (also known as affitin) is an antibody mimetic protein that is derived from the DNA binding protein Sac7d of *Sulfolobus acidocaldarius*. Nanofitins usually have a molecular weight of around 7 kDa and are designed to specifically bind a target molecule, such as e.g. the site-specifically ADP-ribosylated protein or peptide, by randomising the amino acids on the binding surface (Mouratou B, Béhar G, Paillard-Laurance L, Colinet S, Pecorari F., (2012) Methods Mol Biol.; 805:315-31).

The term "affilin", as used herein, refers to antibody mimetics that are developed by using either gamma-B crystalline or ubiquitin as a scaffold and modifying amino-acids on the surface of these proteins by random mutagenesis. Selection of affilins with the desired target specificity, i.e. against the site-specifically ADP-ribosylated protein or peptide, is effected, for example, by phage display or ribosome display techniques. Depending on the scaffold, affilins have a molecular weight of approximately 10 or 20 kDa. As used herein, the term affilin also refers to di- or multimerised forms of affilins (Weidle U H, et al., (2013), Cancer Genomics Proteomics; 10 (4): 155-68).

A "Kunitz domain peptide" is derived from the Kunitz domain of a Kunitz-type protease inhibitor such as bovine pancreatic trypsin inhibitor (BPTI), amyloid precursor protein (APP) or tissue factor pathway inhibitor (TFPI). Kunitz domains have a molecular weight of approximately 6 kDA and domains with the required target specificity, i.e. against the site-specifically ADP-ribosylated protein or peptide, can be selected by display techniques such as phage display (Weidle et al., (2013), Cancer Genomics Proteomics; 10 (4): 155-68).

As used herein, the term "Fynomer®" refers to a non-immunoglobulin-derived binding polypeptide derived from the human Fyn SH3 domain. Fyn SH3-derived polypeptides are well-known in the art and have been described e.g. in Grabulovski et al. (2007) JBC, 282, p. 3196-3204, WO 2008/022759, Bertschinger et al (2007) Protein Eng Des Sel 20 (2): 57-68, Gebauer and Skerra (2009) Curr Opinion in Chemical Biology 13:245-255, or Schlatter et al. (2012), MAbs 4:4, 1-12).

Aptamers are nucleic acid molecules or peptide molecules that bind a specific target molecule.

Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications (Osborne et. al. (1997), Current Opinion in Chemical Biology, 1:5-9; Stull & Szoka (1995), Pharmaceutical Research, 12, 4:465-483).

Nucleic acid aptamers are nucleic acid species that normally consist of (usually short) strands of oligonucleotides. Typically, they have been engineered through repeated rounds of in vitro selection or equivalently, SELEX (systematic evolution of ligands by exponential enrichment) to bind to various molecular targets such as small molecules, proteins, nucleic acids, and even cells, tissues and organisms.

Peptide aptamers are usually peptides or proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable peptide loop typically comprises 10 to 20 amino acids, and the scaffold may be any protein having good solubility properties. Currently, the bacterial protein Thioredoxin-A is the most commonly used scaffold protein, the variable peptide loop being inserted within the redox-active site. Peptide aptamer selection can be made using different systems, but the most widely used is currently the yeast two-hybrid system.

Aptamers offer the utility for biotechnological and therapeutic applications as they offer molecular recognition properties that rival those of the commonly used biomolecules, in particular antibodies. In addition to their discriminatory recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamers' inherently low molecular weight. Unmodified aptamer applications currently focus on treating transient conditions such as blood clotting, or treating organs such as the eye where local delivery is possible. This rapid clearance can be an advantage in applications such as in vivo diagnostic imaging. Several modifications, such as 2'-fluorine-substituted pyrimidines, polyethylene glycol (PEG) linkage, fusion to albumin or other half life extending proteins etc. are available to scientists such that the half-life of aptamers can be increased for several days or even weeks.

The present invention relates in a fifth aspect to a composition, preferably a pharmaceutical, diagnostic or cosmetic composition, comprising the site-specifically ADP-ribosylated protein or peptide of the second or third aspect of the invention or the antibody of the fourth aspect of the invention.

The terms "composition", "pharmaceutical composition", "diagnostic composition" and "cosmetic composition" as well as their ingredients have been discussed herein above in connection with the first aspect of the invention. This disclosure is equally applicable to the fourth aspect of the invention.

The present invention relates in a sixth aspect to a method for producing a site-specifically serine ADP-ribosylated protein or peptide, comprising: (a) subjecting a protein or peptide comprising or consisting of an amino acid sequence comprising two or more serines to a serine ADP-ribosylation reaction, wherein (i) at least one serine is phosphorylated and at least one serine is non-phosphorylated, and/or (ii) for at least one serine a lysine can be found up to four amino acids N- or C-terminally thereof, preferably can be found directly N-terminally thereof, wherein said lysine is acetylated.

With respect to the method of the sixth aspect of the invention it is to be understood that in step (a) (i) the at least one non-phosphorylated serine becomes ADP-ribosylated whereas the at least one phosphorylated serine is protected from serine ADP-ribosylation, and/or (ii) at least one serine becomes ADP-ribosylated whereas the at least one serine, wherein a lysine can be found up to four amino acids N- or C-terminally thereof, preferably can be found directly N-terminally thereof, wherein said lysine is acetylated, is partially protected from serine ADP-ribosylation. In the above method for the at least one serine to be site-specifically serine ADP-ribosylated no lysine can be found up to four amino acids N- or C-terminally thereof. It is furthermore preferred that the at least one serine being non-phosphorylate has a free side chain (—CH$_2$—OH), for example, carrying no chemical modification.

The definitions and preferred embodiments of the first to fifth aspect of the invention apply mutatis mutandis to the sixth aspect of the invention as far as being also applicable to the sixth aspect. For instance, the serine ADP-ribosylation reaction in the context of the sixth aspect of the invention may be done in the same way as in the context of the first aspect of the invention. Moreover, also in accordance with a sixth aspect of the invention step (a) may comprise the synthesis of the protein or peptide as defined in the method of the invention, wherein the synthesis preferably comprises a solid-phase peptide synthesis.

The lysine that can be found up to four amino acids N- or C-terminally of the serine can be found with increasing preference up to three amino acids, up to two or next to the serine, N- or C-terminally. Most preferred is a "KS" motive.

Acetylation (or in IUPAC nomenclature ethanoylation) describes a reaction that introduces an acetyl functional group into a chemical compound. Acetylation of proteins and peptides naturally occurs as a co-translational or a post-translational modification, for example, of histones, p53, and tubulins. Acetylated lysine residues were first discovered in histones regulating gene transcription, which is the reason why the enzymes catalyzing lysine (K) acetylation were termed histone acetyltransferases (HATs).

As discussed herein above, it has surprisingly been found that a phosphate group on a serine serves as a protection group against the addition of an ADP-ribose in an ADP-ribosylation reaction. It has been reported that the acetylation of a lysine which can be found up to four amino acids N- or C-terminally of the serine, partially protects such a serine from serine ADP-ribosylation (Liszczak et al, Nat Chem Biol 2018). Hence, unlike phosphorylated serine no complete protection from serine ADPr is achieved but instead the efficacy of the ADPr of that serine is reduced while the at least one other "unprotected" serine as comprised in the protein or peptide as described in accordance with sixth aspect of the invention is efficiently ADPr. Hence, the discussed lysine acetylation alone or together with serine phosphorylation further increase the possibilities to generate site-specifically serine ADP-ribosylated protein or peptide having a selected ADPr modification pattern.

In accordance with a preferred embodiment of the sixth aspect of the invention, the method further comprises (c) removing the phosphate group(s) from the at least one phosphorylated serine and/or removing the acetyl group(s) from the at least one acetylated lysine.

The phosphate group(s) may be removed as is detailed herein above in connection with the first aspect of the invention. The acetylation status of a lysine is reversible. Several families of enzymes that can deacetylase lysines are known.

Accordingly, in accordance with a more preferred embodiment of the sixth aspect of the invention, the acetyl group(s) is/are removed by an enzyme, preferably a deacetylase, more preferably an enzyme selected from the group consisting of histone deacetylases (HDACs) and sirtuins.

Histone deacetylases (HDACs) (EC 3.5.1.98, HDAC) are a class of enzymes that remove acetyl groups (O=C—CH3) from an ε—N-acetyl lysine amino acid on a histone, allowing the histones to wrap the DNA more tightly, and other non-histone proteins. HDACs are now also called lysine deacetylases (KDACs), to describe their function rather than their target, which also includes non-histone proteins. The HDAC is preferably selected from human HDACs 1 to 11.

Some, but not all, sirtuins are protein deacetylases. The sirtuin to be used in accordance with the present invention is a protein deacetylase. Unlike other known protein deacetylases, which simply hydrolyze acetyl-lysine residues, the sirtuin-mediated deacetylation reaction couples lysine deacetylation to NAD hydrolysis. This hydrolysis yields O-acetyl-ADP-ribose, the deacetylated substrate and nicotinamide, which is an inhibitor of sirtuin activity itself. In mammals, including human, seven sirtuins (SIRT1-7) are known. The sirtuin is preferably selected from human SIRT1, 2, 3, 5, 6 and 7 which all have deacetylase activity.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show.

FIG. 1. A. Schematic representation of the products of an ADP-ribosylation reaction when using a substrate that comprises at least two target serine. To note, the state-of-the-art methodology to enzymatically generate ADP-ribosylated substrates with more than one target serine cannot ensure site-specificity, creating a mixture of different ADPr species (same amino acid sequence, but modification on different residues). B. Schematic representation of a synthetic peptide corresponding to the amino acids 494-524 of human PARP-1. To note, this amino acid sequence comprises three target serines (underlined), which means that state-of-the-art enzymatic ADP-ribosylation reactions will produce a mixture of different ADPr species. C. Analysis of the ADP-ribosylation of four different variants of synthetic peptides corresponding to the amino acids 494-524 of human PARP-1 (2 µg). In vitro ADP-ribosylation assays were performed as previously described (Bonfiglio et al, Mol Cell, 2017) with 5 UM NAD$^+$ and 63 nM (0.05 µCi/µl) $^{32}$P-NAD$^+$, Activated DNA, recombinant PARP-1 (0.1 µM) in the presence or absence of recombinant HPF1 WT (1 µM) for 20 minutes at 25° C. Samples were resolved by SDS-PAGE and analysed by autoradiography. D. Analysis of the ADP-ribosylation of two different variants of synthetic peptides corresponding to the amino acids 494-524 of human PARP-1. In vitro ADP-ribosylation assays were performed as described in panel C, in the presence or absence of recombinant HPF1 WT or Y238A/R239A mutant (1 µM). Samples were resolved by SDS-PAGE and analysed by autoradiography. FIG. 1D is taken from in Bonfiglio et al., 2017, loc. lit. E. Representative chromatogram illustrating the non-selective Ser-ADPr on substrates with more than one target serine. Biotinylated PARP-1 (494-511) was subjected to incomplete in vitro enzymatic ADPr and analysed by LC-MS. As depicted, the presence of two target serine (Ser499 and S507) results in non-selective reactions generating heterogenous mixtures of modified species that differ in the positions at which ADP-ribose is attached. For simplicity, the chromatogram shows only the m/z ranges in which mono- and di-ADP-ribosylated PARP-1 peptides were detected (m/z=624.63-624.97 and m/z=759.91-760.13).

Figure 2:
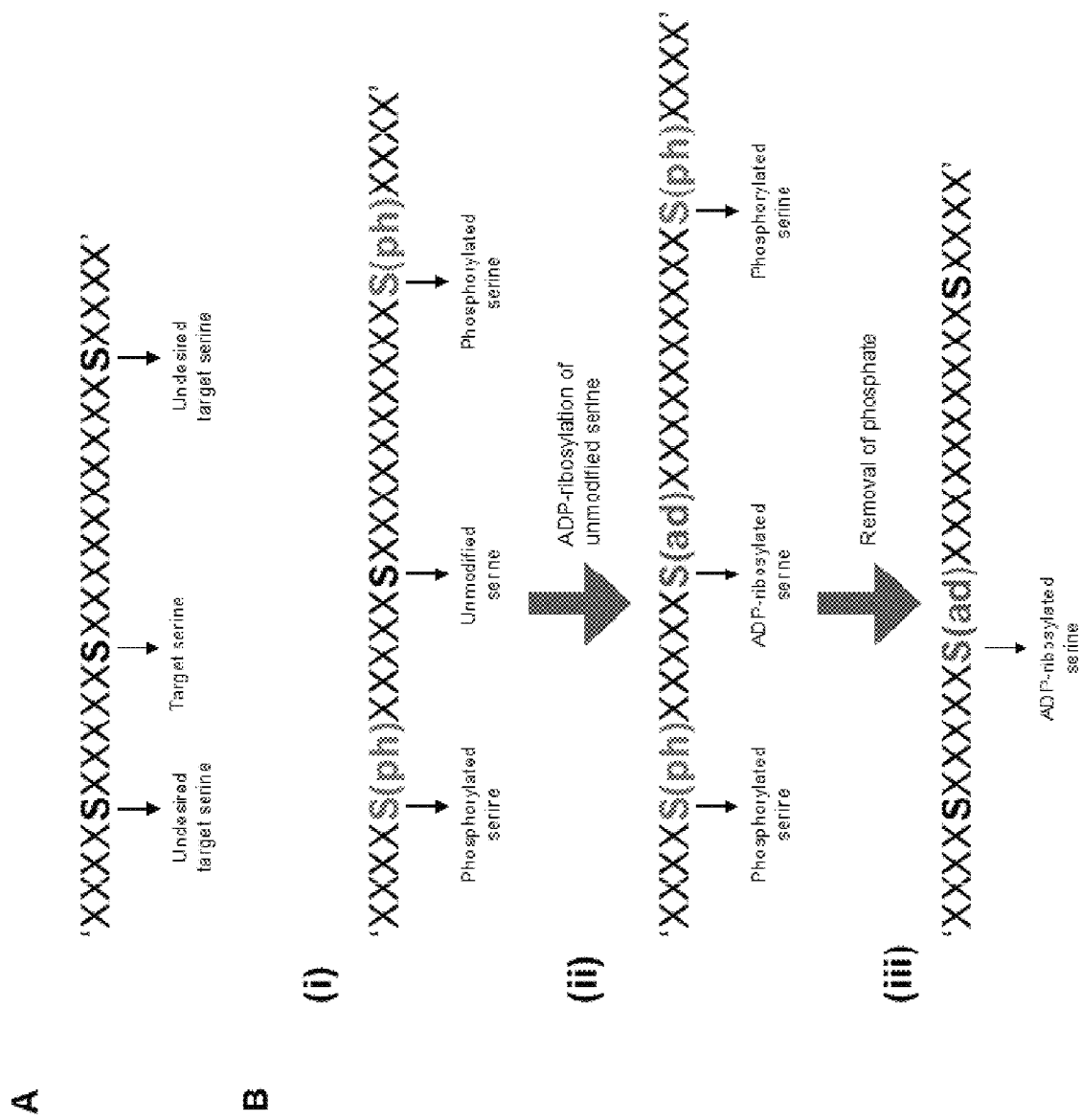

FIG. 2. A. Schematic representation of the protein or peptide with naturally-occurring amino acid sequence that is intended to be site-specifically ADP-ribosylated. To note, the amino acid sequence of the protein or peptide to be modified comprises at least two target serines. B. Schematic workflow for the means and methods for production of site-specific serine ADP-ribosylated protein or peptide with naturally-occurring amino acid sequences with two or more serines. The strategy consists of (i) providing a protein or peptide comprising or consisting of a naturally-occurring amino acid sequence comprising two or more serines, wherein at least one serine is phosphorylated and at least one serine is non-phosphorylated; (ii) subjecting such protein or protein to a serine ADP-ribosylation reaction; (iii) removing phosphorylation from the phosphorylated serine residues of (ii), thereby obtaining a site-specific Ser-ADPr protein or peptide with naturally-occurring amino acid sequence.

FIG. 3. A. Production of a site-specific ADP-ribosylated form of a PARP-1 peptide corresponding to the human amino acid sequence (494-514). 2 µg of Biotinylated PARP-1 (494-517) S507ph peptide (lane 2) were subjected to phosphatase treatment (400 U of Lambda Phosphatase for 1 h at 30° C.) alone (lane 4), or to in vitro ADP-ribosylation (lane 6, 2 mM NAD$^+$, activated DNA, recombinant PARP-1 (0.1 µM) and recombinant HPF1 WT (1 µM) for 6 h at 25° C.) followed by phosphatase treatment (lane 8, 400 U of Lambda Phosphatase for 1 h at 30° C.). 2 µg of a PARP-1 (494-514) S507A peptide were used as a control (lanes 1, 3, 5 and 7). Using this system along the lines described herein, a single species site-specific ADP-ribosylated peptide PARP-1 at Ser-499 was obtained. (Lane 1) PARP-1 (494-514) S507A; (Lane 2) PARP-1 (494-514) S507ph; (Lane 3) PARP-1 (494-514) S507A treated with phosphatase; (Lane 4) PARP-1 (494-514) S507ph treated with phosphatase; (Lane 5) PARP-1 (494-514) S507A subjected to in vitro ADPr; (Lane 6) PARP-1 (494-514) S507ph subjected to in vitro ADPr; (Lane 7) PARP-1 (494-514) S507A subjected to in vitro ADPr followed by phosphatase treatment; and (Lane 8) PARP-1 (494-514) S507ph subjected to in vitro ADPr followed by phosphatase treatment. B. Deconvoluted MS spectra displaying the different peptide species described in FIG. 2B. Unmodified biotinylated PARP-1 (494-511) peptide with two target serine (Ser499 and Ser507) was synthesized with phosphorylation in Ser507 and subjected to enzymatic HPF1/PARP-1 ADPr, generating an intermediate species comprising Ser499-ADPr and Ser507-phosphorylation. After ADPr reaction, phosphate from Ser507 was removed by Lambda phosphatase, producing biotinylated PARP-1 (494-511) Ser499-ADPr peptide. As depicted, chemically synthesized peptide containing S507ph is shifted 79.96 Da with respect to the unmodified counterpart (mass of phosphorylation=79.96 Da). Next, in vitro reaction produces a shift of 541.06 Da (mass of ADPr=541.06 Da) and finally, treatment with lambda phosphatase produces a negative shift of 79.96 Da, indicating the removal of phosphorylation. The final product is pure PARP-1 (494-511) Ser499 ADP-ribosylated peptide. C. Production of a site-specific ADP-ribosylated form of a Histone H2B peptide corresponding to the human amino acid sequence (1-32). 2 µg of Biotinylated Histone H2B (1-32) S14ph peptide (lane 2) were subjected to phosphatase treatment (400 U of Lambda Phosphatase for 1 h at 30° C.) alone (lane 1), or to in vitro ADP-ribosylation (lane 3, 2 mM NAD$^+$, activated DNA, recombinant PARP-1 (0.1 µM) and recombinant HPF1 WT (1 µM) for 6 h at 25° C.) followed by phosphatase treatment (lane 4, 400 U of Lambda Phosphatase for 1 h at 30° C.). Using this system along the lines described herein, a single species site-specific ADP-ribosylated peptide Histone H2B at Ser-6 was obtained. (Lane 1) Histone H2B (1-32); (Lane 2) Histone H2B (1-32) S14ph; (Lane 3) Histone H2B (1-32)

S14ph subjected to in vitro ADPr; (Lane 4) Histone H2B (1-32) S14ph subjected to in vitro ADPr followed by phosphatase treatment.

Figure 4:
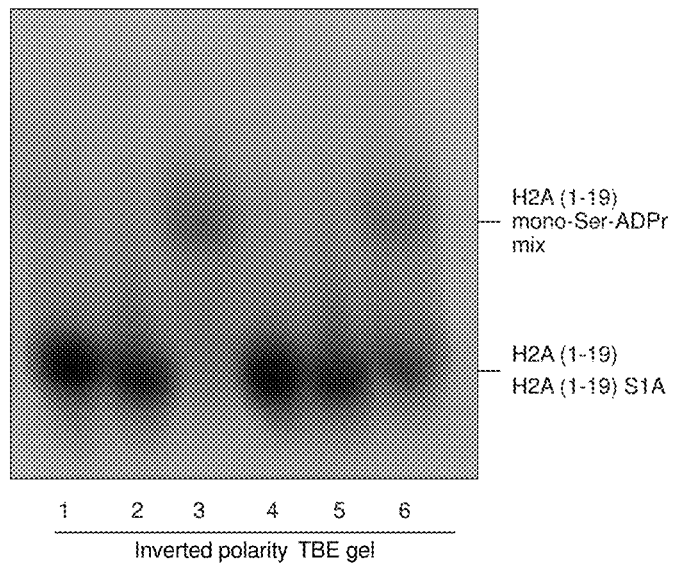
Figure 4:
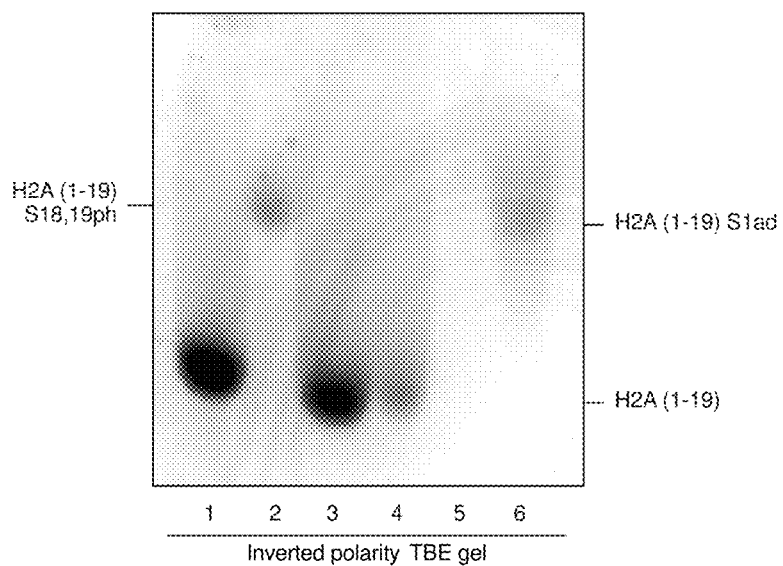

FIG. 4. A. A peptide with more than one target serine residue is still ADP-ribosylated after mutation of the main target serine residue. Representative stained gels (Imperial™ Protein Stain) illustrating the non-selective Ser-ADPr on substrates with more than one target serine. Histone H2A peptides in which the major target serine has been substituted by alanine (Histone H2A (1-19) S1A) are still ADP-ribosylated due to the presence of other target serines. Biotinylated Histone H2A (1-19) peptide (Lane 1) was reacted with 2 mM $NAD^+$ and 0.12 μM PARP-1 in the absence (Lane 2) or presence (Lane 3) of 1.5 μM HPF1 for 75 minutes at RT. Similarly, Biotinylated Histone H2A (1-19) S1A peptide (Lane 4) was reacted with 2 mM $NAD^+$ and 0.12 M PARP-1 in the absence (Lane 5) or presence (Lane 6) of 1.5 μM HPF1 for 75 minutes at RT. B. 2 μg of Biotinylated H2A (1-19) S18,19ph peptide (lane 2) was subjected to phosphatase treatment (400 U of Lambda Phosphatase for 1 h at 30° C.) alone (lane 4), or to in vitro ADP-ribosylation (lane 5, 2 mM $NAD^+$, Activated DNA, recombinant PARP-1 (0.1 μM) and recombinant HPF1 WT (1 μM) for 6 h at 25° C.) followed by phosphatase treatment (lane 6, 400 U of Lambda Phosphatase for 1 h at 30° C.). 2 μg of a H2A (1-19) peptide were used as a control (lanes 1 and 3). Following the strategy described in this application, a single species site-specific ADP-ribosylated peptide H2A at Ser-1 was obtained. (Lane 1) H2A (1-19) (Lane 2) H2A (1-19) S18,19ph (Lane 3) H2A (1-19) treated with phosphatase (Lane 4) H2A (1-19) S18,19ph treated with phosphatase (Lane 5) H2A (1-19) S18,19ph subjected to in vitro ADPr (Lane 6) H2A (1-19) S18,19ph subjected to in vitro ADPr followed by phosphatase treatment.

The examples illustrate the invention.

Example 1—Production of a Site-Specific ADP-Ribosylated Form of a PARP-1 Peptide Corresponding to the Human Amino Acid Sequence (494-514)

Unlike the commonly-used approach of replacing the undesired target serine with another residue, the methodology described in the present application does not require the replacement of serine residue(s) and the consequent use of a non-naturally-occurring sequence to prepare a protein or peptide being site-specifically serine ADP-ribosylated (FIG. 2). By these means, a site-specific-Ser499-ADP-ribosylated peptide corresponding to the naturally-occurring human amino acid sequence (494-514) of PARP-1 (FIGS. 3A and B) was obtained. Importantly, the PARP-1 Ser499-ADPr site is the main endogenous ADPr site upon DNA damage. A standard approach to prevent ADPr of Ser507 would be replacing this residue with alanine (FIG. 3A). However, the final ADP-ribosylated product will not carry the natural sequence, which might represent a drawback for downstream applications (e.g. generation of antibodies). To overcome this limitation, a novel strategy was designed that consists of obtaining by standard chemical synthesis, a phosphorylated Ser507 peptide that prevents ADPr of Ser507. After subjecting this peptide to ADPr reactions, the unmodified Ser-499 becomes ADP-ribosylated. As the resulting peptide is both phosphorylated and ADP-ribosylated, the phosphate is afterwards removed from the peptide without affecting ADP-ribosylation (e.g. a second enzymatic reaction with a recombinant commercially-available phosphatase). The resulting peptide is ADP-ribosylated on a specific serine and comprises a naturally-occurring sequence (FIGS. 2 and 3A and B). By the above-described means also a Histone H2B (1-32) which is site-specifically ADPr at Ser-6 was obtained (FIG. 3C).

Example 2—Production of a Site-Specific ADP-Ribosylated Form of a H2A Peptide Corresponding to the Human Amino Acid Sequence (1-19)

When a protein or peptide comprising at least two target serines is subjected to an ADP-ribosylation reaction, a mixture of different ADP-ribosylated species (same amino acid sequence, but modification on different residues) is generated (FIGS. 1A and 4). For example, the peptide corresponding to the human amino acid sequence (1-19) of H2A contains, in addition to the Ser-1, two additional Ser residues (Ser-18 and Ser-19) that have never been described in the literature as targets of ADPr. However, when mutating the only reported target serine (Ser-1), the peptide is still ADP-ribosylated (FIG. 4A, lane 6), demonstrating the limitations of using a peptide with at least two target serine to obtain site-specific ADP-ribosylated species. The methodology described in the present application solves this problem by preventing the ADP-ribosylation of undesired Ser residues and therefore allowing the preparation of a protein or peptide being site-specifically serine ADP-ribosylated. The novel strategy consists of using a phosphorylated Ser peptide (Ser18 and Ser19 of this example, FIG. 4B) that prevents ADPr of those residues. Similarly to what has been described in Example 1, after subjecting the phosphorylated peptide to ADPr reactions, the unmodified Ser-1 becomes ADP-ribosylated and to remove the phosphates of Ser18 and Ser19, the peptide is subjected to a phosphate treatment (FIG. 4B).

Example 3—Experimental Conditions Under which Considerable Amounts of Pure PARP-1 Ser-499 Mono-ADP-Ribosylated Peptide were Obtained Given that some important applications require considerable amounts of serine ADP-ribosylated peptides (e.g. generation of antibodies), the inventors scaled up the reactions and under the following tested conditions have been able to produce ~ 500 μg of pure PARP-1 Ser-499 mono-ADP-ribosylated peptide:
Solvent: Water
Buffer: 50 mM Tris-HCl, pH=7.5;
Salts: 50 mM NaCl and 1 mM $MgCl_2$;
$NAD^+$: 2 mM;
PARP-1:100 nM;
HPF1: 1.5 UM;
Substrate peptide: 700 μg (Biotinylated PARP-1 (494-517) S507ph peptide)

The reaction mix was incubated for 360 minutes at RT, adding 2 mM $NAD^+$ every 120 minutes and stopped by adding 1 μM Olaparib. Afterwards, 1 mM $MnCl2$, 1×PMP buffer (New England Biolabs), 8000 U of Lambda Protein Phosphatase (Lambda P P, New England Biolabs) and 1 μM PARG were added to the reaction mix and it was incubated for 300 minutes at 30° C. Afterwards, the serine mono-ADP-ribosylated peptides were separated from the other constituents of the reaction mix by using reverse chromatography (C18 cartridge). Pure mono-Ser-499 ADP-ribosylated Biotinylated PARP-1 (494-517) peptide was eluted with 30% Acetonitrile.

The invention claimed is:

1. A method for producing a site-specifically serine Adenosine Diphosphate (ADP)-ribosylated protein or peptide, comprising:
   (a) subjecting to a serine ADP-ribosylation reaction a protein or peptide comprising an amino acid sequence having two or more serines, wherein at least one specified serine is phosphorylated to contain one or more phosphate groups, and at least one specified serine is non-phosphorylated,
   wherein the at least one specified non-phosphorylated serine becomes ADP-ribosylated and the at least one specified phosphorylated serine is protected from serine ADP-ribosylation, thereby obtaining a site-specific serine ADP-ribosylated protein or peptide.

2. The method of claim 1, further comprising
   (b) removing the phosphate group(s) from the at least one specified phosphorylated serine.

3. The method of claim 2, wherein the phosphate group(s) is/are removed by an enzyme selected from the group consisting of lambda protein phosphatase, calf intestinal phosphatase (CIP), antarctic phosphatase (AnP), shrimp alkaline phosphatase (SAP), and mixtures thereof.

4. The method of claim 1, wherein step (a) comprises the synthesis of the protein or peptide as defined in claim 1, wherein the synthesis comprises a solid-phase peptide synthesis.

5. The method of claim 1, wherein the serine ADP-ribosylation reaction is carried out in an ADP-ribosylation reaction mixture, said mixture comprising
   (i) a buffered solution,
   (ii) Nicotinamide adenine dinucleotide$^+$ (NAD$^+$),
   (iii) Poly (ADP-ribose) polymerase (PARP)-1, PARP-2 or the PARP-1 variant E988Q designated SEQ ID NO: 2,
   (iv) Histone PARyulation Factor 1 (HPF1),
   (v) sonicated DNA, and
   (vi) the protein or peptide as defined in claim 1, step (a).

6. The method of claim 1, further comprising purifying the site-specifically serine ADP-ribosylated protein or peptide.

7. The method of claim 6, wherein the site-specifically serine ADP-ribosylated protein or peptide is purified by StageTip fractionation employing C8, C18, SCX, SAX or SDB-RPS chromatography.

8. The method of claim 1, further comprising formulating the produced site-specifically serine ADP-ribosylated protein or peptide into a composition selected from a pharmaceutical, diagnostic or cosmetic composition.

9. The method of claim 1, wherein the protein or peptide further comprises at least one post-translational modification other than serine ADP-ribosylation and serine phosphorylation.

10. The method of claim 9, wherein the post-translational modification is selected from lipidation, N- or O-linked glycosylation, phosphorylation of an amino acid other than serine, acetylation, amidation, hydroxylation, mono- or di- or tri-methylation, ubiquitylation, SUMOylation, neddylation, butyrylation, propionylation, crotonylation, 2-hydroxyisobutyrylation, malonylation, succinylation, citrullination, pyrrolidone carboxylic acid and sulfation.

11. The method of claim 1, wherein the method is carried out ex vivo or in vitro.

12. The method of claim 6, wherein the site-specifically serine ADP-ribosylated protein or peptide is purified by cation or anion exchange chromatography, hydrophilic interaction chromatography, or boronate affinity chromatography.

13. The method of claim 6, wherein the site-specifically serine ADP-ribosylated protein or peptide is purified by phosphopeptide enrichment.

14. The method of claim 6, wherein the site-specifically serine ADP-ribosylated protein or peptide is purified by enrichment with an ADP-ribose-binding protein domain.

15. The method of claim 6, wherein the site-specifically serine ADP-ribosylated protein or peptide is purified by filtering the reaction with an ultrafiltration device.

16. The method of claim 6, wherein the site-specifically serine ADP-ribosylated protein or peptide is purified by a spin column.

* * * * *